(12) United States Patent
Clark, III et al.

(10) Patent No.: US 9,408,608 B2
(45) Date of Patent: Aug. 9, 2016

(54) TISSUE LIGATION DEVICES AND METHODS THEREFOR

(71) Applicant: SentreHEART, Inc., Redwood City, CA (US)

(72) Inventors: Robert L. Clark, III, Hayward, CA (US); Gregory W. Fung, Redwood Shores, CA (US); Russell Pong, Newark, CA (US); Arnold M. Escano, Santa Clara, CA (US); Greg Liu, Sunnyvale, CA (US)

(73) Assignee: SentreHEART, Inc., Redwood City, CA (US)

( * ) Notice: Subject to any disclaimer, the term of this patent is extended or adjusted under 35 U.S.C. 154(b) by 344 days.

(21) Appl. No.: 14/195,797

(22) Filed: Mar. 3, 2014

(65) Prior Publication Data

US 2014/0276985 A1 Sep. 18, 2014

Related U.S. Application Data

(60) Provisional application No. 61/778,251, filed on Mar. 12, 2013.

(51) Int. Cl.
*A61B 17/24* (2006.01)
*A61B 17/26* (2006.01)
*A61B 17/12* (2006.01)
(Continued)

(52) U.S. Cl.
CPC ....... *A61B 17/12013* (2013.01); *A61B 17/0218* (2013.01); *A61B 2017/00243* (2013.01); *A61B 2017/00557* (2013.01); *A61B 2017/00867* (2013.01); *A61B 2017/00876* (2013.01)

(58) Field of Classification Search
CPC ............... A61B 17/12013; A61B 2017/00876; A61B 17/0218; A61B 2017/00867; A61B 2017/00557; A61B 2017/00243; A61B 1/005; A61B 1/012
USPC ........................................................ 606/113
See application file for complete search history.

(56) References Cited

U.S. PATENT DOCUMENTS

| 3,496,932 A | 2/1970 | Prisk et al. |
| 3,677,597 A | 7/1972 | Stipek |
| 3,802,074 A | 4/1974 | Hoppe |

(Continued)

FOREIGN PATENT DOCUMENTS

| EP | 0 598 219 A2 | 5/1994 |
| EP | 0 598 219 A3 | 5/1994 |

(Continued)

OTHER PUBLICATIONS

Australian Office Action mailed on Mar. 13, 2015, for Australian Patent Application No. 2014202620, filed on Mar. 25, 2008, three pages.

(Continued)

*Primary Examiner* — Amy R Weisberg
(74) *Attorney, Agent, or Firm* — Morrison & Foerster LLP

(57) ABSTRACT

Described here are closure devices and methods for ligating tissue, such as the left atrial appendage. The closure devices may comprise a snare loop assembly comprising a snare and a suture loop releasably attached thereto. The snare may be releasable from an elongate body of the closure device. In some instances, the closure device may comprise one or more markers to allow a user to determine whether the snare loop assembly is twisted.

24 Claims, 28 Drawing Sheets

(51) Int. Cl.
*A61B 17/02* (2006.01)
*A61B 17/00* (2006.01)

(56) References Cited

U.S. PATENT DOCUMENTS

| | | |
|---|---|---|
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,226,535 A | 7/1993 | Roshdy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,229 A | 8/1994 | Noda |
| 5,336,252 A | 8/1994 | Cohen |
| 5,385,156 A | 1/1995 | Oliva |
| 5,387,219 A | 2/1995 | Rappe |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,367 A | 9/1995 | Kadry |
| 5,494,240 A | 2/1996 | Waugh |
| 5,498,228 A | 3/1996 | Royalty et al. |
| 5,540,711 A | 7/1996 | Kieturakis et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,636,780 A | 6/1997 | Green et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,788,715 A | 8/1998 | Watson, Jr. et al. |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,855,586 A * | 1/1999 | Habara ............ A61B 17/12009 606/139 |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |

(56) References Cited

U.S. PATENT DOCUMENTS

| | | |
|---|---|---|
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,608,091 B2 | 10/2009 | Goldfarb et al. |
| 7,618,425 B2 | 11/2009 | Yamamoto et al. |
| 7,722,641 B2 | 5/2010 | van der Burg et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 7,967,808 B2 | 6/2011 | Fitzgerald et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,636,767 B2 | 1/2014 | McClain |
| 8,771,297 B2 | 7/2014 | Miller et al. |
| 8,795,297 B2 | 8/2014 | Liddicoat et al. |
| 8,814,778 B2 | 8/2014 | Kiser et al. |
| 8,986,325 B2 | 3/2015 | Miller et al. |
| 9,198,664 B2 | 12/2015 | Fung et al. |
| 2001/0025132 A1 | 9/2001 | Alferness et al. |
| 2002/0017306 A1 | 2/2002 | Cox et al. |
| 2002/0022860 A1 | 2/2002 | Borillo et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1 | 3/2004 | Burbank et al. |
| 2004/0064138 A1 | 4/2004 | Grabek |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043745 A1 | 2/2005 | Alferness et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0154404 A1 | 7/2005 | Liddicoat et al. |
| 2005/0165466 A1 | 7/2005 | Morris et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0100545 A1 | 5/2006 | Ayala et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2006/0253129 A1 | 11/2006 | Liddicoat et al. |
| 2007/0010829 A1 | 1/2007 | Nobles et al. |
| 2007/0016228 A1 | 1/2007 | Salas |
| 2007/0027456 A1 | 2/2007 | Gartner et al. |
| 2007/0038229 A1 | 2/2007 | de la Torre et al. |
| 2007/0060951 A1 | 3/2007 | Shannon |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0088369 A1 | 4/2007 | Shaw et al. |
| 2007/0100405 A1 | 5/2007 | Thompson et al. |

(56) References Cited

U.S. PATENT DOCUMENTS

| | | | |
|---|---|---|---|
| 2007/0135822 A1 | 6/2007 | Onuki et al. | |
| 2007/0149988 A1 | 6/2007 | Michler et al. | |
| 2007/0179345 A1 | 8/2007 | Santilli | |
| 2007/0249991 A1 | 10/2007 | Whayne et al. | |
| 2007/0260278 A1 | 11/2007 | Wheeler et al. | |
| 2007/0270637 A1 | 11/2007 | Takemoto et al. | |
| 2007/0270891 A1 | 11/2007 | McGuckin, Jr. | |
| 2008/0009843 A1 | 1/2008 | de la Torre | |
| 2008/0033241 A1 | 2/2008 | Peh et al. | |
| 2008/0033457 A1 | 2/2008 | Francischelli et al. | |
| 2008/0039879 A1 | 2/2008 | Chin et al. | |
| 2008/0097489 A1 | 4/2008 | Goldfarb et al. | |
| 2008/0147097 A1 | 6/2008 | Liddicoat et al. | |
| 2008/0221593 A1 | 9/2008 | Liddicoat et al. | |
| 2008/0228265 A1 | 9/2008 | Spence et al. | |
| 2008/0243183 A1 | 10/2008 | Miller et al. | |
| 2008/0269782 A1 | 10/2008 | Stefanchik et al. | |
| 2008/0294174 A1 | 11/2008 | Bardsley et al. | |
| 2008/0294175 A1 | 11/2008 | Bardsley et al. | |
| 2008/0312664 A1 | 12/2008 | Bardsley et al. | |
| 2009/0043317 A1 | 2/2009 | Cavanaugh et al. | |
| 2009/0082797 A1 | 3/2009 | Fung et al. | |
| 2009/0088778 A1* | 4/2009 | Miyamoto | A61B 17/0401 606/144 |
| 2009/0143791 A1 | 6/2009 | Miller et al. | |
| 2009/0157118 A1 | 6/2009 | Miller et al. | |
| 2010/0069925 A1 | 3/2010 | Friedman et al. | |
| 2010/0174296 A1 | 7/2010 | Vakharia et al. | |
| 2011/0087247 A1 | 4/2011 | Fung et al. | |
| 2011/0106107 A1* | 5/2011 | Binmoeller | A61B 17/0487 606/139 |
| 2011/0144660 A1 | 6/2011 | Liddicoat et al. | |
| 2012/0209300 A1 | 8/2012 | Torrie | |
| 2012/0330351 A1 | 12/2012 | Friedman et al. | |
| 2013/0144311 A1 | 6/2013 | Fung et al. | |
| 2014/0018831 A1 | 1/2014 | Kassab et al. | |
| 2014/0276911 A1* | 9/2014 | Smith | A61B 17/221 606/113 |
| 2014/0364901 A1 | 12/2014 | Kiser et al. | |
| 2015/0025312 A1 | 1/2015 | de Canniere | |
| 2015/0157328 A1 | 6/2015 | Miller et al. | |
| 2015/0173765 A1 | 6/2015 | Miller et al. | |
| 2015/0182225 A1 | 7/2015 | Morejohn et al. | |
| 2015/0190135 A1 | 7/2015 | Ibrahim et al. | |
| 2015/0250482 A1 | 9/2015 | Slaughter et al. | |

FOREIGN PATENT DOCUMENTS

| | | |
|---|---|---|
| EP | 0 598 219 B1 | 5/1994 |
| EP | 1 010 397 A1 | 6/2000 |
| GB | 1 506 142 A | 4/1978 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-540834 A | 12/2002 |
| JP | 2002-540901 A | 12/2002 |
| JP | 2003-225241 A | 8/2003 |
| JP | 2004-000601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| WO | WO-94/01045 A1 | 1/1994 |
| WO | WO-94/04079 A1 | 3/1994 |
| WO | WO-94/08514 A1 | 4/1994 |
| WO | WO-96/40356 A1 | 12/1996 |
| WO | WO-97/11644 A1 | 4/1997 |
| WO | WO-97/43957 A1 | 11/1997 |
| WO | WO-00/59383 A1 | 10/2000 |
| WO | WO-00/61202 A1 | 10/2000 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034802 A2 | 4/2005 |
| WO | WO-2005/034802 A3 | 4/2005 |
| WO | WO-2006/096805 A1 | 9/2006 |
| WO | WO-2006/110734 A2 | 10/2006 |
| WO | WO-2006/115689 A1 | 11/2006 |
| WO | WO-2007/056502 A1 | 5/2007 |
| WO | WO-2008/017080 A2 | 2/2008 |
| WO | WO-2008/017080 A3 | 2/2008 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2012/170652 A1 | 12/2012 |

OTHER PUBLICATIONS

Australian Office Action mailed on Feb. 26, 2016 for Australian Patent Application No. 2015200980, filed on Feb. 26, 2015, four pages.
Chinese Office Action mailed on Jun. 25, 2014, for Chinese Patent Application No. 201080023899.9, filed on Apr. 1, 2010, 5 pages.
European Communication mailed on Oct. 17, 2014, for European Patent Application No. 12186090.2, filed on Mar. 25, 2008, 8 pages.
Extended European Search Report mailed on Jul. 10, 2015, for European Patent Application No. 15153029.2, filed on Mar. 25, 2008, 6 pages.
Final Office Action mailed on Aug. 12, 2014, for U.S. Appl. No. 13/033,532, filed Feb. 23, 2011, 6 pages.
Final Office Action mailed on Nov. 14, 2014, for U.S. Appl. No. 12/363,359, filed Jan. 30, 2009, 10 pages.
Final Office Action mailed on Mar. 17, 2016, for U.S. Appl. No. 12/363,359, filed Jan. 30, 2009, 9 pages.
International Search Report mailed on Aug. 8, 2014, for PCT Application No. PCT/US2014/020030, filed on Mar. 3, 2014, 4 pages.
Japanese Office Action mailed on Jul. 29, 2014, for Japanese Patent Application No. 2013-206216, filed on Mar. 25, 2008, 2 pages.
Japanese Office Action mailed on Aug. 4, 2015, for Japanese Patent Application No. 2014-179551, filed on Apr. 1, 2010, 2 pages.
Non-Final Office Action mailed on Nov. 10, 2014, for U.S. Appl. No. 12/752,873, filed Apr. 1, 2010, 10 pages.
Non-Final Office Action mailed on May 4, 2015, for U.S. Appl. No. 12/124,023, filed May 20, 2008, 8 pages.
Non-Final Office Action mailed on Sep. 10, 2015, for U.S. Appl. No. 12/363,359, filed Jan. 30, 2009, 12 pages.
Non-Final Office Action mailed on Oct. 28, 2015, for U.S. Appl. No. 13/033,532, filed Feb. 23, 2011, 9 pages.
Notice of Allowance mailed on Dec. 29, 2014, for U.S. Appl. No. 12/363,381, filed Jan. 30, 2009, 9 pages.
Notice of Allowance mailed on Jul. 22, 2015, for U.S. Appl. No. 12/752,873, filed Apr. 1, 2010, 8 pages.
Notice of Allowance mailed on Oct. 21, 2015, for U.S. Appl. No. 12/124,023, filed May 20, 2008, 9 pages.
Notice of Allowance mailed on Nov. 18, 2014, for Australian Patent Application No. 2010232589, filed on Apr. 1, 2010, 3 pages.
Notice of Allowance mailed on Apr. 24, 2015, for Australian Patent Application No. 2014202620, filed on Mar. 25, 2008, 2 pages.
Notice of Allowance mailed on Jan. 29, 2015, for Canadian Patent Application No. 2682398, filed on Mar. 25, 2008, 1 page.
Written Opinion of the International Searching Authority mailed on Aug. 8, 2014, for PCT Application No. PCT/US2014/020030, filed on Mar. 3, 2014, 6 pages.
Notice of Allowance mailed on Mar. 26, 2015, for European Patent Application No. 12186090.2, filed on Mar. 25, 2008, 2 pages.
U.S. Appl. No. 14/928,836, filed Oct. 30, 2015, for Fung et al.
afibfacts.com (Date Unknown). "Cox-Maze III: The Gold Standard Treatment for Atrial Fibrillation: Developing a Surgical Option for

(56) References Cited

OTHER PUBLICATIONS

Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.
Al-Saady, N.M. et al. (1999). "Left Atrial Appendage: Structure, Function, and Role in Thromboembolism," *Heart* 82:547-554.
Albers, G.W. (Jul. 11, 1994). "Atrial Fibrillation and Stroke: Three New Studies, Three Remaining Questions," *Arch Intern Med* 154:1443-1448.
Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.
Aronow, W.S. et al. (Apr. 2009). "Atrial Fibrillation: The New Epidemic of the Age-ing World," *Journal of Atrial Fibrillation* 1(6):337-361.
Australian Office Action mailed on Mar. 28, 2014 for Australian Patent Application No. 2010232589, filed on Oct. 12, 2011, four pages. (5.41).
Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.
Bath, P.M.W. et al. (2005). "Current Status of Stroke Prevention in Patients with Atrial Fibrillation," *European Heart Journal Supplements* 7(Supplement C):C12-C18.
Benjamin, B.A. et al. (1994). "Effect of Bilateral Atrial Appendectomy on Postprandial Sodium Excretion in Conscious Monkeys," *Society for Exp. Biology and Med.* 2006: 1 page.
Beygui, F. et al. (2005, e-pub. Oct. 21, 2005). "Multimodality Imaging of Percutaneous Closure of the Left Atrial Appendage," *Clinical Vignette*, 1 page.
Bisleri, G. et al. (Jun. 3, 2005). "Innovative Monolateral Approach for Closed-Chest Atrial Fibrillation Surgery," *The Annals of Thoracic Surgery* 80:e22-e25.
Björk, V.O. et al. (Aug. 1961). "Sequelae of Left Ventricular Puncture with Angiocardiography," *Circulation* 24:204-212.
Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.
Blackshear, J.L. et al. (Oct. 1, 2003). "Thoracoscopic Extracardiac Obliteration of the Left Atrial Appendage for Stroke Risk Reduction in Atrial Fibrillation," *J. Am. Coll. Cardiol.* 42(7):1249-1252.
Bonanomi, G. et al. (Jan. 1, 2003). "Left Atrial Appendectomy and Maze," *Journal of the American College of Cardiology* 41(1):169-171.
Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Circulation* 98:1949-1984.
Botham, R.J. et al. (May 1959). "Pericardial Tamponade Following Percutaneous Left Ventricular Puncture," *Circulation* 19:741-744.
Brock, R. et al. (1956). "Percutaneous Left Ventricular Puncture in the Assessment of Aortic Stenosis," *Thorax* 11:163-171.
Burke, R.P. et al. (1992). "Improved Surgical Approach to Left Atrial Appendage Aneurysm," *Journal of Cardiac Surgery* 7(2):104-107.
Canaccord Adams (Aug. 11, 2008). "A-Fib: Near A Tipping Point," 167 pages.
Canadian Office Action mailed on Apr. 16, 2014 for Canadian Patent Application No. 2,682,398, filed on Mar. 25, 2008, 4 pages.
Chinese Office Action mailed on Dec. 4, 2013 for Chinese Patent Application No. 201080023899.9, filed on Apr. 1, 2010, 4 pages.
Chung, M.K. (Jul. 2003). "Current Clinical Issues in Atrial Fibrillation," *Cleveland Clinic Journal of Medicine* 70(Supp. 3):S6-S11.
Coffin, L.H. (Jun. 1985). "Use of the Surgical Stapler to Obliterate the Left Atrial Appendage," *Surgery, Gynecology & Obstetrics* 160:565-566.
Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.
Costa, R. et al. (2006). "Bi-Atrial Subxiphoid Epicardial Pacemaker in Superior Vena Cava Syndrome," *Arq. Bras. Cardiol.* 87:e45-e47.
Cox, J.L. et al. (Apr. 1991). "The Surgical Treatment of Atrial Fibrillation: IV. Surgical Technique," *J. Thorac. Cardiovasc. Surg.* 101(4):584-592.
Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.
Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.
Cox, J.L. et al. (Nov. 1999). "Impact of the Maze Procedure on the Stroke Rate in Patients with Atrial Fibrillation," *J. Thorac. Cardiovasc. Surg.* 118:833-840.
Cox, J.L. et al. (2004). "The Role of Surgical Intervention in the Management of Atrial Fibrillation," *Texas Heart Institute Journal* 31(3):257-265.
Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.
D'Avila, A. et al. (Apr. 2003). "Pericardial Anatomy for the Interventional Electrophysiologist," *Journal of Cardiovascular Electrophysiology* 14(4):422-430.
D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.
Demaria, A.N. et al. (Dec. 17, 2003). "Highlights of the Year JACC 2003," *Journal of the American College of Cardiology* 42(12):2156-2166.
Deneu, S. et al. (Jul. 11, 1999). "Catheter Entrapment by Atrial Suture During Minimally Invasive Port-access Cardiac Surgery," *Canadian Journal of Anesthesia* 46(10):983-986.
Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.
Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.
Donnino, R. et al. (2007). "Left Atrial Appendage Thrombus Outside of a 'Successful' Ligation," *European Journal of Echocardiography* pp. 1-2.
Dullum, M.K.C. et al. (1999). "Xyphoid MIDCAB: Report of the Technique and Experience with a Less Invasive Midcab Procedure," *Heart Surgery Forum* 2(1):77-81.
European Office Action mailed on Sep. 16, 2010, for European Patent Application No. 08727155.7, filed on Mar. 25, 2008, 5 pages. (3.44).
Feinberg, W.M. et al. (Mar. 13, 1995). "Prevalence, Age Distribution, and Gender of Patients With Atrial Fibrillation," *Arch Intern Med* 155:469-473.
Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.
Final Office Action mailed on Jun. 22, 2009, for U.S. Appl. No. 10/963,371, filed Oct. 11, 2004, 11 pages.
Final Office Action mailed on Apr. 14, 2010, for U.S. Appl. No. 11/600,671, filed Nov. 15, 2006, 7 pages.
Final Office Action mailed on Jul. 21, 2010, for U.S. Appl. No. 11/400,714, filed Apr. 7, 2006, 10 pages.
Final Office Action mailed on Apr. 26, 2011, for U.S. Appl. No. 12/037,802, filed Feb. 26, 2008, 9 pages.
Final Office Action mailed on Sep. 20, 2011, for U.S. Appl. No. 12/212,511, filed Sep. 17, 2008, 8 pages.
Final Office Action mailed on Oct. 28, 2011, for U.S. Appl. No. 12/055,213, filed Mar. 25, 2008, 15 pages.

(56) References Cited

OTHER PUBLICATIONS

Final Office Action mailed on May 4, 2012, for U.S. Appl. No. 12/363,359, filed Jan. 30, 2009, 10 pages.
Final Office Action mailed on May 16, 2012, for U.S. Appl. No. 12/363,381, filed Jan. 30, 2009, 8 pages.
Final Office Action mailed on Jul. 11, 2012, for U.S. Appl. No. 13/033,532, filed Feb. 23, 2011, 8 pages.
Final Office Action mailed on Jul. 24, 2012, for U.S. Appl. No. 12/212,511, filed Sep. 17, 2008, 6 pages.
Final Office Action mailed on Oct. 18, 2012, for U.S. Appl. No. 12/124,023, filed May 20, 2008, 15 pages.
Final Office Action mailed on Nov. 8, 2013, for U.S. Appl. No. 12/037,802, filed Feb. 26, 2008, 15 pages.
Final Office Action mailed on Jan. 13, 2014, for U.S. Appl. No. 12/752,873, filed Apr. 1, 2010, 10 pages.
Fisher, D.C. et al. (Dec. 1998). "Large Gradient Across a Partially Ligated Left Atrial Appendage," *Journal of the American Society of Echocardiography* 11(12):1163-1165.
Friberg, L. et al. (2006). "Stroke Prophylaxis in Atrial Fibrillation: Who Gets it and Who Does Not?" *European Heart Journal* 27:1954-1964.
Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.
Fuster, V. et al. (Oct. 2001). "ACC/AHA/ESC Guidelines for the Management of Patients with Atrial Fibrillation," *European Heart Journal* 22(20):1852-1923.
Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.
Gardiner, G.A. Jr. et al. (Apr. 1986). "Complications of Transluminal Angioplasty," *Radiology* 159:201-208.
Gillinov, A.M. (2007). "Advances in Surgical Treatment of Atrial Fibrillation," *Stroke* 38(part 2):618-623.
Gilman, R.A. et al. (Apr. 1963). "Direct Left Ventricular Puncture," *California Medicine* 98(4):200-203.
Goodwin, W.E. et al. (Nov. 1950). "Translumbar Aortic Puncture and Retrograde Catheterization of the Aorta in Aortography and Renal Arteriography," *Annals of Surgery* 132(5):944-958.
Gottlieb, L.K. et al. (Sep. 12, 1994). "Anticoagulation in Atrial Fibrillation," *Arch. Intern. Med.* 154:1945-1953.
Graffigna, A. et al. (1993). "Surgical Treatment of Wolff-Parkinson-White Syndrome: Epicardial Approach Without the Use of Cardiopulmonary Bypass," *J. Card. Surg.* 8:108-116.
Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.
Halperin, J.L. et al. (Aug. 1988). "Atrial Fibrillation and Stroke: New Ideas, Persisting Dilemmas," *Stroke* 19(8):937-941.
Halperin, J.L. et al. (Oct. 1, 2003). "Obliteration of the Left Atrial Appendage for Prevention of Thromboembolism," *J. of the American College of Cardiology* 42(7):1259-1261.
Hammill, S.C. (May 2006). "Epicardial Ablation: Reducing the Risks," *J. Cardiovasc. Electrophysiol.* 17:550-552.
Hara, H. et al. (Jan. 2008). "Percutaneous Left Atrial Appendage Obliteration," *JACC: Cardiovascular Imaging* 1(1):92-93.
Hart, R.G. et al. (Nov. 2, 1999). "Atrial Fibrillation and Thromboembolism: A Decade of Progress in Stroke Prevention," *Annals of Internal Medicine* 131(9):688-695.
Hart, R.G. et al. (2001). "Atrial Fibrillation and Stroke: Concepts and Controversies," *Stroke* 32:803-808.
Hart, R.G. (Sep. 11, 2003). "Atrial Fibrillation and Stroke Prevention," *The New England Journal of Medicine* 349(11):1015-1016.
Healey, J.S. et al. (Oct. 24-29, 2003). "Surgical Closure of the Left Atrial Appendage for the Prevention of Stroke: A Randomized Pilot Trial of Safety and Efficacy (The Left Atrial Appendage Occlusion Study—LAAOS)," presented at the Canadian Cardiovascular Congress 2003, Toronto, Canada, Abstract No. 666, 2 pages.
Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.
Hein, R. et al. (2005). "Patent Foramen Ovale and Left Atrial Appendage: New Devices and Methods for Closure," *Pediatric Cardiology* 26(3):234-240.
Heist, E.K. et al. (Nov. 2006). "Analysis of the Left Atrial Appendage by Magnetic Resonance Angiography in Patients with Atrial Fibrillation," *Heart Rhythm* 3(11):1313-1318.
Ho, I. et al. (Apr. 24, 2007). "Percutaneous Epicardial Mapping Ablation of a Posteroseptal Accessory Pathway," *Circulation* 115:e418-e421.
Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.
Hoit, B.D. et al. (Jan. 1993). "Altered Left Atrial Compliance After Atrial Appendectomy. Influence on Left Atrial and Ventricular Filling," *Circulation Research* 72(1):167-175.
Inoue, Y. et al. (Jul.-Aug. 1997). "Video Assisted Thoracoscopic and Cardioscopic Radiofrequency Maze Ablation," *Asaio Journal* 43(4):334-337, Abstract Only.
International Preliminary Report on Patentability mailed on Oct. 15, 2009, for PCT Application No. PCT/US2008/003938, filed on Mar. 25, 2008, 11 pages.
International Search Report mailed on Sep. 14, 2012, for PCT Patent Application No. PCT/US2012/41285, filed on Jun. 7, 2012, 2 pages.
International Search Report mailed on Feb. 27, 2007, for PCT Application No. PCT/US2008/003938, filed on Mar. 25, 2008, 5 pages.
International Search Report mailed on Jun. 1, 2010, for PCT Application No. PCT/US2010/029668, filed on Apr. 1, 2010, 2 pages.
Jaïs, P. et al. (2003). "Radiofrequency Ablation for Atrial Fibrillation," *European Society of Cardiology* 5(Supplement H):H34-H39.
Japanese Office Action mailed on Dec. 17, 2013, for Japanese Patent Application No. 2012-503714, filed on Apr. 1, 2010, 2 pages.
Johnson, W.D. et al. (2000). "The Left Atrial Appendage: Our Most Lethal Human Attachment! Surgical Implications," *Euro. J. Cardiothoracic. Surg.* 17:718-722.
Jongbloed, M.R.M. et al. (2005). "Clinical Applications of Intracardiac Echocardiography in Interventional Procedures," *Heart* 91:981-990.
Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.
Kanderian, A.S. et al. (2008). "Success of Surgical Left Atrial Appendage Closure: Assessment by Transesophageal Echocardiography," *Journal of the American College of Cardiology* 52(11):924-929.
Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.
Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.
Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.
Kerut, E.K. et al. (Jul. 2008). "Anatomy of the Left Atrial Appendage," *Echocardiography* 25(6):669-673.
Khargi, K. et al. (2005). "Surgical Treatment of Atrial Fibrillation: A Systematic Review," *European Journal of Cardiothoracic Surgery* 27:258-265.
Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.

(56) References Cited

OTHER PUBLICATIONS

Kistler, P.M. et al. (May 2007). "The Left Atrial Appendage: Not Just an Innocent Bystander," *J. Cardiovasc Electrophysiol* 18(5):465-466.
Klein, H. et al. (Apr. 1990). "The Implantable Automatic Cardioverter-Defibrillator," *Herz* 15(2):111-125, Abstract Only.
Kolb, C. et al. (Feb. 2004). "Incidence of Antitachycardia Therapy Suspension Due to Magnet Reversion in Implantable Cardioverter Defibrillators," *Pace* 27:221-223.
Krikorian, J.G. et al. (Nov. 1978). "Pericardiocentesis," *Am. J. Med.* 65(5):808-814.
Krum, D. et al. (2004). "Visualization of Remnants of the left Atrial Appendage Following Epicardial Surgical Removal," *Heart Rhythm* 1:249.
Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.
Lacomis, J.M. et al. (2007, e-pub. Oct. 17, 2007). "Dynamic Multi-dimensional Imaging of the Human Left Atrial Appendage," *Europace* 9:1134-1140.
Lee, R. et al. (1999). "The Closed Heart MAZE: A Nonbypass Surgical Technique," *The Annals of Thoracic Surgery* 67:1696-1702.
Levinson, M.L. et al. (1998). "Minimally Invasive Atrial Septal Defect Closure Using the Subxyphoid Approach," *Heart Surg. Forum* 1(1):49-53, Abstract Only.
Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.
Li, H. (2007). "Magnet Decoration, Beautiful But Potentially Dangerous for Patients with Implantable Pacemakers or Defibrillators," *Heart Rhythm* 4(1):5-6.
Lindsay, B.D. (1996). "Obliteration of the Left Atrial Appendage: A Concept Worth Testing," *The Annals of Thoracic Surgery* 61:515.
Lip, G.Y.H. et al. (Jun. 2001). "Thromboprophylaxis for Atrial Flutter," *European Heart Journal* 22(12):984-987.
Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.
Macris, M. et al. (Jan. 1999). "Minimally Invasive Access of the Normal Pericardium: Initial Clinical Experience with a Novel Device," *Clin. Cardiol.* 22(Suppl. I):I-36-I-39.
Maisch, B. et al. (Jan. 1999). "Intrapericardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.
Mannam, A.P. et al. (Apr. 1, 2002). "Safety of Subxyphoid Pericardial Access Using a Blunt-Tip Needle," *The American Journal of Cardiology* 89:891-893.
Mattox, K.L. et al. (May 1997). "Newer Diagnostic Measures and Emergency Management," *Chest Surg. Clin. N. Am.* 7(2):213-226, Abstract Only.
McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.
McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.
McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.
Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.
Miller, P.S.J. et al. (Feb. 2005). "Are Cost Benefits of Anticoagulation for Stroke Prevention in Atrial Fibrillation Underestimated?" *Stroke* 36:360-366.
Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.
Morris, J.J. Jr. (1979). "Transvenous versus Transthoracic Cardiac Pacing," Chapter 16 in *Cardiac Pacing: A Concise Guide to Clinical Practice*, pp. 239-245.
Mráz, T. et al. (Apr. 2007). "Role of Echocardiography in Percutaneous Occlusion of the left Atrial Appendage," *Echocardiography* 24(4):401-404.
Naclerio, E.A. et al. (1979). "Surgical Techniques for Permanent Ventricular Pacing," Chapter 10 in *Cardiac Pacing: A Concise Guide to Clinical Practice*, pp. 145-168.
Nakai, T. et al. (May 7, 2002). "Percutaneous Left Atrial Appendage Occlusion (PLAATO) for Preventing Cardioembolism: First Experience in Canine Model," *Circulation* 105:2217-2222.
Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.
Non-Final Office Action mailed on Mar. 13, 2008 for U.S. Appl. No. 10/963,371, filed Oct. 11, 2004, 13 pages.
Non-Final Office Action mailed on Aug. 6, 2008 for U.S. Appl. No. 10/963,371, filed Oct. 11, 2004, 14 pages.
Non-Final Office Action mailed on Jun. 26, 2009, for U.S. Appl. No. 11/600,671, filed Nov. 15, 2006, 9 pages.
Non-Final Office Action mailed on Dec. 30, 2009, for U.S. Appl. No. 11/400,714, filed Apr. 7, 2006, 8 pages.
Non-Final Office Action mailed on Jul. 22, 2010, for U.S. Appl. No. 12/037,802, filed Feb. 26, 2008, 10 pages.
Non-Final Office Action mailed on Nov. 15, 2010, for U.S. Appl. No. 12/055,213, filed Mar. 25, 2008, 18 pages.
Non-Final Office Action mailed on Feb. 17, 2011, for U.S. Appl. No. 12/212,511, filed Sep. 17, 2008, 14 pages.
Non-Final Office Action mailed on Apr. 28, 2011, for U.S. Appl. No. 12/055,213, filed Mar. 25, 2008, 20 pages.
Non-Final Office Action mailed on Oct. 27, 2011, for U.S. Appl. No. 12/363,359, filed Jan. 30, 2009, 11 pages.
Non-Final Office Action mailed on Nov. 9, 2011, for U.S. Appl. No. 12/363,381, filed Jan. 30, 2009, 10 pages.
Non-Final Office Action mailed on Dec. 22, 2011, for U.S. Appl. No. 13/033,532, filed Feb. 23, 2011, 8 pages.
Non-Final Office Action mailed on Mar. 7, 2012, for U.S. Appl. No. 12/124,023, filed May 20, 2008, 13 pages.
Non-Final Office Action mailed on Apr. 2, 2012, for U.S. Appl. No. 12/212,511, filed Sep. 17, 2008, 5 pages.
Non-Final Office Action mailed on Sep. 18, 2013, for U.S. Appl. No. 12/055,213, filed Mar. 25, 2008, 15 pages.
Non-Final Office Action mailed on May 31, 2013, for U.S. Appl. No. 12/124,023, filed May 20, 2008, 14 pages.
Non-Final Office Action mailed on Apr. 2, 2014, for U.S. Appl. No. 13/033,532, filed Feb. 23, 2011, 8 pages.
Non-Final Office Action mailed on Jun. 17, 2014, for U.S. Appl. No. 12/363,359, filed Jan. 30, 2009, 7 pages.
Notice of Allowance mailed on Sep. 17, 2010, for U.S. Appl. No. 10/963,371, filed Oct. 11, 2004, 7 pages.
Notice of Allowance mailed on Sep. 17, 2010, for U.S. Appl. No. 11/600,671, filed Nov. 15, 2006, 7 pages.
Notice of Allowance mailed on Nov. 24, 2010, for U.S. Appl. No. 11/400,714, filed Apr. 7, 2006, 8 pages.
Notice of Allowance mailed on Feb. 22, 2013, for U.S. Appl. No. 12/212,511, filed Sep. 17, 2008, 8 pages.
Notice of Allowance mailed on Mar. 18, 2013, for U.S. Appl. No. 12/212,511, filed Sep. 17, 2008, 6 pages.
Notice of Allowance mailed on Mar. 4, 2014, for U.S. Appl. No. 12/055,213, filed Mar. 25, 2008, 9 pages.
Notice of Allowance mailed on Apr. 1, 2014, for U.S. Appl. No. 12/363,381, filed Jan. 30, 2009, 9 pages.
Notice of Allowance mailed on Apr. 3, 2014, for U.S. Appl. No. 12/037,802, filed Feb. 26, 2008, 8 pages.
Notice of Allowance mailed on Feb. 18, 2014, for Australian Patent Application No. 2008233242, filed on Mar. 25, 2008, 2 pages.

(56) References Cited

OTHER PUBLICATIONS

Odell, J.A. et al. (1996). "Thoracoscopic Obliteration of the Left Atrial Appendage: Potential for Stroke Reduction?" *Ann. Thorac. Surg.* 61:565-569.

O'Donnell, M. et al. (2005). "Emerging Therapies for Stroke Prevention in Atrial Fibrillation," *European Heart Journal* 7(Supplement C):C19-C27.

Omran, H. et al. (1997). "Left Atrial Appendage Function in Patients with Atrial Flutter," *Heart* 78:250-254.

Onalan, O. et al. (2005). "Nonpharmacologic Stroke Prevention in Atrial Fibrillation," *Expert Rev. Cardiovasc. Ther.* 3(4):619-633.

Onalan, O. et al. (2007). "Left Atrial Appendage Exclusion for Stroke Prevention in Patients With Nonrheumatic Atrial Fibrillation," *Stroke* 38(part 2):624-630.

Ostermayer, S. et al. (2003). "Percutaneous Closure of the Left Atrial Appendage," *Journal of Interventional Cardiology* 16(6):553-556.

Ota, T. et al. (2006). "Epicardial Atrial Ablation Using a Novel Articulated Robotic Medical Probe via a Percutaneous Subxiphoid Approach," *Innovations Phila. Pa.* 1(6):335-340.

Ota, T. et al. (Oct. 2007). "Impact of Beating Heart left Atrial Ablation on Left-sided Heart Mechanics," *The Journal of Thoracic and Cardiovascular Surgery* 134:982-988.

Pennec, P-Y. et al. (2003). "Assessment of Different Procedures for Surgical Left Atrial Appendage Exclusion," *The Annals of Thoracic Surgery* 76:2167-2169.

Perk, G. et al. (Aug. 2009). "Use of Real Time Three-Dimensional Transesophageal Echocardiography in Intracardiac Catheter Based Interventions," *J. Am Soc Echocardiogr* 22(8):865-882.

Pollick, C. (Feb. 2000). "Left Atrial Appendage Myopathy," *Chest* 117(2):297-308.

Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.

Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.

Robicsek, F. (1987). "Closed-Chest Decannulation of Transthoracically Inserted Aortic Balloon Catheter without Grafting," *Journal of Cardiac Surgery* 2(2):327-329.

Ross, J. Jr. et al. (Jun. 3, 2008). "Transseptal Left Heart Catheterization: A 50-Year Odyssey," *Journal of the American College of Cardiology* 51(22):2107-2115.

Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.

Ruchat, P. et al. (2002). "Off-pump Epicardial Compartmentalization for Ablation of Atrial Fibrillation," *Interactive Cardio Vascular and Thoracic Surgery* 1:55-57.

Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.

Sapp, J. et al. (Dec. 2001). "Electrophysiology and Anatomic Characterization of an Epicardial Accessory Pathway," *J. of Cardiovascular Electrophysiology* 12(12):1411-1414.

Scharf, C. et al. (2005). "Catheter Ablation for Atrial Fibrillation: Pathophysiology, Techniques, Results and Current Indications," *Continuous Medical Education* 8:53-61.

Scherr, D. et al. (Apr. 2009). "Incidence and Predictors of left Atrial Thrombus Prior to Catheter Ablation of Atrial Fibrillation," *J. of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

Schneider, B. et al. (2005, e-pub. Aug. 22, 2005). "Surgical Closure of the Left Atrial Appendage—A Beneficial Procedure?" *Cardiology* 104:127-132.

Schweikert, R.A. et al. (Sep. 16, 2003). "Percutaneous Pericardial Instrumentation for Endo-Epicardial Mapping of Previously Failed Ablations," *Circulation* 108:1329-1335.

Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.

Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.

Sengupta, P.P. et al. (2005). "Transoesophageal Echocardiography," *Heart* 91:541-547.

Sharada, K. et al. (2005). "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (1996). "A New Technique to Perform Epicardial Mapping in the Electrophysiology Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Sosa, E. et al. (Jul. 15, 2002). "Gaining Access to the Pericardial Space," *The American Journal of Cardiology* 90:203-204.

Sosa, E. et al. (Apr. 2005). "Epicardial Mapping and Ablation Techniques to Control Ventricular Tachycardia," *Journal of Cardiovasc. Electrophysiol.* 16(4):449-452.

Sparks, P.B. et al. (2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.

Stewart, S. (1974). "Placement of the Sutureless Epicardial Pacemaker Lead by the Subxiphoid Approach," *Ann. of Thoracic Surg.* 18(3):308-313.

Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.

Stokes, K. (Jun. 1990). "Implantable Pacing Lead Technology," *IEEE Engineering in Medicine and Biology* pp. 43-49.

Stöllberger, C. et al. (2000). "Is the Left Atrial Appendage Our Most Lethal Attachment?" *European Journal of Cardio-Thoracic Surgery* 18:625-626.

Stöllberger, C. et al. (Dec. 2003). "Elimination of the Left Atrial Appendage to Prevent Stroke or Embolism?: Anatomic, Physiologic, and Pathophysiologic Considerations," *Chest* 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.

Stöllberger, C. et al. (2007). "Arguments Against Left Atrial Appendage Occlusion for Stroke Prevention," *Stroke* 38:e77.

Stöllberger, C. et al. (2007). "Leave the Left Atrial Appendage Untouched for Stroke Prevention!" *Journal of Thoracic and Cardiovascular Surgery* 134(2):549-550.

(56) References Cited

OTHER PUBLICATIONS

Su, P. et al. (Sep. 2008, e-pub. May 8, 2007). "Occluding the Left Atrial Appendage: Anatomical Considerations," *Heart* 94(9):1166-1170.

Subramanian, V.A. (Jun. 1997). "Less Invasive Arterial CABG on a Beating Heart," *Ann. Thorac. Surg.* 63(6 Suppl.):S68-S71.

Subramanian, V.A. et al. (Dec. 1997). "Minimally Invasive Direct Coronary Artery Bypass Grafting: Two-Year Clinical Experience," *Ann. Thorac. Surg.* 64(6):1648-1653, Abstract Only.

Suehiro, S. et al. (1996). "Echocardiography-Guided Pericardiocentesis With a Needle Attached to a Probe," *Ann. Thoracic Surg.* 61:741-742.

Sun, F. et al. (Feb. 2006). "Subxiphoid Access to Normal Pericardium with Micropuncture Set: Technical Feasibility Study in Pigs," *Radiology* 238(2):719-724.

Szili-Torok, T. et al. (2001). "Transseptal Left heart Catheterisation Guided by Intracardiac Echocardiography," *Heart* 86:e11-e15.

Tabata, T. et al. (Feb. 1, 1998). "Role of Left Atrial Appendage in Left Atrial Reservoir Function as Evaluated by Left Atrial Appendage Clamping During Cardiac Surgery," *The American Journal of Cardiology* 81:327-332.

Tomar, M. et al. (Jul.-Aug. 2006). "Transcatheter Closure of Fossa Ovalis Atrial Septal Defect: A Single Institutional Experience," *Indian Heart Journal* 58(4):325-329.

Troughton, R.W. et al. (Feb. 28, 2004). "Pericarditis," *The Lancet* 363:717-727.

Ulicny K.S. et al. (Jun. 1992). "Conjoined Subrectus Pocket for Permanent Pacemaker Placement in the Neonate," *Ann Thorac Surg.* 53(6):1130-1131, Abstract Only.

Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.

Von Korn, H. et al. (2006). "Simultaneous Combined Interventional Percutaneous Left Atrial Auricle and Atrial Septal Defect Closure," *Heart* 92:1462.

Wang, T.J. et al. (Aug. 27, 2003). "A Risk Score for Predicting Stroke or Death in Individuals With New-Onset Atrial Fibrillation in the Community," *JAMA* 290(8):1049-1056.

Watkins, L. et al. (Nov. 1982). "Implantation of the Automatic Defibrillator: The Subxiphoid Approach," *Ann. of Thoracic Surg.* 34(5):515-520.

W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.

Wolber, T. et al. (Jan. 2007). "Potential Interference of Small Neodymium Magnets with Cardiac pacemakers and Implantable Cardioverter-defibrillators," *Heart Rhythm* 4(1):1-4.

Wolf, P.A. et al. (Oct. 1978). "Epidemiologic Assessment of Chronic Atrial Fibrillation and Risk of Stroke: The Fiamingham Study," *Neurology* 28:973-977.

Wolf, P.A. et al. (Aug. 1991). "Atrial Fibrillation as an Independent Risk Factor for Stroke: The Framingham Study," *Stroke* 22(8):983-988.

Wolf, P.A. et al. (Feb. 9, 1998). "Impact of Atrial Fibrillation on Mortality, Stroke, and Medical Costs," *Arch. Intern. Med.* 158:229-234.

Wong, J.W.W. et al. (2006). "Impact of Maze and Concomitant Mitral Valve Surgery on Clinical Outcomes," *The Annals of Thoracic Surgery* 82:1938-1947.

Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.

Wood, M.A. (Jan. 2006). "Percutaneous Pericardial Instrumentation in the Electrophysiology Laboratory: A Case of Need," *Heart Rhythm* 3(1):11-12.

Written Opinion from the International Searching Authority mailed on Sep. 14, 2012, for PCT Patent Application No. PCT/US2012/41285, filed on Jun. 7, 2012, 6 pages.

Written Opinion of the International Searching Authority mailed on Feb. 27, 2007, for PCT Application No. PCT/US2008/003938, filed on Mar. 25, 2008, 10 pages.

Written Opinion of the International Searching Authority mailed on Jun. 1, 2010, for PCT Application No. PCT/US2010/029668, filed on Apr. 1, 2010, 8 pages.

Wudel, J.H. et al. (Apr. 3, 2008). "Video-Assisted Epicardial Ablation and Left Atrial Appendage Exclusion for Atrial Fibrillation: Extended Follow-Up," *The Annals of Thoracic Surgery* 85:34-38.

Wyse, D.G. et al. (Dec. 5, 2002). "Of 'Left Atrial Appendage Amputation, Ligation, or Occlusion in Patients with Atrial Fibrillation'," *N. Engl. J. Med.* 347(23):1825-1833, Abstract Only.

Yamada, Y. et al. (Aug. 2006). "Video-Assisted Thoracoscopy to Treat Atrial Tachycardia Arising from Left Atrial Appendage," *J. of Cardiovascular Electrophysiology* 17(8):895-898.

Zapolanski, A. et al. (May 2008). "Safe and Complete Exclusion of the left Atrial Appendage, A Simple Epicardial Approach," *Innovations* 3(3):161-163.

Zenati, M.A. et al. (Sep. 2003). "Left Heart Pacing Lead Implantation Using Subxiphoid Videopericardioscopy," *Journal of Cardiovascular Electrophysiology* 14(9):949-953.

Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.

Zenati, M.A. et al. (2005). "Modification of the Left Atrial Appendage," Chapter 12 in *Innovative Management of Atrial Fibrillation*, Schwartzman, David ed., Blackwell Science Ltd., pp. 152-156.

\* cited by examiner

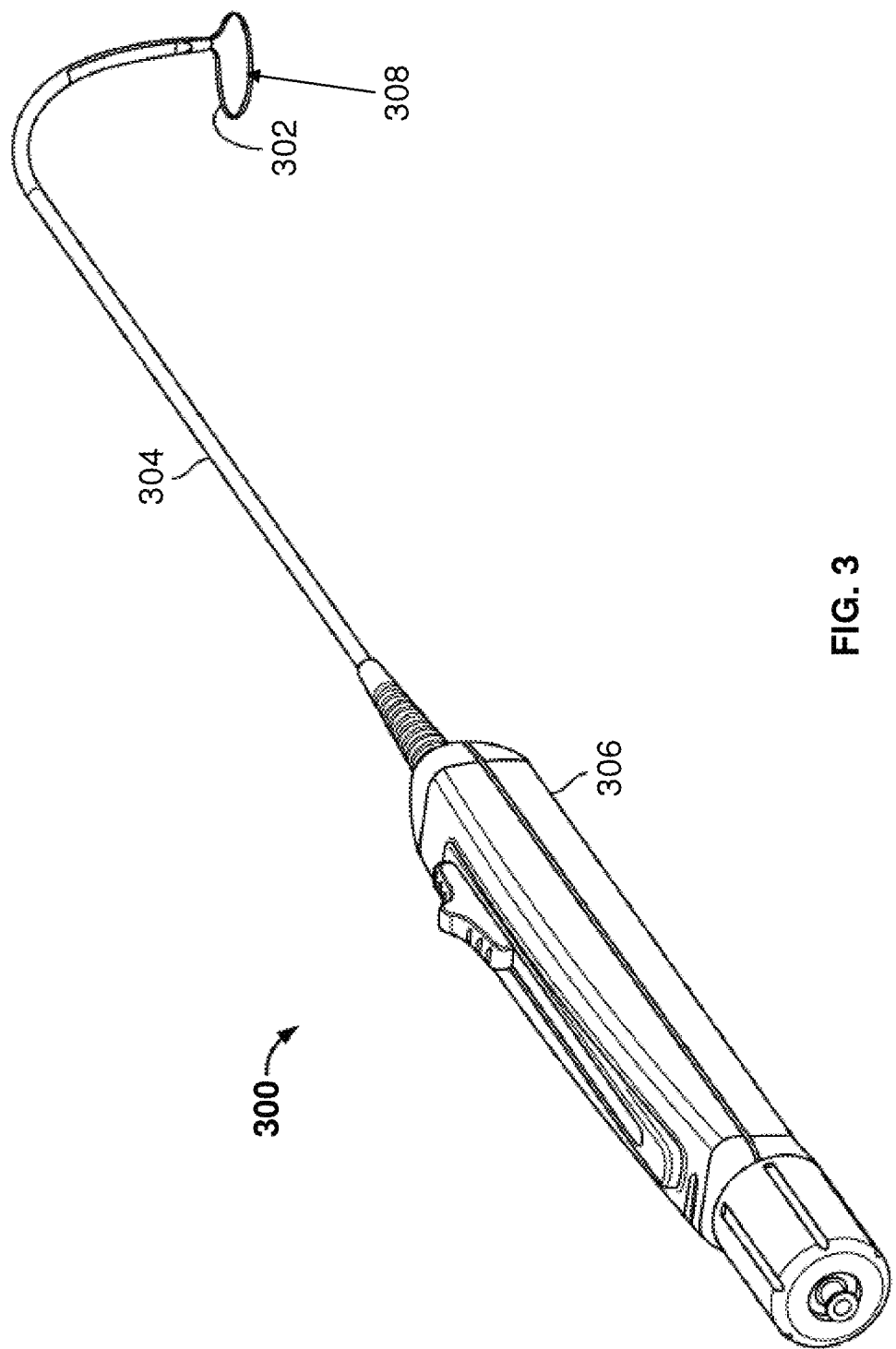

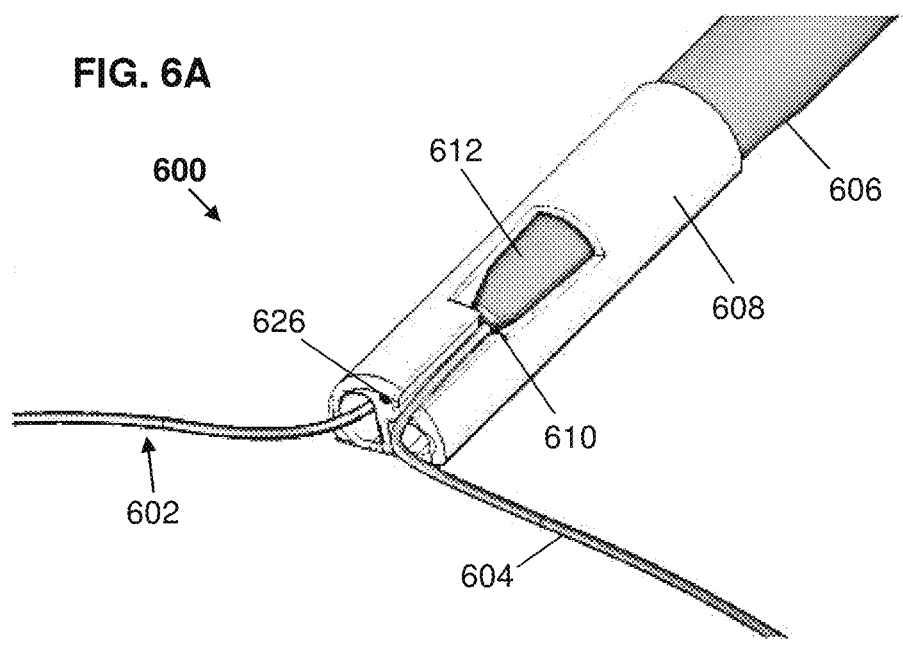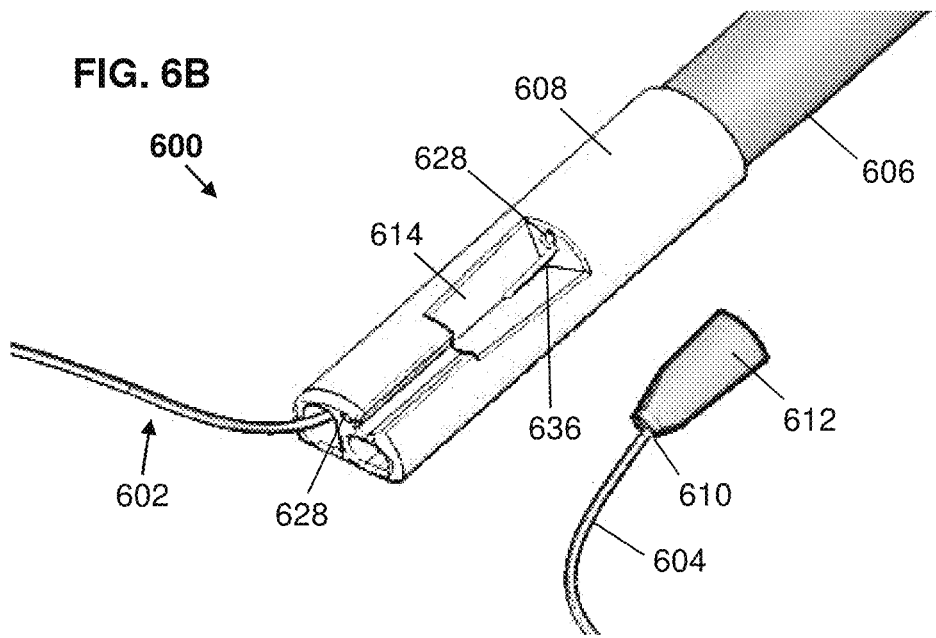

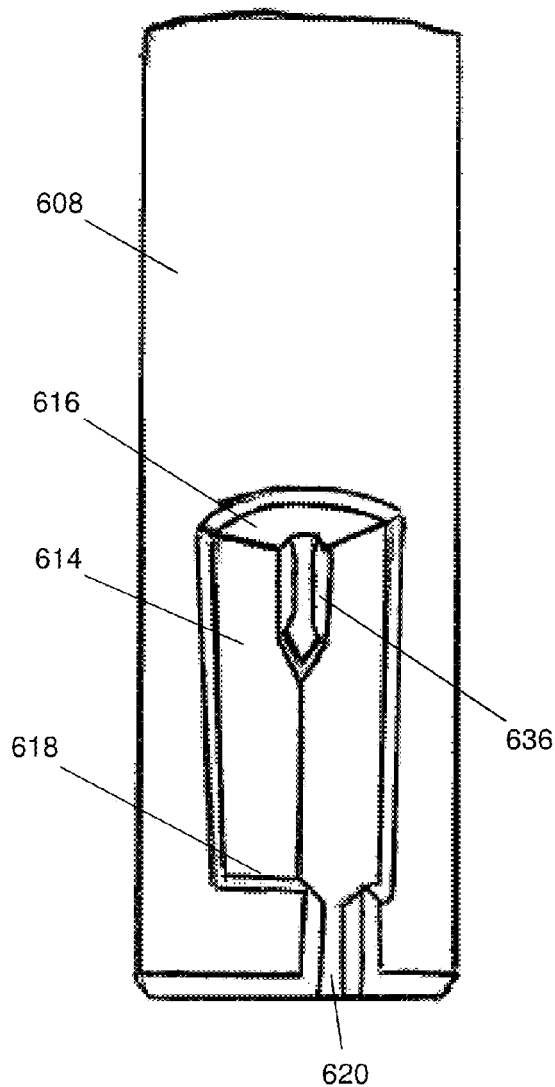
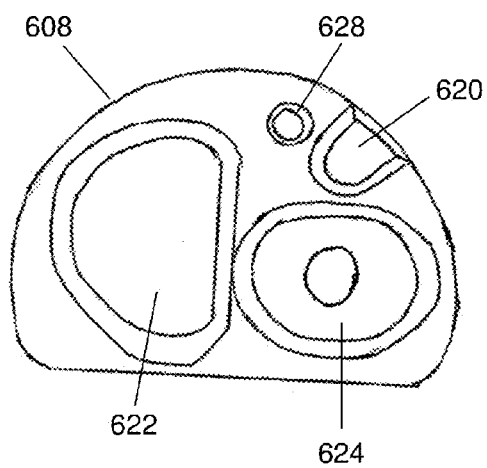

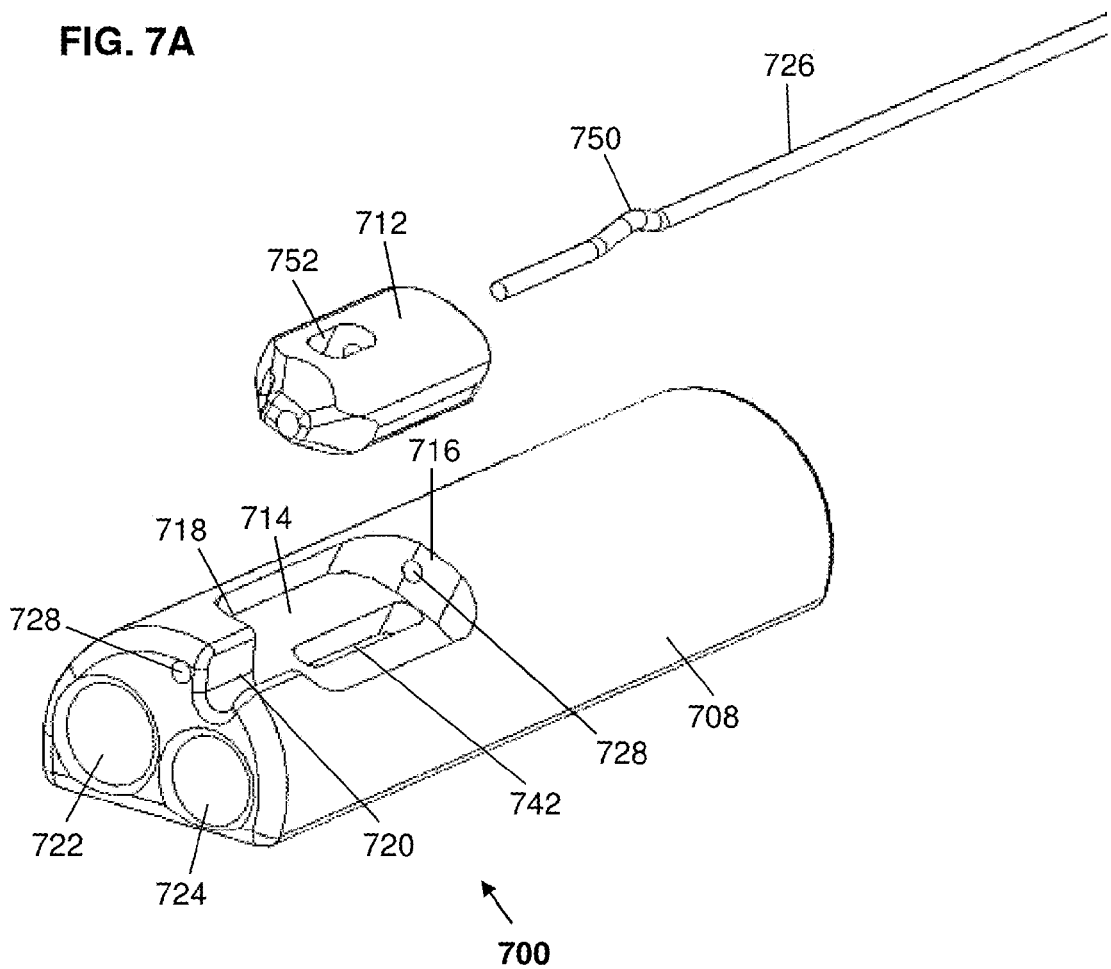

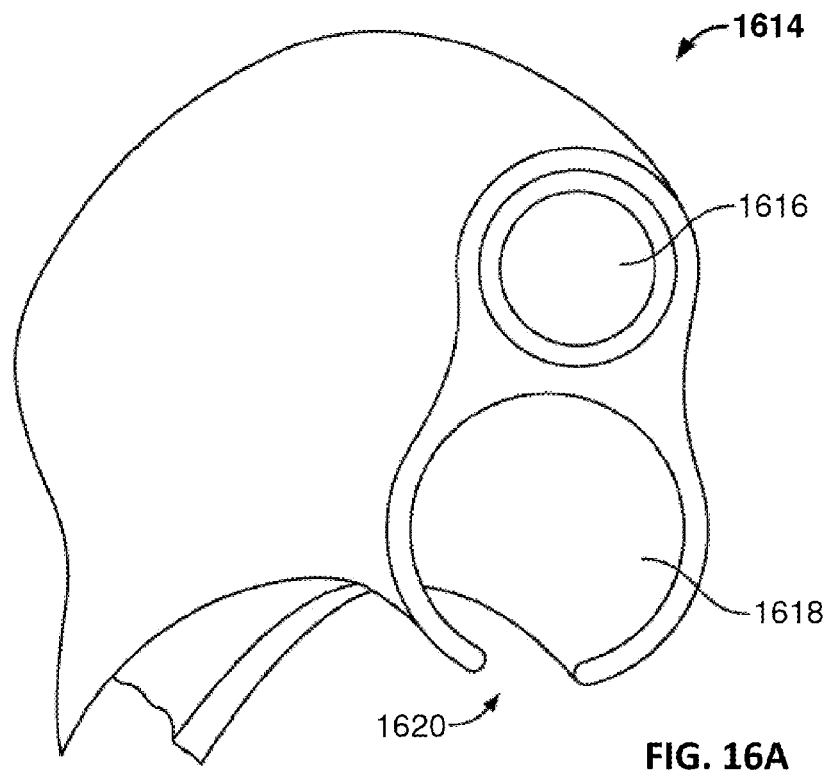
FIG. 16A
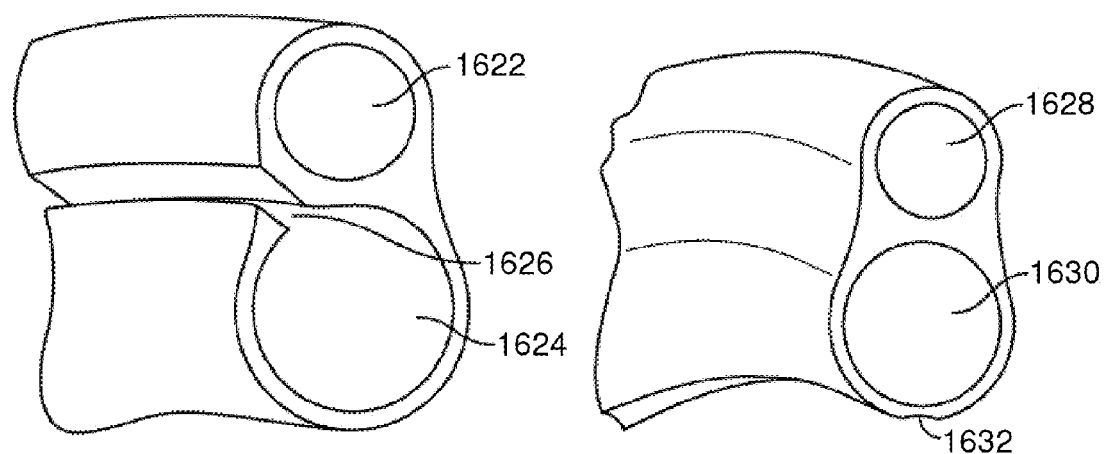
FIG. 16B
FIG. 16C

TISSUE LIGATION DEVICES AND METHODS THEREFOR

CROSS-REFERENCE TO RELATED APPLICATIONS

This application claims priority to U.S. Provisional Patent Application Ser. No. 61/778,251, filed on Mar. 12, 2013 and titled "TISSUE LIGATION DEVICES AND METHODS THEREFOR", which is incorporated by reference herein in its entirety.

FIELD

This invention relates generally to devices and methods for ligating tissue, such as the left atrial appendage, using surgically, minimally invasive or intravascular approaches.

BACKGROUND

Atrial fibrillation is a common problem that afflicts millions of patients. Atrial fibrillation often results in the formation of a thrombus, or clot, in the appendage of the left atrium. This presents a problem, inasmuch as the thrombus can dislodge and embolize to distant organs, which may result in adverse events such as a stroke. For this reason, most patients with atrial fibrillation are treated with one or more blood thinners to help prevent the formation of a thrombus. Blood thinners, however, can present health risks of their own, especially in the elderly. These risks, such as bleeding, often require a user to make significant lifestyle changes.

Several methods have been developed to address the potential problem of thrombus formation in the left atrial appendage. One such method includes suturing the left atrial appendage along the base or ostial neck where it joins the atrial chamber. In this way, blood flow into the atrial appendage is cut off, eliminating the risk of thrombus formation therein. This is typically done through open-heart surgery, which limits the availability of the procedure to those who are at a particularly high risk, or who are otherwise undergoing an open-heart procedure. In addition, open-heart surgery requires general anesthesia and has a number of well-known risks, making it less desirable.

Other methods have also been investigated. These methods include methods of stapling the base of the appendage and methods of filling the appendage with a space occupying or occluding member. Stapling is not preferred given the fragility of the appendage and its tendency to rupture, while occlusion devices may not effectively prevent all blood flow into the appendage.

Additional devices and methods for closing the left atrial appendage or other suitable tissues would therefore be desirable. In particular, devices and methods for closing the left atrial appendage using minimally invasive, intravascular, or a combination of these techniques, would be desirable in order to avoid the need for opening the chest. Of course, additional devices for use in open surgical procedures are desirable as well, especially when those devices offer additional advantages over standard devices.

BRIEF SUMMARY

Described here are closure devices and methods for closing tissues using one or more closure devices. In some variations, a closure device may comprise an elongate body and a snare sloop assembly extending at least partially from the elongate body and forming a loop. The snare loop assembly may comprise a snare and a suture loop releasably attached to the snare. The snare may comprise a first end and a second end, such that advancement of the first end of the snare relative to the elongate body increases the diameter of the loop and retraction of the first end of the snare relative to the elongate body decreases the diameter of the loop. The closure devices may further comprise a shuttle, such that the second end of the snare is connected to the shuttle, and a locking element configured to releasably couple the shuttle to the elongate body. The locking element may be further configured to release the shuttle from the elongate body. In some variations, the elongate body may comprise a recess in a side wall of the elongate body, and the shuttle may be positioned in the recess when the shuttle is releasably coupled to the elongate body. In some variations, the locking element may comprise a lock wire. In some of these variations, the lock wire may extend through a lock wire lumen of the elongate body and a lock lumen of the shuttle when the shuttle is releasably coupled to the elongate body. In some of these variations, the lock wire may comprise a bend. In some of these variations, the bend may extend at least partially into a window of the shuttle when the shuttle is releasably coupled to the elongate body.

In some variations, the shuttle may comprise a projection configured to fit within a channel within the recess of the elongate body. The projection may be configured to resist rotation between the shuttle and the elongate body. In other variations, the recess of the elongate body may comprise a projection configured to fit within a channel of the shuttle and configured to resist rotation between the shuttle and the elongate body.

In some variations, the closure devices described here may further comprise a handle attached to the elongate body. In some of these variations, the handle may comprise a suture control for tightening the suture loop, a snare control to control movement of the first end of the snare, and a snare release configured to release the shuttle from the elongate body. In variations where the locking element comprises a lock wire, the snare release may be configured to retract the lock wire. In some variations, the snare release may comprise a button configured to release the shuttle upon depression of the button. In some of these variations, the suture control may comprise a grip portion and a prong extending therefrom. The prong may be sized and configured to depress the button of the snare release. In other variations, the suture control may comprise a grip portion and a chamber in the grip portion. The chamber may be configured to at least partially enclose the snare release.

In other variations of the devices described here, the closure device may comprise an elongate body and a snare loop assembly extending at least partially from the elongate body and forming a loop. The snare loop assembly may comprise a snare and a suture loop releasably attached to the snare. The snare may comprise a proximal snare portion and a distal snare portion, each comprising an engagement portion. The engagement portion of the proximal snare portion may be configured to releasably engage the engagement portion of the distal snare portion. The snare loop assembly may further comprise a restraining sheath positioned to maintain engagement of the proximal and distal snare portions. In some of these variations, the engagement portion of the distal snare portion may comprise a first hook member and the engagement portion of the proximal snare portion may comprise a second hook member. In other variations, the engagement portion of the distal snare portion may comprise a slug and the engagement portion of the proximal snare portion may comprise a cup member. In other variations, the engagement portion of the distal snare portion may comprise a cup member and the engagement portion of the proximal snare portion may comprise a slug.

In some variations the closure device may comprise a handle. The handle may comprise a snare control. In some of these variations, the snare control may comprise a first control operatively connected to the proximal snare portion and a second control operatively connected the restraining sheath. In some of these variations, the first and second controls may be configured to be moved together to simultaneously advance or retract the proximal snare portion and the restraining sheath. The first and second controls may also be configured such that proximal movement of the second control relative to the first control withdraws the restraining sheath relative to the proximal snare portion to disengage the proximal snare portion and distal snare portion. In some variations, the snare control further may further comprise a removable cover configured to couple the first control and the second control. In some of these variations, the removable cover may comprise one or more magnets which engage a magnet of the first and/or second controls.

BRIEF DESCRIPTION OF THE DRAWINGS

FIG. 3 is a perspective view of an illustrative closure device as described here.

FIGS. 6A and 6B depict perspective views of a variation of a closure device having a releasable snare. FIGS. 6C and 6D show a top view and a front view, respectively, of a tip of the closure device shown in FIGS. 6A and 6B.

FIG. 7A shows a perspective view of a distal portion of a closure device having a releasable snare.

FIGS. 16A-16C depict illustrative retention members that may be used with the devices described here.

DETAILED DESCRIPTION

Figure 1:
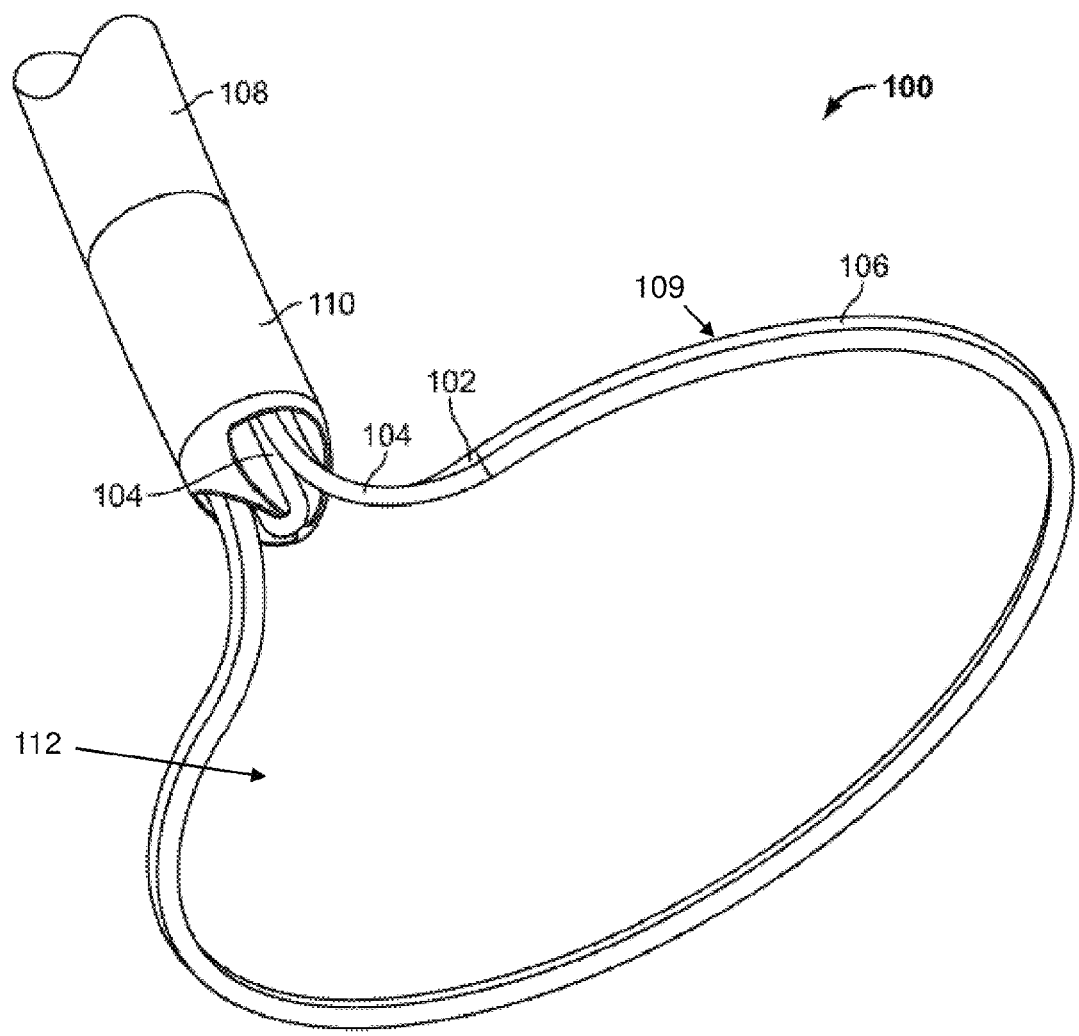
FIG. 1 is a view of a distal end of an illustrative device having a snare loop assembly.

Described here are closure devices and methods for closing tissues using one or more closure devices. Generally, the closure devices comprise an elongate body and a snare loop assembly that may extend at least partially from the elongate body to capture and hold tissue. The snare loop assembly typically comprises a snare and a suture loop releasably coupled to the snare. The snare loop assembly may be closed around tissue to temporarily or permanently close, ligate, or otherwise tighten tissue, and the suture loop may be tightened and released from the snare to hold or otherwise maintain the tissue in the closed configuration.

The closure devices described here may be suitable for advancement to the left atrial appendage using minimally invasive access (e.g., through a small incision above, beneath or through the rib cage, through an incision in the costal cartilage or the xiphoid, through a port, through the vasculature, etc.). When the closure devices are advanced using minimally invasive access through confined body spaces, such as the pericardial space, advancement or manipulation of the snare loop assembly within or through these tight spaces may result in twisting of one or more portions of the snare loop assembly. Accordingly, it may be desirable to configure the closure devices described here to allow a user to determine whether the snare loop assembly has become twisted. For example, in some variations (as will be described in more detail below), the closure device may comprise one or more markers which may allow a user to determine (e.g., via direct or indirect visualization) whether the snare loop assembly has become twisted.

Additionally, in some instances, one or more portions of the snare loop assembly may become caught on or otherwise stuck around one or more tissue structures during advancement or manipulation of the snare loop assembly. In order to remove the closure device from the body without necessitating an open surgical procedure, it may be useful to configure the closure device such that one or more portions of the snare loop assembly may be released relative to the rest of the closure device. For example, in some variations the closure devices may be configured to have a releasable snare, as will be described in more detail below.

The closure devices described here may include any suitable elements or combinations of elements such as those described in U.S. patent application Ser. No. 13/490,919, entitled "Tissue Ligation Devices and Tensioning Devices Therefor" and filed on Jun. 7, 2012, the contents of which is incorporated by reference herein in its entirety. In addition to having an elongate body and a snare loop assembly, the closure devices typically comprise one or more mechanisms for controlling manipulation and advancement of the elongate body and/or snare loop assembly. For example, a handle or other control mechanism (e.g., a surgical master-slave robotic system) may be used to control and actuate the snare loop assembly through the elongate body. The handle or other control mechanism may change the snare loop assembly between a delivery, or "closed," configuration and a deployed, or "open," configuration, and vice versa, as will be described in more detail below. Placing the snare loop assembly in a closed configuration may allow for low-profile advancement of the snare loop assembly to a target location, or may allow the snare loop assembly to close around a target tissue. Conversely, placing a snare loop assembly in an open configuration may allow the snare loop assembly to be placed around one or more target tissues, or may allow the snare loop assembly to release one or more target tissues previously closed by the snare loop assembly. The handle or other control mechanism may control release of the suture loop from the snare, as will be described in more detail below.

In use, a distal end of an elongate body may be advanced into the body toward a target tissue (e.g., the left atrial appendage). This advancement may be done in a minimally invasive manner. During advancement, the snare loop assembly may be in a closed configuration to help prevent the snare loop assembly from snagging or catching on tissue or other obstructions. Once the distal end of the elongate body has reached a location at or near the target tissue, the snare loop assembly may be opened to a deployed configuration. The snare loop assembly may then be advanced, moved, or otherwise manipulated to encircle at least a portion of the target tissue. The snare loop assembly may then be closed around the encircled tissue to close, ligate, or otherwise restrict the target tissue. The snare loop assembly may be re-opened, repositioned, and re-closed as necessary. In some instances, a suture loop (not shown) or other restricting device may be tightened and released from the closure device to maintain the target tissue in a closed fashion. To remove the closure device from the body, the snare loop assembly may again be opened to release the target tissue (it should be appreciated that the suture loop or other closure device may remain in place) such that the snare loop assembly and elongate body may be withdrawn. Once the target tissue is released, the snare loop assembly may be closed to facilitate low-profile withdrawal. In variations where the closure device comprises a tensioning device or mechanism, the tensioning device or mechanism may be used to release the suture loop from the snare loop assembly and/or tighten the suture loop, as will be described in more detail below.

FIG. 3 depicts one illustrative variation of closure device (300). Shown there are a snare loop assembly (302), an elongate body (304), and a handle (306). As noted above, the handle (306) may be used to control and actuate the snare loop assembly (302) through the elongate body (304) in order to move snare loop assembly (302) between a closed configuration (as shown in FIG. 3) and an open deployed configuration (not shown), and vice versa. When in an open configuration, the snare loop assembly (302) and elongate body (304) may form a continuous loop (308) (e.g., such that the snare loop assembly (302) and the elongate body (304) may fully encircle tissue placed in the loop (308)). When moved from the open configuration to the closed configuration, the size of the loop (308) may be reduced as some or all of the snare loop assembly (306) is withdrawn into the elongate body (304). Individual components of the closure devices described here will be described in more detail below.

Elongate Body

As mentioned briefly above, the closure devices described here generally comprise an elongate body. The elongate body may connect the distal end of the snare loop assembly and the handle or actuating mechanism while still allowing for control of the snare loop assembly through the elongate body. Specifically, at least a portion of some of the snare loop assembly components may be housed within the elongate body, and may be connected to the handle through the elongate body. In some variations, at least a portion of the elongate body may be flexible, which may help facilitate navigation of the elongate body in and through tissue.

Figure 14:
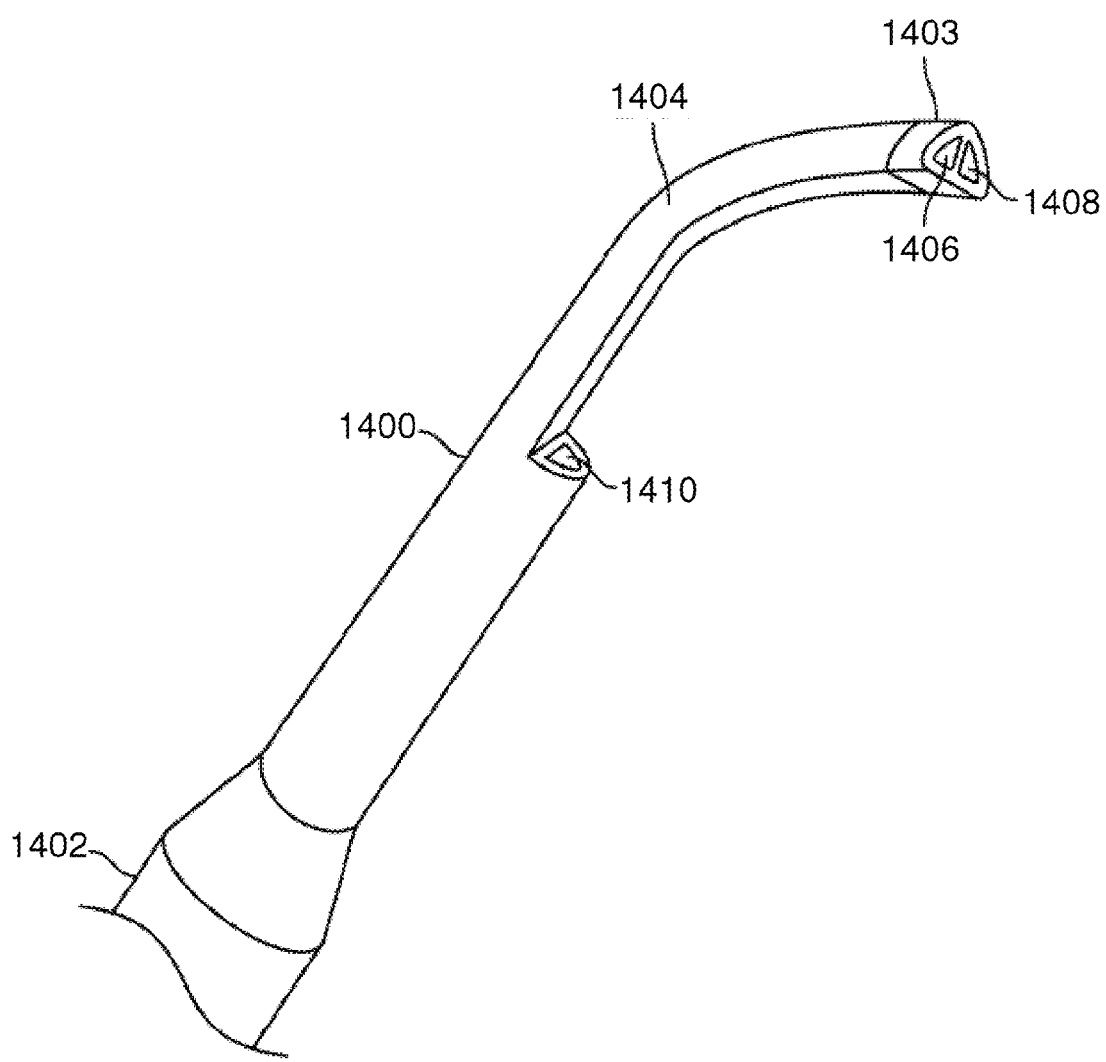
FIG. 14 depicts an illustrative variation of an elongate body suitable for use with the devices described here.

FIG. 14 shows one illustrative variation of an elongate body suitable for use with the closure devices described here. Shown there is elongate body (1400) attached to handle portion (1402). Elongate body (1400) may comprise tip (1403), a curved segment (1404), a first lumen (1406), a second lumen (1408), and a third lumen (1410). While shown in FIG. 14 as having a single curved section (1404), elongate body (1400) may have no curved sections or may have multiple curved sections in different portions of the elongate body (1400). Furthermore, in some variations the closure device may comprise one or more mechanisms that may act or function to change the shape of the elongate body (1400). In instances where the elongate body (1400) comprises one or more curves (1404), a tube, mandrel or other straightening mechanism (not shown) may be used to temporarily straighten the elongate body. For example, a rigid tube or mandrel may be placed in one or more lumens of elongate body (1400), which may temporarily straighten any curved sections. Straightening may occur during delivery (e.g., when used in conjunction with a left atrial appendage ligation procedure, before the pericardial space is reached), and the straightening mechanism may be withdrawn at any point to allow elongate body (1400) to return to its original configuration. The straightening mechanism may be made of any suitable material (e.g., a rigid plastic, stainless steel, a combination thereof, etc.).

In other variations, one or more pre-curved tubes or mandrels may be inserted into elongate body (1400) to create one or more curved sections. In still other variations, one or more pull wires may be disposed in, on, or around elongate body (1400) and may cause elongate body (1400) to flex or bend when one or more of the pull wires is pulled, pushed or otherwise manipulated. It should be further understood that any of the devices described here may be configured for steerability, or may be configured for robotic use (e.g., configured for use with one or more robotic or otherwise automated devices).

The elongate bodies described here may have any suitable number of lumens. It should be appreciated that when the term "lumen" is used herein, it may be used to describe any bore or passageway extending through a length of the elongate body or other portion of the closure device. It should be appreciated that a lumen need not be entirely enclosed (i.e., the lumen may comprise one or more slots, slits, gaps or other openings along some or all of the length of the lumen). The elongate body may comprise one, two, three, four, or five or more lumens. Some or all of the lumens may extend entirely through the elongate body (i.e., from the proximal end of the elongate body to the distal end of the elongate body). Other lumens may pass through only a portion of the elongate body (e.g., from one end to an intermediate point along the elongate body, or between two intermediate points along the elongate body). For example, in the variation shown in FIG. 14, third lumen (1410) passes from the proximal end of the elongate body (1400) to an intermediate point along the length of the elongate body (1400), while the first (1406) and second (1408) lumens may extend from the tip (1403) through the length of the elongate body (1400). In this variation, one or more guidewires, visualization devices, or working devices (not shown) may be passed through third lumen (1410).

The various components of the snare loop assembly may be housed within any lumen or lumens of the elongate body. For example, in some variations, all components of the snare loop assembly may be housed in a single lumen. In other variations, different portions of the snare loop assembly may be at least partially housed in different lumens. For example, in some variations, the elongate body may comprise at least two lumens. In these variations, the free end of suture loop may pass to the handle portion through a first lumen, while the free end of the snare may pass to the handle portion through a second lumen. In variations where the suture loop has excess suture housed within the elongate body, as described in more detail below, this excess suture may be housed in any suitable lumen. For example, in some variations, the excess suture may be held in the same lumen as the free end of the suture loop, in the same lumen as the free end of the snare, or in an altogether different lumen.

In some instances, one or more of the lumens of the elongate body may be at least partially divided into one or more sub-lumens. Specifically, a lumen may be split into two or more sub-lumens along a portion of the length of that lumen, such as described in U.S. patent application Ser. No. 13/490,919, which was previously incorporated by reference.

The elongate body generally comprises a tip portion at the distal end thereof. In some variations, the tip of the elongate body may be formed separately from the elongate body, and may be attached to the body during assembly of the device. In other variations the tip portion may be formed integrally with the elongate body as a unitary device. The tip portion may serve a number of useful functions for the closure device. In some instances, the tip may be configured to be atraumatic, which may act to reduce the risk of damaging tissue as the proximal end of the elongate body is moved within the body. In other instances, the tip may allow certain portions of the snare to pass through elongate body while holding other portions in place relative to elongate body, as will be described in more detail below.

The tip portion may have the same number of lumens as the elongate body, but need not. Indeed, in some variations, the tip portion may divide one or more lumens of the elongate body into two or more sub-lumens. In other variations, the tip portion may alter the size or shape of one or more lumens of the elongate body.

Snare Loop Assembly

As mentioned above, the snare loop assemblies of the closure devices described here may be used to temporarily close or restrict one or more target tissues. Generally the snare loop assembly comprises a snare and a suture loop releasably attached to the snare. In some variations, the snare loop assembly may comprise a retention member at least temporarily connecting the snare and the suture loop. FIG. 1 shows a distal portion of an illustrative variation of a closure device (101) comprising a snare loop assembly (100) and an elongate body (108) having tip (110). As shown there, the snare loop assembly (100) may comprise a snare (102), a suture loop (104), and a retention member (106), and may be disposed relative to the elongate body (108) such that at least a portion of the snare loop assembly (100) extends from the elongate body (108) (e.g., via tip (110)). The snare loop assembly (100) is shown in FIG. 1 in an open configuration, and the portion of snare loop assembly (100) extending out of elongate body (104) may form a loop (109) having an aperture (112) therethrough. The loop (109) and corresponding aperture (112) may be defined by one or more components of the snare loop assembly (100) (e.g., the snare), and may be suitable for encircling tissue such as the left atrial appendage. Generally, the snare (102) may be used to open and close the snare loop assembly (100), as will be described in more detail below. In some instances, the retention member (106) may be configured to releasably couple suture loop (104) and snare (102), and may be configured to release suture loop (104) from snare loop assembly (100) upon application of sufficient force to suture loop (104).

In variations of snare loop assemblies comprising a snare, the snare may be at least partially moveable to change a snare loop assembly between open and closed configurations. Generally, a portion of the snare may be housed in the elongate body, and another portion of the snare may extend outside of the distal end of the elongate body to at least partially define the loop and aperture of the snare loop assembly. In some variations, one end of the snare is fixed relative to one or more portions of the closure device, while the other end may be advanced or retracted through the elongate body. Movement of the free end of snare may change the amount of the snare loop assembly that is disposed outside of elongate body, and thus change the size of the loop and aperture defined thereby. Specifically, advancement of the snare through the elongate body may increase the size of the loop and aperture of snare loop assembly, while retraction of the snare may decrease the size of loop and aperture of the snare loop assembly to close the snare loop assembly. The free end of the snare may be manipulated in any suitable manner. In some variations, the snare may be attached directly to one or more portions of the handle, as will be described in more detail below. In other variations, a hypotube, rod, or other rigid structure may be attached to the free end of the snare. This structure may in turn be moved by the handle, which may help facilitate advancement or withdrawal of the snare through the elongate body.

In variations where one end of the snare is fixed relative to the closure device, the snare may be fixed to any suitable portion of the device. For example, in some variations one end of the snare may be fixedly held in, on, or near a tip of the elongate body. In other variations, the fixed end of the snare may be affixed in one or more lumens of the elongate body. In still other variations, the fixed end of the snare may be at least temporarily attached to the device's handle. Although one end of the snare may be temporarily fixed relative to the closure device, it should be appreciated that this fixed end may be configured to be releasable and/or moveable, as will be described in more detail below.

The snares described here may be made of any suitable material or combination of materials. For example, in some variations the snare may be made from a shape-memory material, such as a shape-memory alloy (e.g., a nickel titanium alloy, etc.), or may be made from stainless steel, polyester, nylon, polyethylene, polypropylene, combinations thereof, and the like. In variations where the snare is made from the shape-memory material, the snare may be configured to take on a particular shape or configuration when the snare loop assembly is placed in an open configuration, but may still be at least partially withdrawn into the elongate body to place the snare loop assembly in a closed configuration. For example, snare may form a generally circular, teardrop-shaped, oval or ellipsoid, or triangular loop when the snare loop assembly is placed in an open configuration. Furthermore, in some variation, the snare loop may be angled relative to the elongate body. For example, the snare may exit the elongate body that is at an angle ($\theta$) relative to the elongate body's longitudinal axis. This angle ($\theta$) may be any suitable angle. For example, angle (A) may be about 5°, about 15°, about 30°, about 45°, about 60°, about 75°, about 90°, between about 40° and about 50°, between about 35° and about 55°, between about 30° and about 60°, or the like. Angling the snare relative to elongate body may aid the snare in capturing tissue, as angling may better position the snare relative to tissue as the closure device is moved in the body.

Suture Loop

The snare loop assemblies described here may also comprise a suture loop for maintaining tissue in a closed manner. Generally, the suture loop may be releasably attached to the snare, for example, via a retention member, as will be described in more detail below. Furthermore, the suture loop may comprise a suture knot, but need not. This suture knot may be any suitable knot, including, but not limited to, a slip knot (e.g., a one-way slip knot). In some variations, at least a portion of the knot may be held within the tip of elongate body. In other variations, the suture knot at least partially extend from the tip of the elongate body, or may be positioned outside of the tip and may be temporarily held in fixed relation to the elongate body. When the suture loop comprises a suture knot, the suture loop may comprise a loop portion, a suture knot, and tail extending from the suture knot. The suture tail may be pulled through the suture knot to reduce the diameter of the loop portion.

In variations where the suture loop comprises a slip knot, suture may be advanced or withdrawn through the slip knot to change the size of suture loop. In some instances where the suture knot is held within or against a tip of elongate body, the suture knot may not move while the size of suture loop is changed. This may help prevent the closure device from damaging tissue, as will be described in more detail below.

In some variations, the suture loop further comprises a unidirectional locking structure. In these variations, the unidirectional locking structure may be any structure capable of being advanced along the suture in one direction, but resisting movement in a second direction. In these variations, the locking structure may be advanced over a portion of the suture loop to help lock a suture knot in place. For example, in some variations the unidirectional locking structure may comprise a bead or mechanical structure which is placed at least partially around the suture. In these variations, the bead may comprise one or more teeth or projections that allow for the bead to be advanced along the suture in one direction, but prevents or resists movement in the opposite direction. The locking structure may be advanced via one of the closure devices described here, or may be advanced by a separate device after the suture loop has been released from the closure device.

The suture loop may be made from any suitable material useful in exclusion or closure. For example, it may be made of a biodegradable material (e.g., polylactic acid, polyglycolic acid, polylactic-co-glycolic acid, etc.), or may be made of a non-biodegradable material (e.g., metal, steel, polyester, nylon, propylene, silk, combinations thereof and the like).

When the suture loop is tightened to close tissue, it may be possible for tissue to be pulled into the suture knot of the suture loop. If too much tissue is pulled into the suture knot, the suture knot may clog or jam in a way that prevents the suture loop from being further tightened. In some variations the suture loop may comprise one or more pledgets or tube sections to help shield a portion of the suture knot, such as those described in U.S. patent application Ser. No. 13/490,919, which was previously incorporated by reference.

Retention Member

When the snare loop assemblies described here comprise a retention member releasably coupling a snare and a suture loop, the retention member may be any suitable member, such as dual-lumen tubing. FIGS. 16A-16C depict illustrative retention members that may be used with the devices described herein. FIG. 16A shows an end view of a retention member (1614) having first and second lumens (1616, 1618) for retaining a closure element and a suture loop therein. In this variation, the second lumen (1618) has a slit or other opening (1620) along its length, for allowing the suture to pass therethrough when it is ready to be deployed. Of course, it should be understood that the first and second lumens may be positioned or oriented in any suitable way with respect to each other, and similarly, the slit or other opening on the second lumen may be positioned or oriented in any suitable fashion with respect to the first lumen (e.g., it may be approximately 180°, approximately 160°, approximately 120°, approximately 90°, approximately 60°, approximately 30°, or the like, from the first lumen (1616)). FIG. 16B provides an illustration of a retention member having a first lumen (1622), a second lumen (1624), and a slit (1626). In this variation, the slit (1626) is positioned closer to the first lumen (1622) than the slit of FIG. 16A. The width or spacing of the slit opening may be selected as desired or appropriate. Similarly, the slit need not extend or be continuous along the entire length of the retention member. In some variations, the slits may have prongs or arms along its length to help capture and retain the suture therein. In other variations, the slits may be covered at spaced apart locations therealong with a biodegradable polymer, temporarily used to tack or hold down the suture. Of course, in still other variations, the retention member does not comprise a slit, and instead comprises some other type of retention mechanism, such as the prongs or tacks described just above. In yet other variations, there are no slits or openings in the retention member and the suture loop is released upon removing or withdrawing the retention member and closing the device.

FIG. 16C provides another variation of a retention member. In this variation, the retention member has a first lumen (1628), a second lumen (1630), and a separation region (1632). The separation region may be constructed in any suitable fashion. For example, the separation region may comprise a perforated region adapted to perforate and release the suture with the application of force. Alternatively, the separation region may be a thin-walled or other type of weakened region that may be configured to break and release the suture. It should be understood that the retention member may have any suitable geometry or shape, and may be made from any suitable material. Similarly, the lumens need not be full circles or have a circular cross-sectional geometry. When these or other types of retention members are used, the suture loop may be torn out, pulled through, or otherwise released from the retention member after it has been properly positioned and tightened as desirable.

In variations in which one end of the snare may be fixed relative to the closure device, the closure device may be configured to selectively release and unfix the snare relative to the elongate body. Configuring the fixed end of the snare to be releasable may allow for release of tissue ensnared by the snare in instances where temporary or permanent device failure results in the moveable portion of the snare becoming stuck or caught.

Excess-Suture Management

In operation of the closure devices, it may be desirable to be able to open and close a snare loop assembly without prematurely releasing the suture loop from the snare assembly. Because the size of the loop of the snare loop assembly and the aperture defined thereby changes as the snare loop assembly is opened and closed, it may be necessary for the size of the suture loop to change in order to accommodate this change in aperture size and to prevent the suture from being prematurely released from the snare loop assembly. In some variations, opening the snare loop assembly may pull suture through a slip knot to increase the size of the suture loop. This may, however, provide sufficient force to the suture loop to cause the suture to break or sever. To help prevent this undesirable outcome, the suture loop may be sized such that the suture loop is as large as or larger than the size of the aperture defined by the loop of the snare loop assembly when the snare loop assembly is in an open configuration. Thus, when the snare loop assembly is moved to an open configuration, the suture loop can assume a similar size without needing to advance additional suture through the suture knot. Pre-sizing the suture loop to such a size, however, may result in extra slack in the suture loop when the snare loop assembly is in a closed configuration. To help prevent the excess suture from getting entangled with or caught on anatomical structures, instruments, or other obstructions, some or all of the slack in the suture loop may be held inside of the elongate body when the snare loop assembly is opened and/or closed.

As such, the closure devices described here may comprise one or more excess-suture management features, which may be used in any suitable manner. In some instances, the feature may be configured to apply a force to the excess suture when the device is an open and/or a closed configuration. This force may act to pull the excess suture into the elongate body or may temporarily prevent excess suture from exiting the elongate body. Additionally, this force may act to prevent the excess suture from knotting or bunching up, which may potentially affect device performance.

Figure 2:
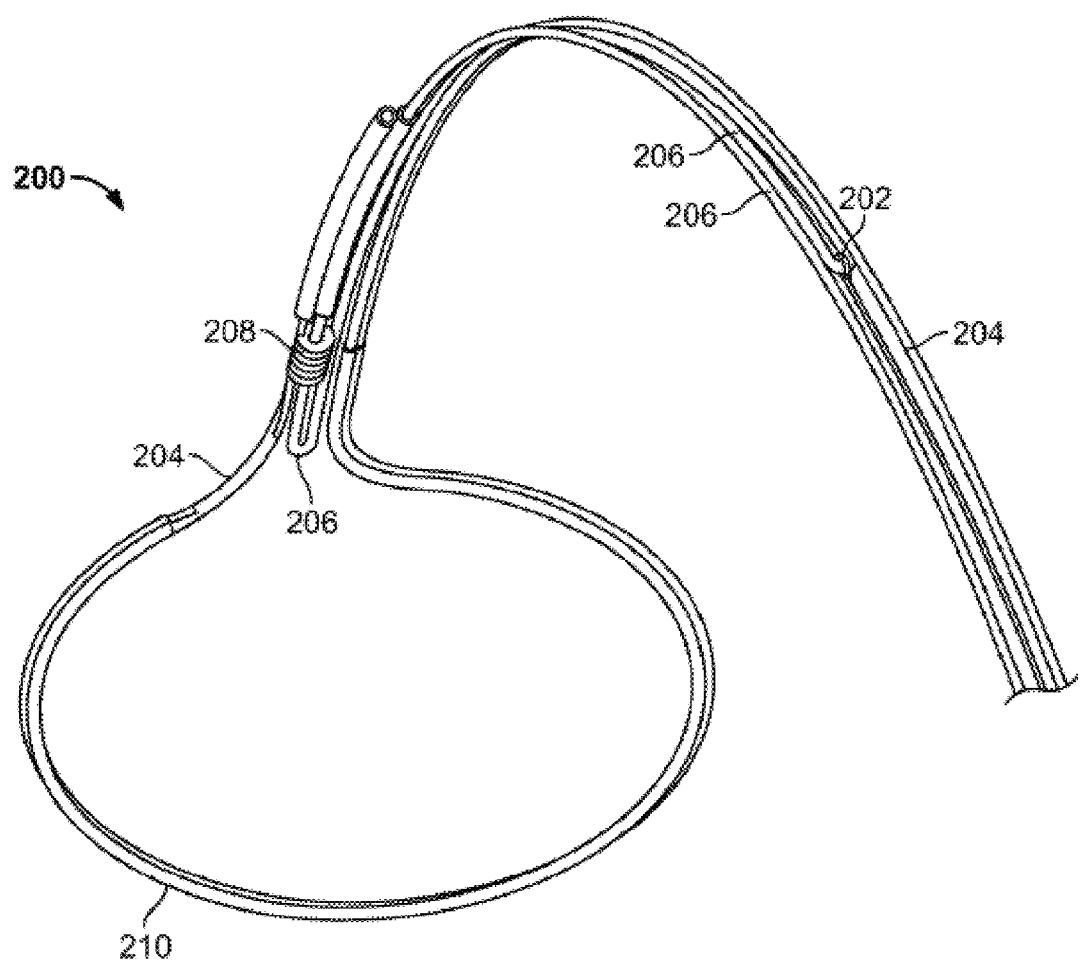
FIG. 2 is a view of a distal end of a snare loop assembly, including a suture hook.

In some variations, a suture hook may be used to hold the excess suture within the elongate body. FIG. 2 shows one such variation of a snare loop assembly (200) having suture hook (202). Also shown there is snare (204), suture loop (206) having suture knot (208), and retention member (210). As illustrated in FIG. 2, suture hook (202) may hold excess suture from suture loop (206) within an elongate body (not shown). In variations in which the elongate body has multiple lumens, suture hook (202) may hold excess suture in any suitable lumen.

In some variations the proximal end of the suture hook may be able to move relative to the elongate body when snare is advanced from or withdrawn through or within the elongate body, such as described in U.S. patent application Ser. No. 13/490,919, which was previously incorporated by reference. Additionally or alternatively, the closure devices may comprise, one or more pieces of separation tubing or pulley suture which may be used to help maintain excess suture within the elongate body, and may thereby limit the exposure or release of excess suture out of the elongate body, such as those described in U.S. patent application Ser. No. 13/490,919, which was previously incorporated by reference.

Releasable Snare

Figure 4A:
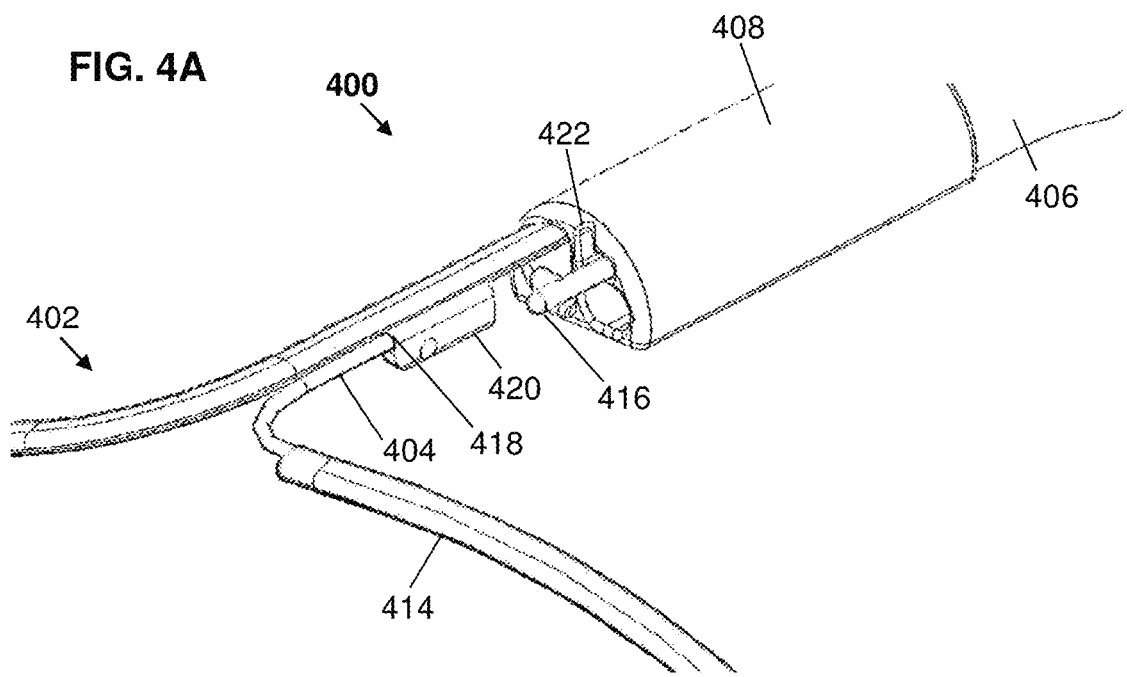
FIGS. 4A and 4B depict perspective views of a variation of a closure device having a releasable snare.
Figure 4B:
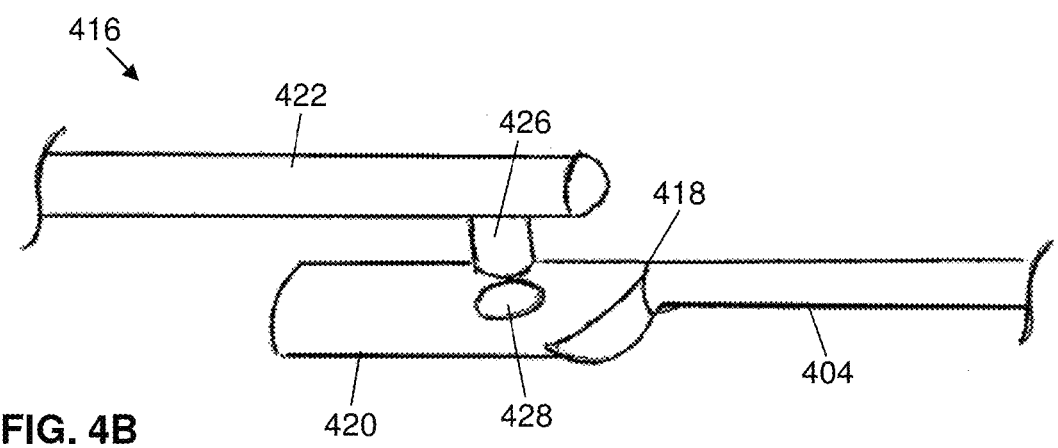

As mentioned above, in some variations, the closure devices described here may comprise a releasable snare. In some variations, the snare may be configured to be releasable along its length to separate the snare into two separate snare portions. In other variations, the closure device may comprise a snare having an end that is fixed relative to the elongate body, and the closure device may be further configured to release the fixed end of the snare. In these variations, the fixed end of the snare may be released from the closure device in any suitable manner. For example, FIGS. 4A and 4B illustrate one such distal portion of a closure device (400) having a snare loop assembly (402) with a releasable snare (404). As shown in FIG. 4A, the closure device (400) may comprise an elongate body (406) having a tip (408), and the snare loop assembly (402) may extend at least partially from the tip (408). When the snare loop assembly (402) extends from the tip (408) it may form a loop having an aperture therethrough (such as described above with respect to FIG. 1 above). The snare loop assembly (402) may comprise a snare, a suture loop, and a retention member releasably connecting the snare (404) to the suture loop, although only the snare (404) and the retention member (414) are illustrated in FIG. 4A. The snare (404) may have a first end (not shown) that is connected to one or more portions of a control portion (not shown) of the closure device (400), and a second end (418) that is connected to a hub (420). The hub (420) may be configured to fix the second end (418) of the snare (404) relative to the elongate body (406), as will be described immediately below. When the hub (420) fixes the second end (418) of the snare (404) relative to the elongate body (406), the first end of the snare (404) may be manipulated (e.g., via a control) to open and close the snare (404) and snare loop assembly (402).

To fix the hub (420) (and with it, the second end (418) of the snare (404)) relative to the elongate body (406), the snare loop assembly (402) may further comprise a release component (416) configured to releasably fix the hub (420) relative to the elongate body (406). Specifically, the release component (416) may be configured to be temporarily coupled with the hub (420). The release component (416) and hub (420) may be configured such that, when coupled, they are fixed in an axial direction, but may disengage in one or more radial directions. The elongate body (406) may further comprise an aperture (422) (shown in FIG. 4A as positioned in the tip (408) of the elongate body (406)) sized and shaped to receive the hub (420) and release component (416) when the hub (420) and release component (416) are temporarily coupled. When the coupled hub (420) and release component (416) are positioned within the aperture (422), the aperture (422) may be sized and shape to prevent disengagement of the hub (420) from the release component (416). Accordingly, when the hub (420) and release component (416) may be coupled and positioned in the aperture (422), the hub (420) and release component (416) may be fixed relative to each other (e.g., since the aperture (422) is configured to prevent disengagement of the hub (420) and the release component (416)). The release component (416) may be fixed relative to the elongate body (406), which may cause the hub (420) to be locked in place relative to the elongate body (406).

With the hub (420) fixed in place relative to the elongate body (406), the second end (418) of the snare (404) is also fixed relative to the elongate body (406) and the first end of the snare (404) may be manipulated to open and close the snare loop assembly (402) as described above. If it becomes necessary to release the fixed second end (418) of the snare (404), the release component (416) may be unlocked and advanced relative to the elongate body (406). Advancement of the release component (416) may advance the hub (420) out of the aperture (422). As the hub (420) exits the aperture (422) and the aperture (422) no longer holds the hub (420) and release component (416) in a coupled configuration, the hub (420) may decouple from the release component (416), thereby releasing the second end of the snare (404) from the release component (416) (and with it, the elongate body (406)).

The hub (420) and release component (416) may be configured to temporarily couple in any suitable manner. For example, FIG. 4B depicts one variation of the hub (420) and the release component (416). As shown there, the release component (416) may comprise an elongate rod member (424) and a projection (426) extending from a side of the elongate rod member (424). The hub (420) may in turn comprise an aperture (428) sized and configured to receive the projection (426). To temporarily couple the hub (420) and the release component (416), the projection (426) may be inserted into the aperture (428) of the hub (420). When the projection (426) is positioned within the aperture (428), this engagement may substantially prevent the hub (420) from moving axially relative to the release component (416). Additionally, when positioned within the aperture (422) of the elongate body (406), the constraints of the aperture (422) may prevent the projection (426) from exiting the aperture (428) of the hub (420). Conversely, when the hub (420) and the release component (416) are not constrained by the aperture (422) of the elongate body (406), the projection (426) may be free to exit the aperture (428) of the hub (420) to release the hub (420) (and with it, the second end of the snare (404)) from the release component (416) and the elongate body (406). While the release component (416) is shown in FIG. 4B as having a projection (426), it should be appreciated that in some variations the hub (420) may comprise a projection which may engage an aperture in the release component.

The release component (416) may be moveable relative to the elongate body (406) in any suitable manner. For example, in variations where the release component (416) comprises a rod member (424), such as the variation shown in FIG. 4B, a proximal portion of the rod member (424) may be operatively connected to one or more controls which may be used to advance and/or retract the release component (416). The control may be further configured to at least temporarily fix the position of the release component (416) relative to the elongate body. For example, the control may advance a distal portion of the release component (416) out of the aperture (422) of the elongate body (406). The release component (416) may be engaged with the hub (420) (such as described above), and the release component (416) may be retracted via the control to pull the release component (416) and hub (420) into the aperture (422) of the elongate body (406) to lock the hub (420) and release component (416) together. The release component (416) may then be temporarily locked into place to fix the hub (420) and second end (418) of the snare (404) in place relative to the elongate body (406). To release the second end of the snare (404), the release component (416) may be unlocked and advanced via the control to push the hub (420) out of the aperture (422), thereby allowing the snare (404) and hub (420) to disengage the release component (416).

Figure 5A:
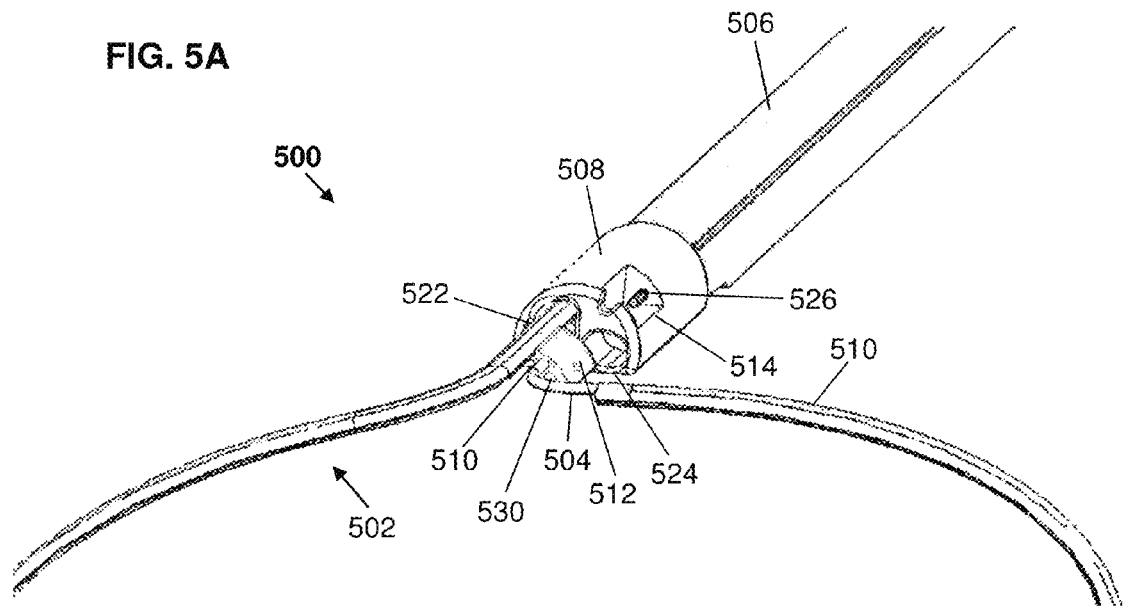
FIG. 5A depicts a perspective view of a variation of a closure device having a releasable snare.
Figure 5B:
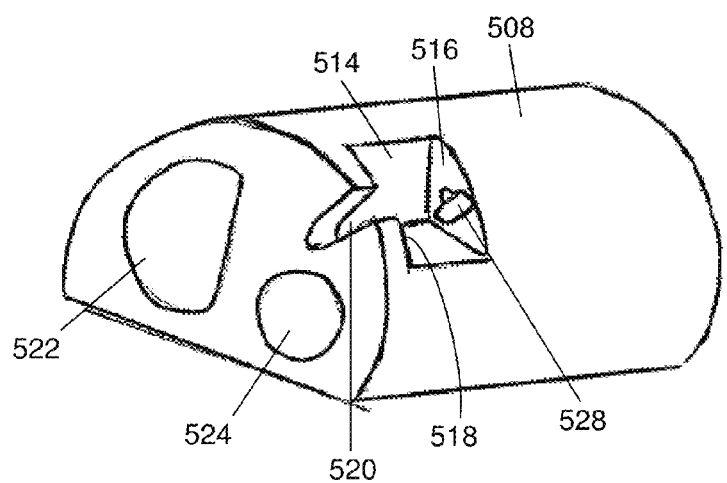
FIG. 5B shows a perspective view of a tip of the closure device shown in FIG. 5A.

In other variations, a snare may have a fixed end that may be releasable from a side wall of the elongate body (or a tip thereof). FIGS. 5A and 5B depict another variation of a closure device (500) having a snare loop assembly (502) having a releasable snare (504). Specifically, as shown in FIG. 5A, the closure device may comprise an elongate body (506) and a tip (508) at the distal end of the elongate body (506). The snare loop assembly (502) may comprise a snare, a suture loop, and a retention member releasably connecting the snare to the suture loop, although only the snare (504) and the retention member (510) are shown in FIG. 5A. The snare loop assembly (502) may extend from the tip (508) to form a loop defining an aperture and which may be placed around tissue as discussed in more detail above. The snare (504) may have a first end (not shown) that is operatively connected to one or more controls and a second end (510) connected to a shuttle (512). Generally, the shuttle (512) may be a structure configured to connect to the snare (504) and to be releasably coupled to the elongate body (506) of the closure device, and thus may be configured to fix the second end (510) of the snare (504) relative to the elongate body (506), as will be described in more detail below. When the shuttle (512) fixes the second end (510) of the snare (504) relative to the elongate body (506), the first end of the snare (504) may be advanced or withdrawn (e.g., via the control) to open or close the snare (504) and snare loop assembly (502). The shuttle may be formed from any suitable material or materials, such as, for example, one or more metals (e.g., stainless steel), one or more rigid plastics, or the like. In some variations, the shuttle (504) may be formed from the same material or materials as a portion of the elongate body (506) (e.g., the tip (508) of the elongate body (506)), but need not be.

To fix the shuttle (512) relative to the elongate body (506), the tip (508) may comprise a recess (514) in a side wall of the tip (508) for receiving the shuttle (512). FIG. 5B shows a perspective view of tip (508) and recess (514). The recess (514) may comprise a rear surface (516) and a front surface (518) configured to prevent axial movement of the shuttle (512) when the shuttle (512) is positioned in the recess (514). Additionally, the tip (508) may comprise a window (520) extending between the front surface (518) of the recess (514) and a distal end of the tip (508), such that the snare (504) may extend through the window (520) when the shuttle (512) is positioned in the recess (514). The window (520) may also be open into the side of the tip (508), which may allow the snare to enter and exit the window (520) through the side of the tip (508) when the shuttle (512) is inserted into or removed from the recess (514).

Also shown in FIG. 5B is a first lumen (522) and a second lumen (524) extending through the tip (508) and the elongate body (506). The first end of the snare (504) may extend through the first lumen (522), where it may be operatively connected to a control (not shown). The control may advance and retract the first snare (504) to control the size of the snare loop assembly (502), such as described in more detail above. Since the suture loop (not shown) is coupled to the snare (504) by the retention member (512), movement of the first end of the snare (504) may move part of the suture loop and the retention member (512) into or out of the first lumen (522). Additionally, in variations where the suture loop is sized to have an amount of excess suture (as will be described in more detail below), some or all of this excess suture may be held or otherwise maintained in the first lumen (522). When the suture loop comprises a suture knot (not shown), the suture knot and a tail of the suture loop may be positioned in and/or extend through the second lumen (524).

The snare loop assembly (520) may further comprise a lock wire (526) for fixing the shuttle (512) relative to the tip (508) when the shuttle (512) is positioned in the recess (514). Specifically, the tip (508) may comprise a lock wire lumen (528) extending through the elongate body (506) and into recess (514) such that lock wire (526) may be advanced through the lock wire lumen (528) and into the recess (514). The shuttle (512) may comprise a lock lumen (530) extending therethrough, and shuttle (512) may be configured such that the lock lumen (530) is aligned with the lock wire lumen (528) when the shuttle (512) is positioned in the recess (514). When the shuttle (512) is positioned in the recess (514) to align the lock lumen (530) with the lock wire lumen (528), the lock wire (526) may be advanced from the lock wire lumen (528) through the lock lumen (530) of the shuttle (512) (and in some variations may be further advanced through a second portion of the lock wire lumen (528) on the opposite side of the recess (514)). The engagement between the lock wire (526), the tip (508), and the shuttle (512) may hold the shuttle (512) in place in the recess (514), thereby fixing the shuttle (512) (and with it, the second end (510) of the snare (504)) relative to the tip (508). To release the fixed second end (510) of the snare (504), the lock wire (526) may be withdrawn into the lock wire lumen (528) to disengage the lock wire (526) from the shuttle (512).

Figure 6E:
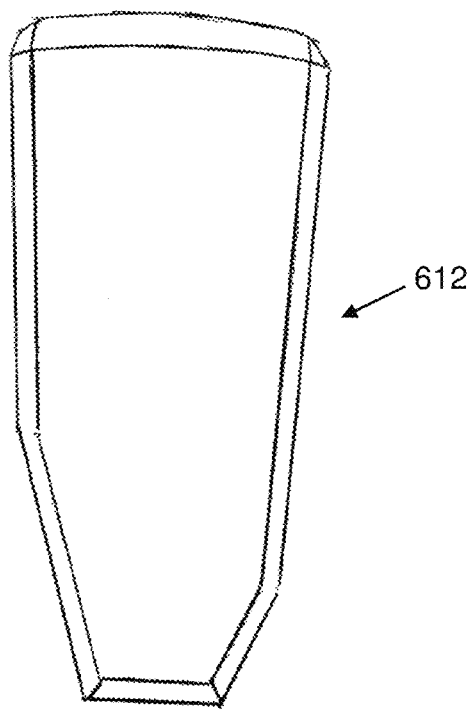
FIGS. 6E-6H show top, side, front and back views, respectively, of a shuttle for use with the closure device shown in FIGS. 6A and 6B.
Figure 6F:
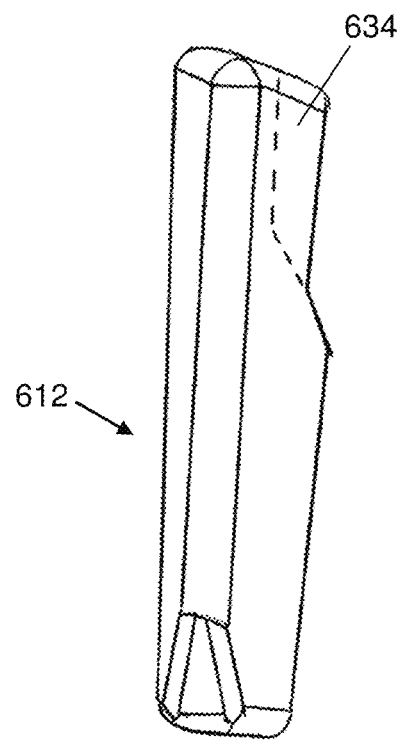

Depending on the relative shapes of the shuttle and the recess of the tip, rotation of the second end of the snare may have a tendency to rotate the shuttle relative to the tip of the elongate body. Accordingly, in some variations, the snare may be configured to help minimize rotation of the shuttle (and thus the fixed end of the snare) relative to the elongate body. For example, FIGS. 6A-6H depict one such variation of a closure device (600) having a snare loop assembly (602) with a releasable snare (604). Specifically, FIGS. 6A and 6B show perspective views of a distal portion of the closure device (600). As shown there, closure device (600) may comprise an elongate body (606) and a tip (608). The snare loop assembly (602) may comprise a snare, a suture loop, and a retention member releasably connecting the snare to the suture loop, although only the snare (604) is illustrated in FIGS. 6A and 6B. The snare (604) may have a first end (not shown) that is connected to one or more portions of a control (not shown), and a second end (610) that is connected to a shuttle (612). The shuttle (612) may be configured to fix the second end (610) of the snare (604) to the elongate body (606), and the first end of the snare (604) may be advanced or withdrawn (e.g., via the control) to open or close the snare (604) and snare loop assembly (602).

The tip (608) may comprise a recess (614), such as described in more detail above, for receiving the shuttle (612). Specifically, the shuttle (612) may be positioned in the recess (614), as shown in FIG. 6A, and may be temporarily fixed in place relative to the tip (608) to lock the second end (610) of the snare (604) in place relative to the elongate body (604). To release the snare (604), the shuttle (612) may be disengaged from the tip (608), as shown in FIG. 6B. In some instances, the shuttle (612) may be sized and shaped such that when the shuttle (612) is placed in the recess (614), the outer surface of the shuttle (612) matches the contour of the side wall of the tip (608). By matching the contours of the shuttle (612) with the side wall of the tip (608), the shuttle (612) and tip (608) may reduce the likelihood of damaging tissue during advancement of the closure device (600).

FIGS. 6C and 6D depict a top and front view, respectively, of the tip (608) of a closure device). As shown there, recess (614) may comprise a rear surface (616) and a front surface (618), which may be configured to prevent axial movement of the shuttle (612) relative to the recess (614). The tip (608) may further comprise a window (620) extending between the front surface (618) and a distal end of the tip (608) and opening into a side of the tip (608). When the shuttle (612) is positioned within the recess (614), such as shown in FIG. 6A, the snare (604) may extend out of the distal end of the tip (608) through the window (620). Also shown in FIG. 6D are first (622) and second (624) lumens. The first end of the snare (604) may extend through the first lumen (622), such as described in more detail above. Similarly, a suture knot and a tail of the suture loop may be positioned in and/or extend through the second lumen (624), as described in more detail above.

Figure 6G:
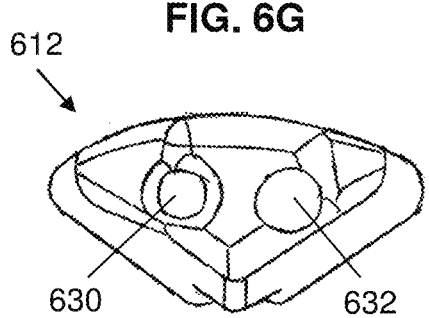
Figure 6H:
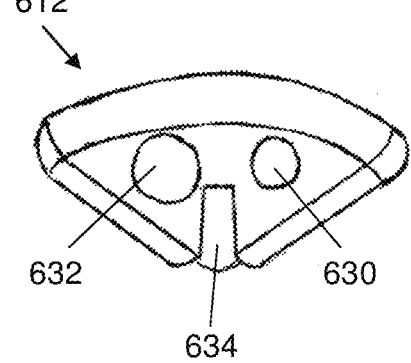

The snare loop assembly (620) may further comprise a lock wire (626) for fixing the shuttle (612) relative to the tip (608) when the shuttle (612) is positioned in the recess (614). Specifically, the tip (608) may comprise a lock wire lumen (628) extending through the elongate body (606) and into recess (614) such that lock wire (626) may be advanced through the lock wire lumen (628) and into the recess (614). FIGS. 6E-6H show top, side, front and rear views, respectively, of the shuttle (612) of FIGS. 6A and 6B. As shown there, the shuttle (612) may comprise a lock lumen (630) extending therethrough, and the lock lumen (630) may align with the lock wire lumen (628) when the shuttle (612) is positioned in the recess (614). When the shuttle (612) is positioned in the recess (614), the lock wire (626) may be advanced from the lock wire lumen (628) through the lock lumen (630) of the shuttle (612) (and in some instances may be further advanced through a second portion of the lock wire lumen (628) on the opposite side of the recess (614)). The engagement between the lock wire (626), the shuttle (612) and the lock wire lumen (628) may prevent the shuttle (612) from exiting the recess (614), thereby fixing the shuttle (612) (and with it, the second end (610) of the snare (604)) relative to the tip (608). To release the fixed second end (610) of the snare (604), the lock wire (626) may be withdrawn into the lock wire lumen (628) to disengage the lock wire (626) from the shuttle (612). Snare (604) is not shown in FIGS. 6G and 6H. Instead, FIGS. 6G and 6H depict a snare lumen (632) in the shuttle (612), into which the snare (604) may be placed and affixed (e.g., via one or more adhesives, welding, mechanical connection or the like).

As mentioned above, the shuttle (612) may be configured to help minimize rotation of the shuttle (612) relative to the recess (614). Specifically, in the variation of the closure device (600) shown in FIGS. 6A-6H, the shuttle (612) may comprise a channel (634) and the recess (614) may comprise a projection (636) which is configured to be positioned in and engage the channel (634) of the shuttle (612) when the shuttle (612) is positioned in the recess (614) of the tip (608). The engagement between the projection (636) and the channel (634) of the shuttle (612) may prevent rotation of the shuttle (612) relative to the tip (608).

Figure 7B:
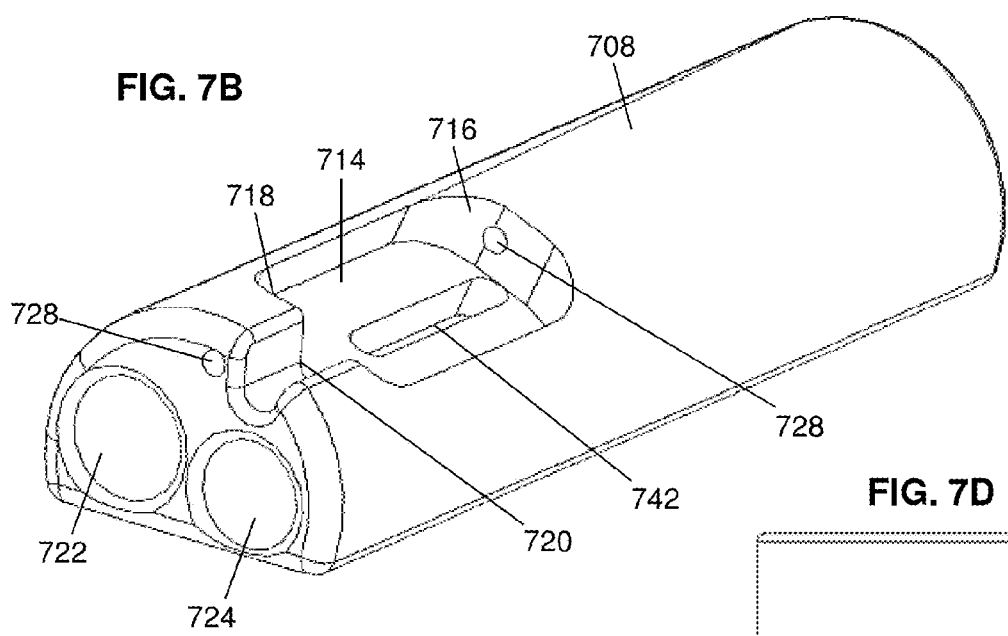
FIGS. 7B-7D show perspective, front, and top views, respectively, of a tip of the closure device shown in FIG. 7A.
Figure 7C:
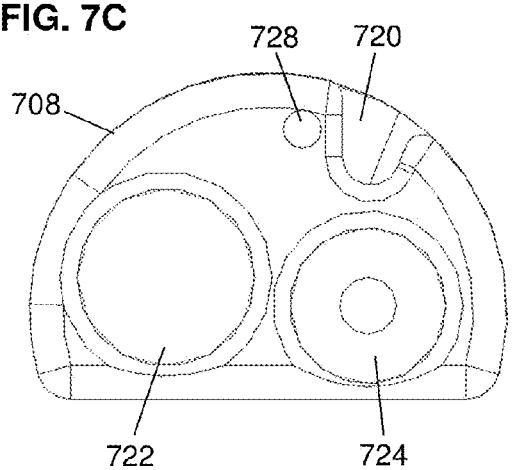
Figure 7D:
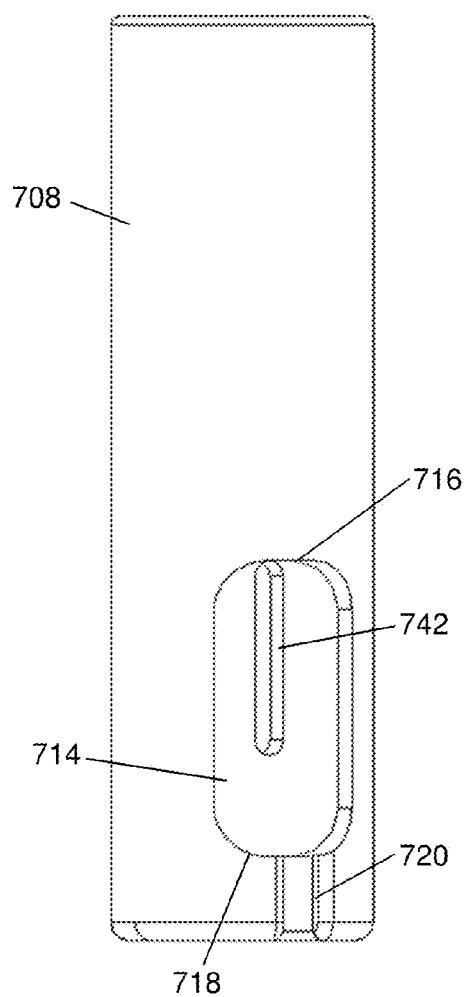
Figure 7E:
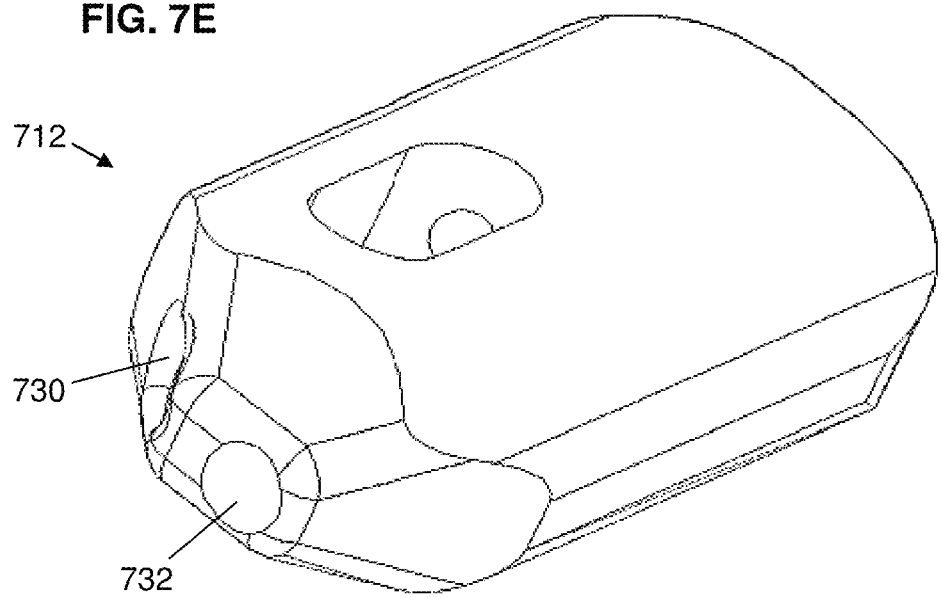
FIGS. 7E-7I show top perspective, bottom perspective, front, top, and side views, respectively, of a shuttle for use with the closure device of FIG. 7A.
Figure 7F:
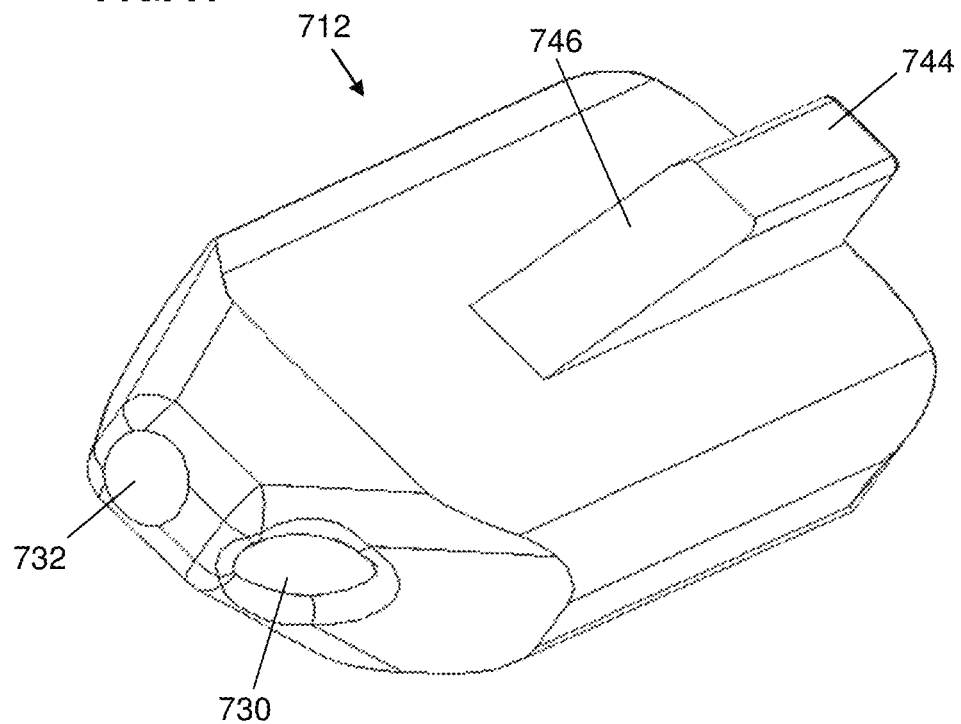
Figure 7G:
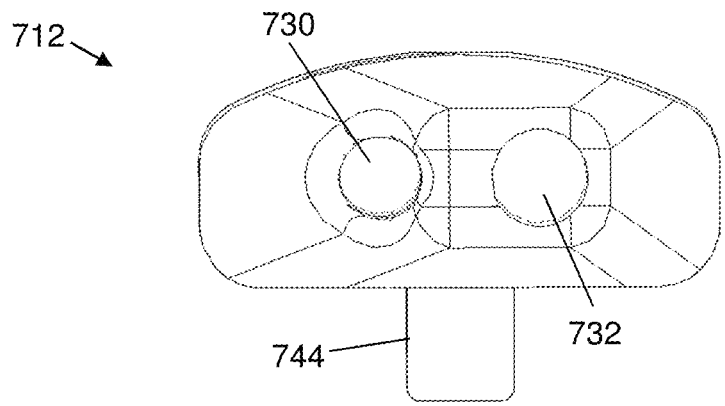
Figure 7H:
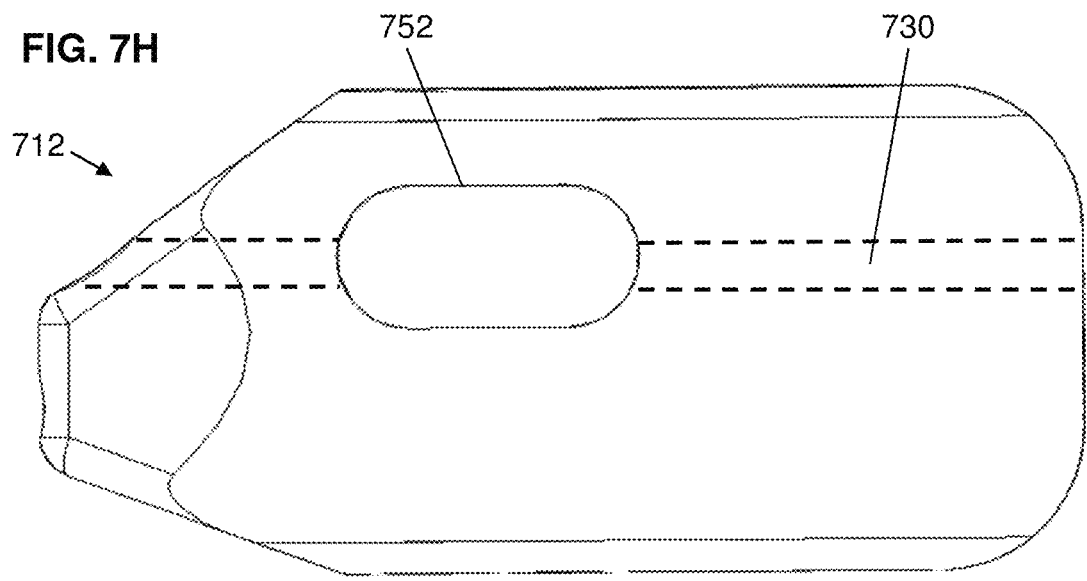
Figure 7I:
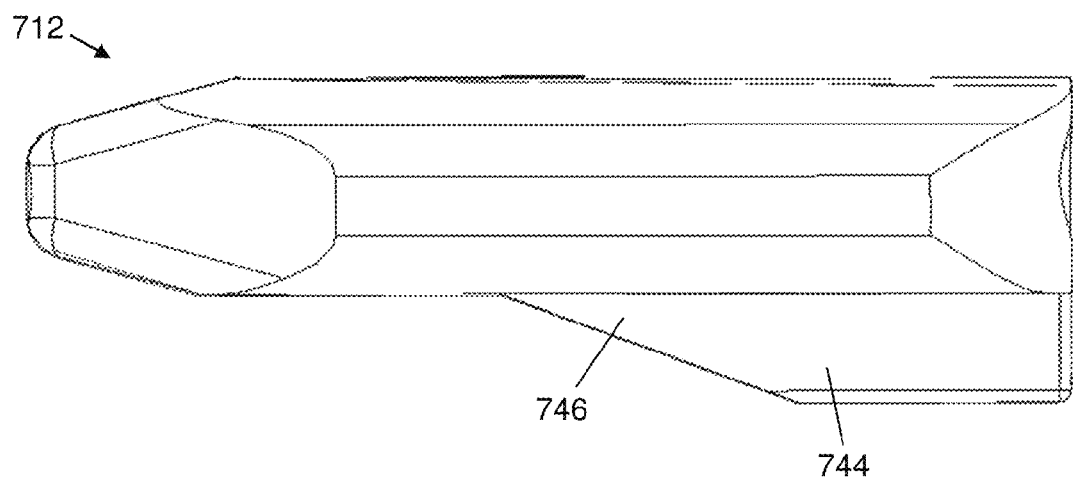

In other variations, the shuttle (612) may comprise one or more projections that may engage a recess within the tip (608). For example, FIGS. 7A-7J show a variation of one such variation of a closure device (700). Closure device (700) may share a number of features with the variation of the closure device (600) shown in FIGS. 6A-6H, and common features will not be specifically described. FIG. 7A shows a perspective view of a distal portion of the closure device (700) comprising a tip (708), a shuttle (712), and a lock wire (726). FIGS. 7B-7D show a perspective view, front view, and top view, respectively, of the tip (708). As shown there, tip (708) may comprise a recess (714) having a rear surface (716) and a front surface (718), first (722) and second (724) lumens, an aperture (720) extending between the front surface (718) and a distal end of the tip (708), and a lock wire lumen (728). Also shown there is a track (742) further disposed in the recess (714).

FIGS. 7E-7I show top perspective, bottom perspective, front, top, and side views, respectively, of the shuttle (712). As shown there, the shuttle (712) comprises a lock lumen (730) and a snare lumen (732). The shuttle (712) may also comprise a projection (744), which may extend from a bottom surface of the shuttle (712). When the shuttle (712) is positioned within the recess (714), the projection (744) may be configured to at least partially fit within and engage the track (742) of the tip (708). This engagement between the projection (704) and track (702) may prevent rotation between the shuttle (712) and the tip (708). In the variation of shuttle (612) shown in FIGS. 7E-7I, the projection (744) may comprise a ramped portion (746). When the shuttle (712) is released from the tip (708) (e.g., by withdrawal of the lock wire (728), as described in more detail above), the ramped portion (706) may promote easier sliding of the ramped portion (706) out of the track (702), which may reduce the likelihood that the shuttle (712) becomes stuck in the recess (714).

When variations of the releasable snares described here are fixed in place using a lock wire, it may be desirable to reduce the likelihood that the lock wire may be prematurely withdrawn from the shuttle to release the fixed end of the snare. For example, bending or twisting of the elongate body may provide one or more pulling forces to the lock wire. In these variations, it may be desirable to increase the force required to pull the lock wire from the shuttle. For example, in some variations, one or more adhesives may be used to temporarily couple the lock wire to either the shuttle (e.g., to a lock lumen thereof) and/or the elongate body (e.g., to a lock wire lumen thereof). In these instances, the adherence provided by the adhesive may resist withdrawal of the lock wire from the shuttle, such that incidental forces applied to the lock wire may not be sufficient to cause premature release of the lock wire. To release the shuttle from the elongate body, the force applied to the lock wire (e.g., via a controller, as will be discussed in more detail below) will need to be large enough to break the connection between the lock wire and the adhesive.

Figure 7J:
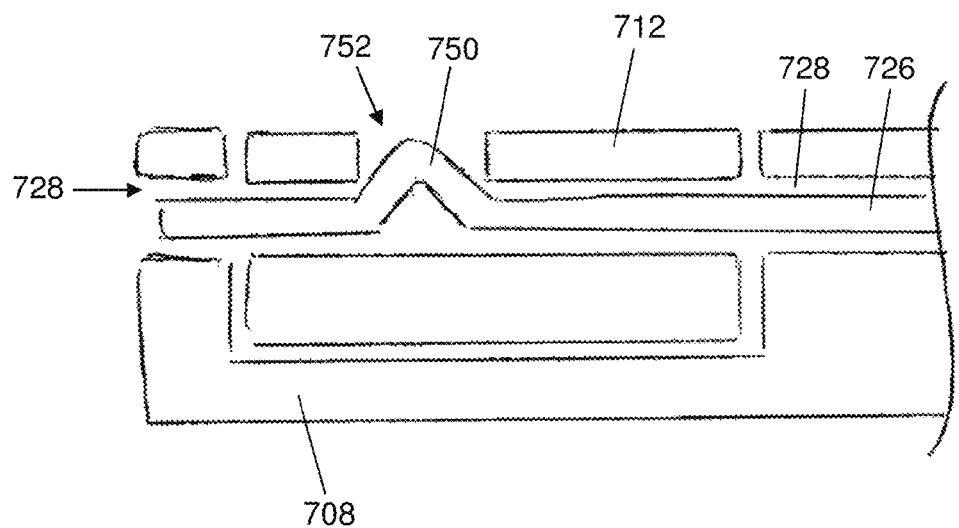
FIG. 7J shows a cross-sectional side view of a portion of the closure device shown in FIG. 7A.

In other variations, the shape of the lock wire may increase the force required to withdraw the lock wire from the suture. In some variations the lock wire may comprise one or more bends or coils which may resist movement relative to the shuttle and/or elongate body. For example, in the variation of the closure device (700) shown in FIGS. 7A-7J, the lock wire (726) may comprise a bend (750) which may be configured to engage a portion of the shuttle (712). Specifically, the shuttle (712) may comprise a window (752) extending from the lock lumen (730) to an exterior of the shuttle (712). When the lock wire (726) is positioned to lock the shuttle (712) in place relative to tip (708), the bend (750) of the lock wire (726) may be positioned to extend at least partially into the window (752) of the shuttle (712). For example, as shown in FIG. 7J, the lock wire (726) may extend from a first portion of the lock wire lumen (728) proximal of the shuttle (712), through the lock lumen (730), and into a second portion of the lock wire lumen (728) distal of the shuttle (712) to lock the shuttle (712) relative to the tip (708). When the bend (750) of the lock wire (726) extends at least partially into the window (752) of the shuttle (712) (as shown in FIG. 7J), the bend (750) may resist proximal movement of the lock wire (728) relative to the shuttle (712). This resistance may prevent inadvertent release of the lock wire (726) from the shuttle (712). To release the lock wire (726), the user may apply a proximal force (e.g., via a control) sufficient enough to straighten the bend (752) such that it may enter and pass through the lock lumen (750). While the bend (752) is shown in FIG. 7J as positioned in the shuttle (712), in other instances the bend (752) may be positioned between the shuttle (712) and the lock wire lumen (728) either proximally or distally of the shuttle (712), such that the bend (752) resists being pulled into either the lock lumen (730) of the shuttle (712) and/or the lock wire lumen (728). Additionally, while shown in FIG. 7J as comprising a bend (752), the lock wire (726) may additionally or alternatively comprise a coiled portion which may resist being pulled through the lock lumen (730) of the shuttle (712) and/or the lock wire lumen (728) as discussed immediately above.

Figure 8A:
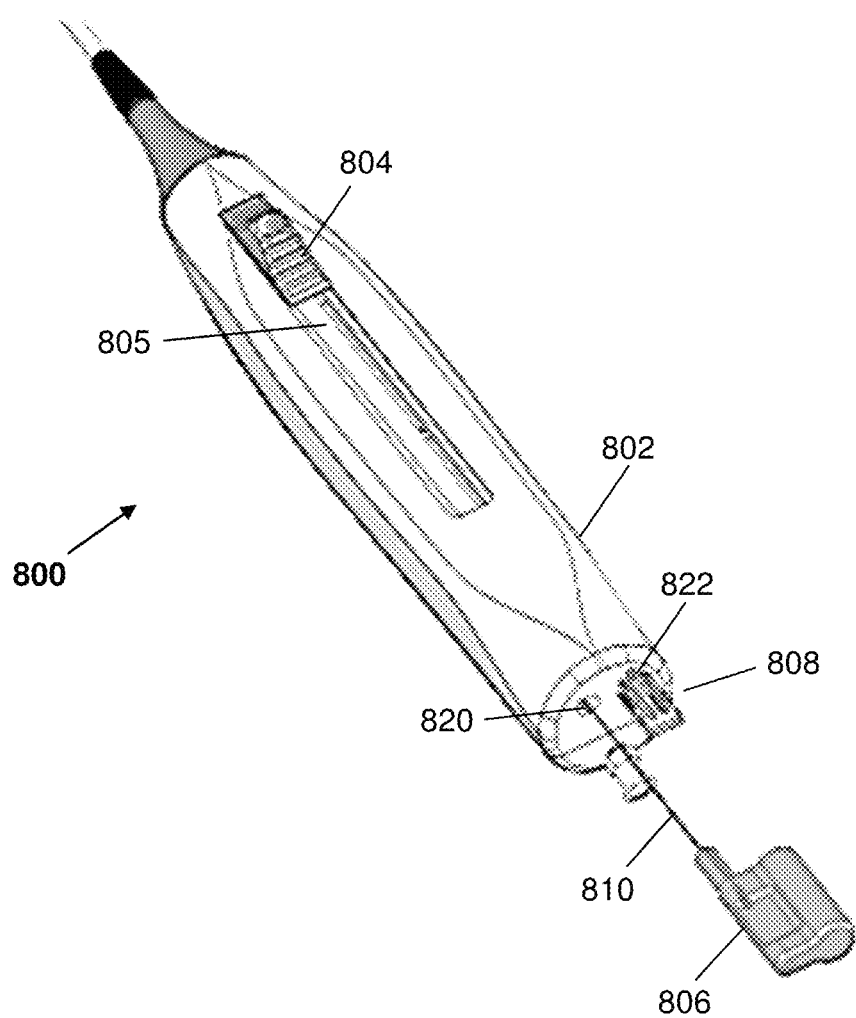
FIG. 8A shows a perspective of a handle assembly for use with the closure devices described here.

When the closure devices described comprise a snare that is temporarily fixed to the elongate body via a shuttle and a lock wire, the lock wire may be withdrawn in any suitable manner. For example, FIGS. 8A-8F depict one variation of a handle assembly (800) configured to release a fixed end of a snare (not shown) by withdrawing a lock wire. FIG. 8A shows a perspective view of handle assembly (800). As shown there, the handle assembly (800) may comprise a handle body (802), a snare control (804), a suture control (806), and a snare release (808). In these variations, a first end of the snare may be operatively connected to the snare control (804), and the second end of the snare may be fixed to a tip of the elongate body via a shuttle and a lock wire as discussed above. The snare control (804) may be advanced and retracted along a track (805) to advance and retract the first end of the snare relative to the elongate body. Advancement and retraction of the first end of the snare may open and close, respectively, the snare loop assembly. The suture control (806) may be connected to a tail (810) of the suture loop (not shown). The suture control (806) may be pulled to tighten the suture loop. Specifically, as the tail (810) of the suture loop is withdrawn, suture of the suture loop may be pulled through a suture knot of the suture loop to reduce the size of the suture loop. Similarly, the snare release (808) may be operatively connected to the lock wire (812), and may be pulled or otherwise manipulated to pull the lock wire (812) proximally relative to the elongate body (and thereby release the shuttle and fixed end of the snare from the elongate body).

Figure 8B:
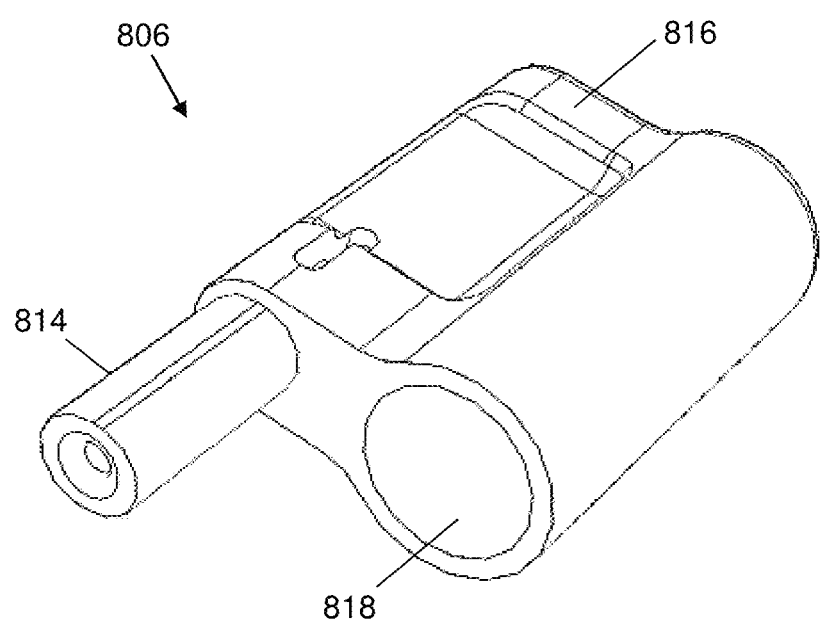
FIG. 8B shows a perspective view of a suture control for use with the handle assembly shown in FIG. 8A.
Figure 8C:
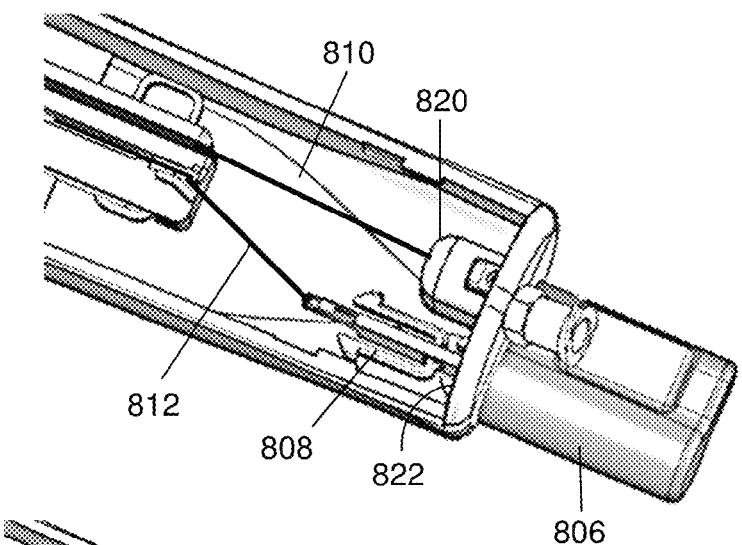
FIGS. 8C-8E show cross-sectional perspective views of the handle assembly shown in FIG. 8A.
Figure 8D:
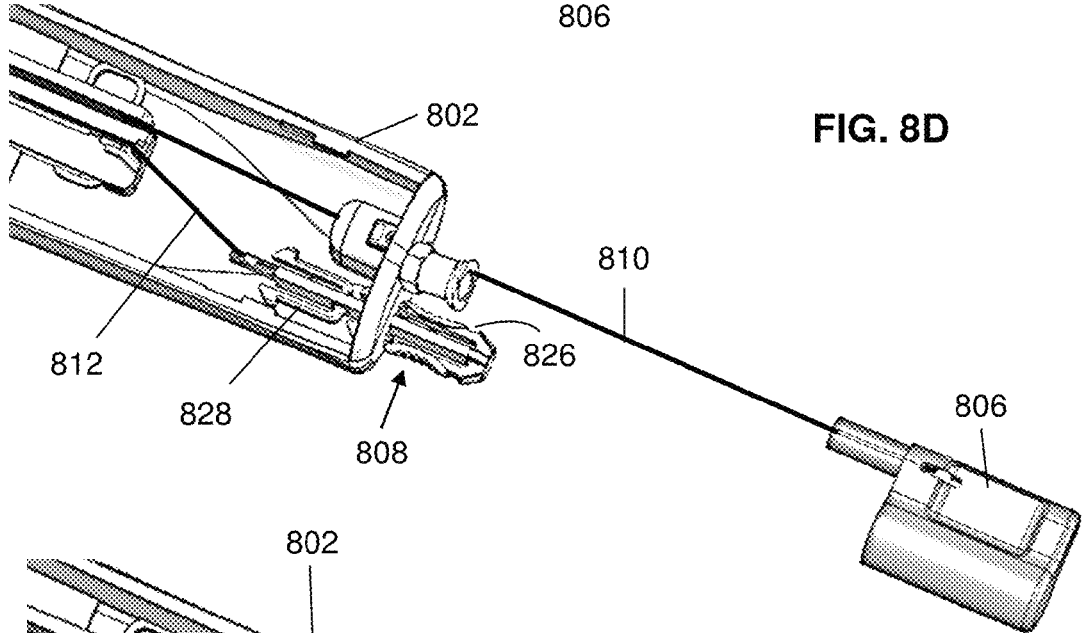
Figure 8E:
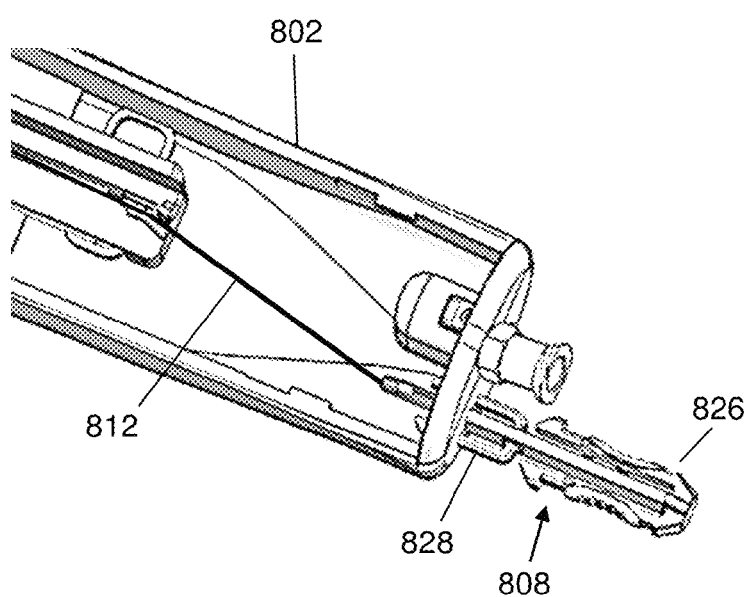

In some variations, the handle assembly (800) may be configured to minimize the likelihood that the fixed end of the snare is prematurely released. For example, in the variation of handle assembly (800) shown in FIGS. 8A-8E, the suture control (806) may be configured to at least temporarily shield access to the snare release (808). For example, FIG. 8B shows a perspective view of the suture control (806). As shown there, the suture control (806) may comprise a suture attachment portion (814), a grip portion (816), and a chamber (818) disposed in the grip portion (816). The suture attachment portion (814) of the suture control (806) may be attached to a tail portion (810) of the suture loop, and the suture attachment portion (814) may be positioned in a first opening (820) in the handle body (802) to temporarily couple the suture control (806) to the handle body (802), such as shown in FIG. 8C. Similarly, the snare release (808) may be attached to the lock wire (812) and may be positioned at least partially in a second opening (822) of the handle body (802) to temporarily couple the snare release (808) to the handle body (802), such as shown in FIG. 8C. When the suture control (806) and snare release (808) are partially positioned in the first (820) and second (822) openings, the portion of the snare release (808) extending out of the handle body (802) may be positioned within the chamber (818) of the suture control (806). Accordingly, the suture control (806) may temporarily shield the snare release (808) and may prevent a user from accessing the snare release (808) while the suture control (806) is in place. To access the snare release (808), the suture control (806) may first be disengaged from the handle body (802) and pulled proximally to expose the snare release (808), as shown in FIG. 8D. The snare release (808) may then be pulled proximally relative to the handle body (802) to pull the lock wire (812), as shown in FIG. 8E. This withdrawal of the lock wire (812) may release a fixed end of the snare, such as described in more detail above.

Figure 8F:
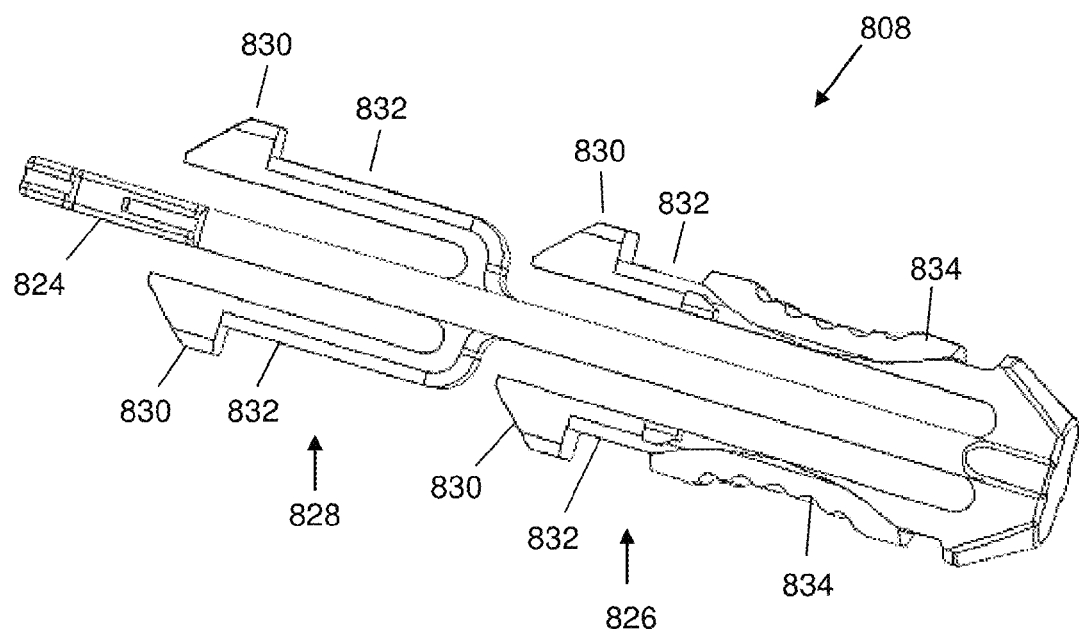
FIG. 8F shows a side view of a snare release control for use with the handle assembly shown in FIG. 8A.

In some variations, when the snare release (808) is withdrawn, the snare release (808) may be configured to control the distance the snare release (808) may be pulled. For example, FIG. 8F shows an enlarged view of a variation of the snare release (808). As shown there, the snare release (808) may have a main body (824) and first (826) and second (828) stops attached to the main body (824). Each of the first (826) and second (828) stops may comprise one or more catches (830) extending from respective arms (832). The arms (832) in turn may be connected to the main body (824) (for example, in the variation shown in FIG. 8F, each stop comprises first and second arms, each having a catch). The first stop (826) may further comprise grip portions (834) attached to the arms (832) of the first stop (826). When the snare release (808) is initially positioned in the second opening (822), the catches (830) of the first stop (826) may engage the housing body (802) to hold the snare release (808) in a first position (as shown in FIG. 8D). When positioned as such, the catches (830) of first stop (826) may prevent withdrawal of the snare release (808). Before the snare release (808) may be withdrawn, a user may apply pressure to the grip portions (834) to deflect the arms (832) and catches (830) of the first stop (826) toward the main body (824) of the snare release (808), which may allow the catches (830) to disengage the housing body (802) and pass through the second opening (822) of the control body (802). With the catches (830) of the first stop (826) disengaged from the housing body (802), the snare release (808) may be pulled proximally until the catches (830) of the second stop (828) engage the housing body (802), thereby placing the snare release (808) in a second position, as shown in FIG. 8E. The distance between the catches (830) of the first (826) and second (828) stops (i.e., the distance between the first and second positions) may be sized to limit movement between the first (826) and second (828) stops.

Figure 13A:
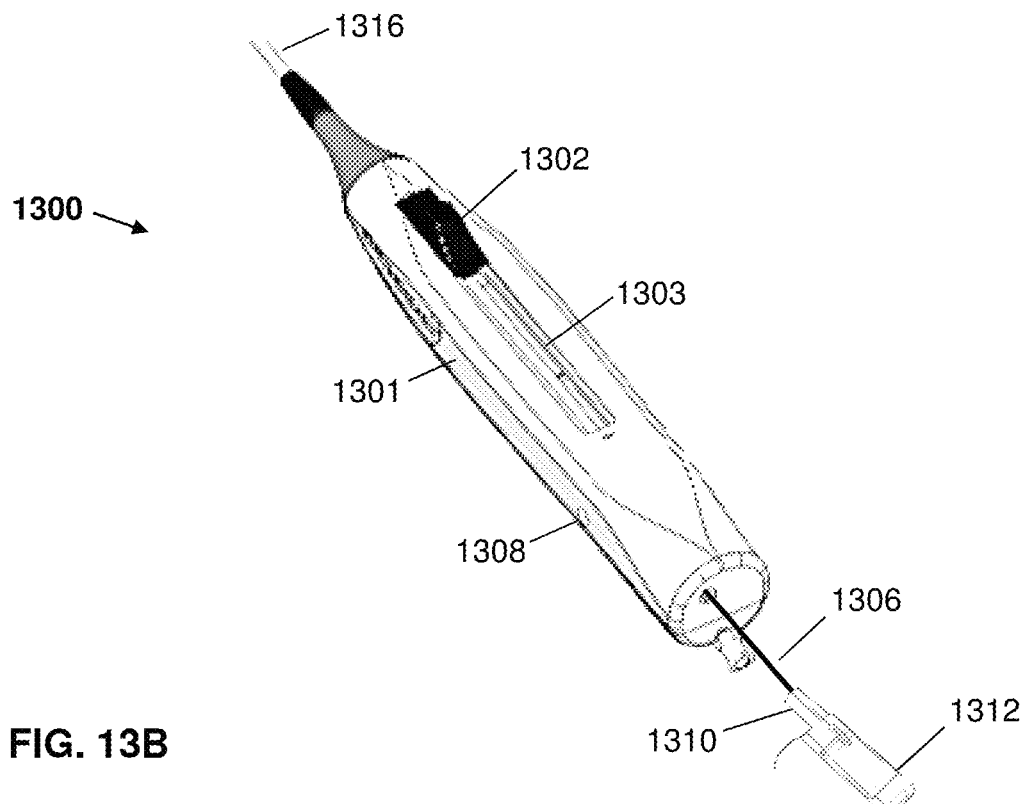
FIGS. 13A and 13B depict top views of a handle assembly for use with the closure devices described here.
Figure 13B:
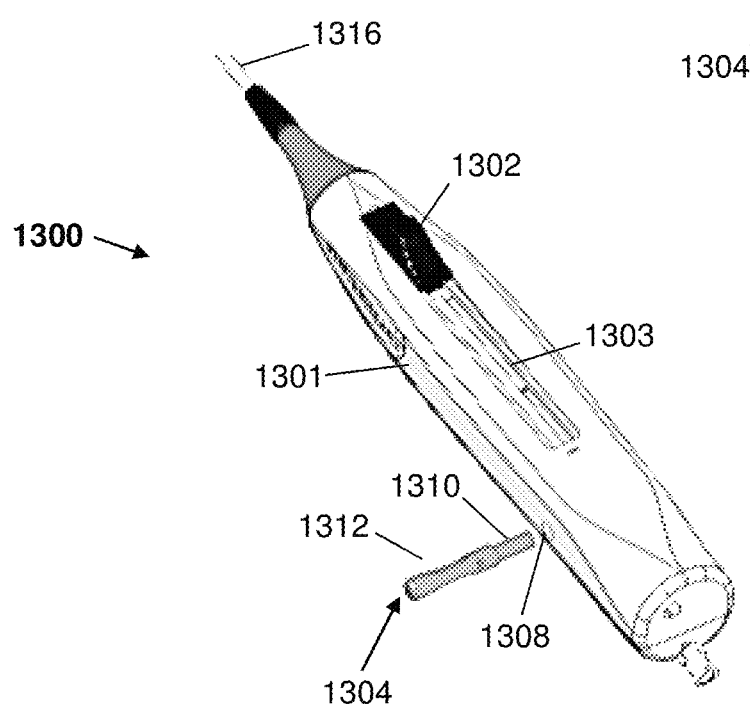
Figure 13C:
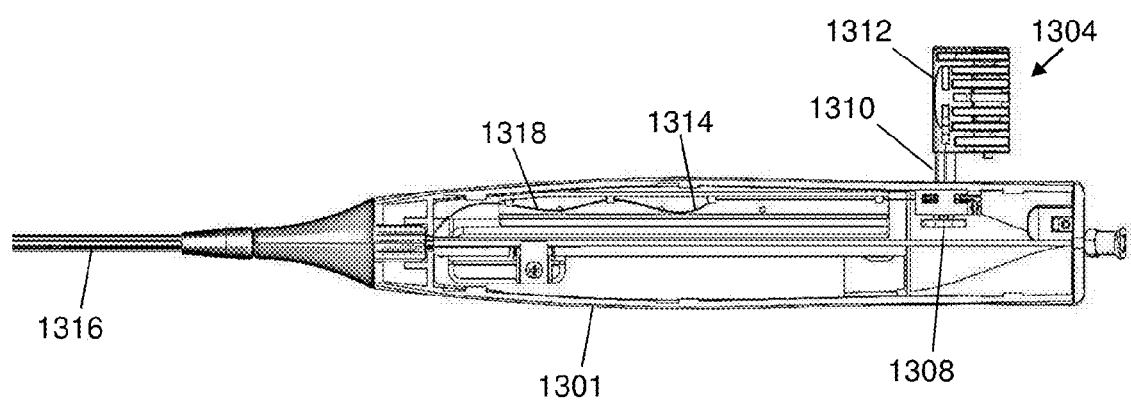
FIG. 13C depicts a cross-sectional side view of the handle assembly shown in FIGS. 13A and 13B.

FIGS. 13A-13C depict another variation of a handle assembly (1300) configured to release a lock wire from a fixed end of a snare. Specifically, FIGS. 13A and 13B show perspective views of the handle assembly (1300). As shown there, the handle assembly (1300) may comprise a handle body (1301), a snare control (1302), a suture control (1304), and a snare release button (1308). The snare control (1302) may be attached to a first end of the snare and may be moveable along a track (1303) to open and close a snare loop assembly. A lock wire (1314) may be used to fix a second end (not shown) of the snare, such as described in more detail above, and may be released using the snare release button (1308). The suture control (1304) may be connected to a tail (1306) of a suture loop (not shown), and may be withdrawn relative to the handle body (1301) to tighten the suture loop. The suture control (1304) may also be used to actuate the snare release button (1308), as will be described in more detail below.

The snare release button (1308) may be attached to or otherwise positioned relative to the lock wire (1314) such that when the snare release button (1308) is depressed, the snare release button (1308) pulls the lock wire (1314) proximally relative to the elongate body (1316) (e.g., to disengage the lock wire (1314) from a shuttle (not shown)). In some variations, such as that shown in FIGS. 13A-13C, the snare release button (1308) may be configured to reduce the likelihood that the snare release button (1308) is inadvertently depressed. For example, the snare release button (1308) may be configured such that it does not extend from an outer surface of the handle body (1301). Additionally, the snare release button (1308) may be sized such that it is too small to be depressed by a normal adult finger. For example, in some variations, the snare release button (1308) may have a diameter less than or equal to about 0.20 inches. In some variations, snare release button (1308) may have an oblong cross-section having a major axis of about 0.20 inches and a minor axis of about 0.18 in. In some variations, the handle assembly (1300) may be configured such that the suture control (1304) may actuate the snare release button (1308). Specifically, the suture control (1304) may comprise a grip portion (1312) and a prong (1310) extending therefrom. The tail (1306) of the suture may be attached to the prong (1310) such as described above with respect to the suture control (806) of FIGS. 8A-8F, and may be used to tighten the suture loop. The suture may be disengaged from the suture control (1304), and the prong (1310) may be sized such that it may be used to depress the snare release button (1308), such as shown in a cross-sectional side view in FIG. 13C. When the suture control (1304) is used to depress a snare release button (1308) to release the snare, a user may be forced to release the suture loop from the snare loop assembly prior to releasing the snare.

Figure 17A:
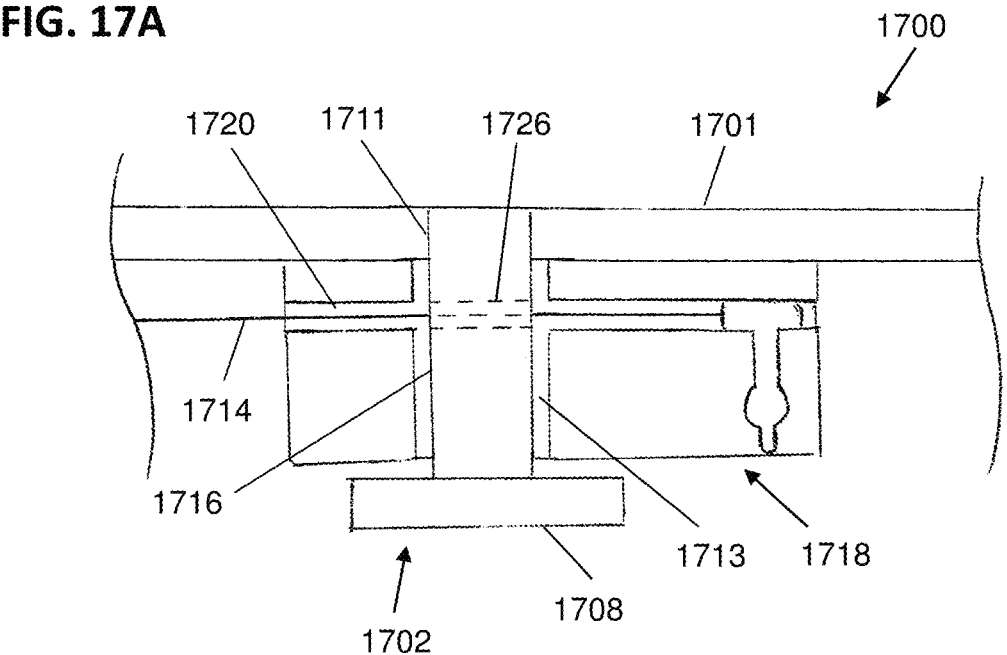
FIGS. 17A and 17B depict cross-sectional top views of a variation of a handle assembly for use with the closure devices described here, the handle assembly including a snare release button.
Figure 17B:
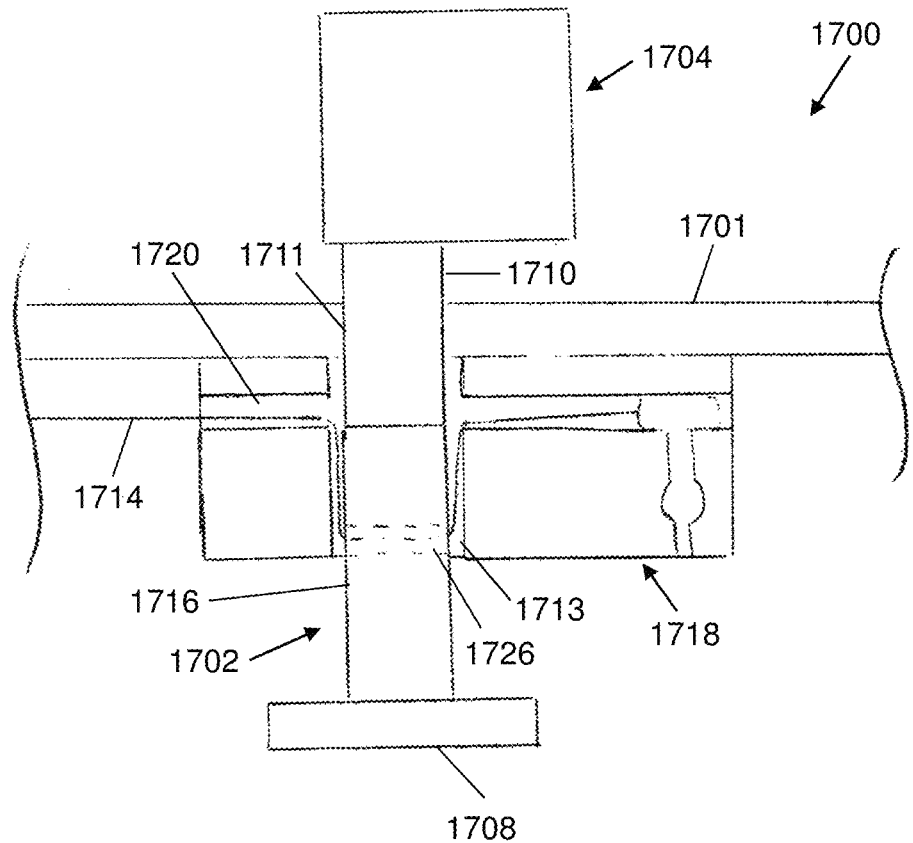
Figure 18A:
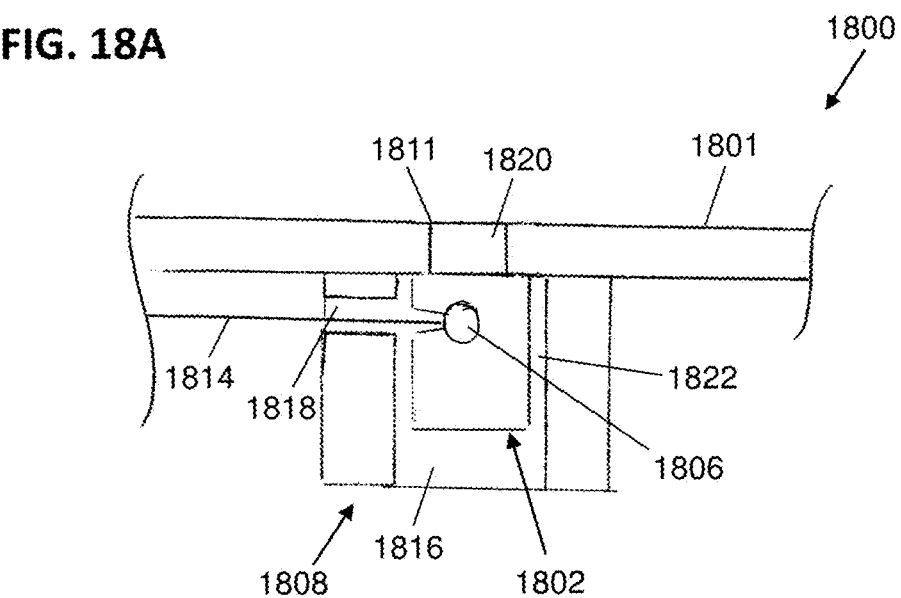
FIGS. 18A and 18B depict cross-sectional top views of another variation of a handle assembly for use with the closure devices described here, the handle assembly including a snare release button.
Figure 18B:
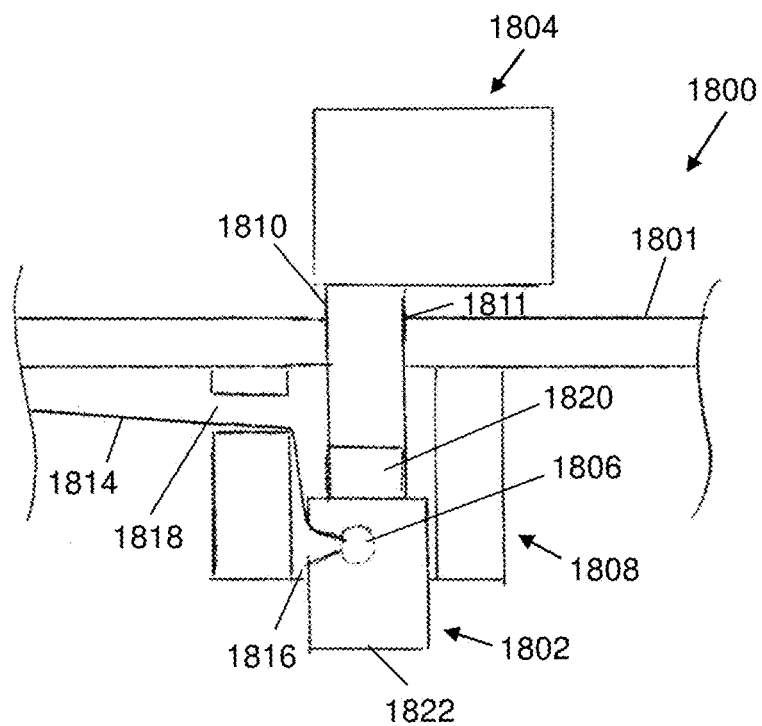

The snare release button may be configured to pull the lock wire proximally relative to the elongate body in a number of ways. In some embodiments the lock wire may be attached to a fixed portion of the handle body, an example of which is depicted in FIGS. 17A and 17B, while in other embodiments the lock wire may be attached to a component configured to move relative to the handle body, an example of which is depicted in FIGS. 18A and 18B. Attaching the lock wire to a fixed portion of the handle body may reduce the amount that the snare release button needs to be depressed to disengage the lock wire, as described in more detail below). Conversely, connecting the lock wire to a moveable component may reduce the force that a user needs to apply to the suture button to disengage the lock wire.

FIGS. 17A and 17B depict cross-sectional top views of a variation of a handle assembly (1700), such as discussed above with respect to FIGS. 13A-13D. As shown there, the handle assembly (1700) may comprise a handle body (1701) and a snare release button (1702). The snare release button (1702) may be movably positioned within a button housing (1718), which in turn may be connected to the interior of the handle body (1701). The button housing (1718) may be formed integrally with the handle body (1701), or it may be formed separately from the handle body (1701) and attached thereto (e.g. via one or more adhesives, bonding, mechanical connection, or the like). Generally, the button housing (1718) may slidably house the snare release button (1702), such that insertion of a portion of a suture control (e.g., a prong (1710) of a suture control (1704) as shown in FIG. 17B) into the handle body (1701) may cause the snare release button (1702) to move relative to the button housing (1718). For example, in some variations the button housing (1718) may include a track or lumen (e.g., a button track (1713) as shown in FIGS. 17A and 17B) which may constrain movement of the snare release button (1702). In some of these variations, the button housing (1718) may constrain movement of the snare release button (1702) along a linear direction (e.g., via the button track (1713)), which in some instances may be perpendicular to the longitudinal axis of the handle body (1701). Additionally, in some instances, the snare release button (1702) may be configured such that it may be prevented from exiting the handle body (1701). In some variations, such as that shown in FIGS. 17A and 17B, the snare release button (1702) may have a stem portion (1716) and a head (1708). In some of these variations, the stem portion (1716) may be slidably positioned in the button housing (1718), while the head (1708) may be sized such that it is prevented from entering the button housing (1718). In other variations, the stem portion (1716) may be sized to extend at least partially through an opening (1711) in the handle body (1701), while the head (1708) is sized such that it may be prevented from passing through the opening (1711) in the handle body (1701).

Also shown in FIGS. 17A and 17B is a lock wire (1714) (which may be any of the lock wires described in more detail above). The snare release button (1702) may comprise a lumen (1726) extending therethrough (e.g., through the stem portion (1716) or another portion of the snare release button (1702)). The lock wire (1714) may be positioned to extend through the lumen (1726) of the snare release button (1702) and at least a portion of the button housing (1718). For example, the button housing (1718) may comprise a lock wire track (1720) extending at least partially therethrough, and the lock wire (1714) may be positioned to extend at least partially through the lock wire track (1720). While the button housing (1718) is depicted with the lock wire track (1720) and button track (1713) exposed, it should be appreciated that the button housing (1718) may comprise a cover or may otherwise be configured to enclose some or all of the lock wire track (1720) and the button track (1713).

Additionally, in the variation shown in FIGS. 17A and 17B, a proximal end of the lock wire (1714) may be attached to a fixed portion of the handle assembly (1700). In these variations, the proximal end of the lock wire (1714) may be connected to any portion of the handle assembly (1700) that is fixed relative to the handle body (1701). In some of these variations, the lock wire (1714) may be connected directly to the handle body (1701). In others of these variations, such as that shown in FIGS. 17A and 17B, the lock wire (1714) may be connected to a portion of the button housing (1718). The proximal end of the lock wire (1714) may be connected to the handle assembly (1700) in any suitable manner (e.g., via adhesives, welding, soldering, mechanical connection using a hook, bolt, screw, or the like). For example, in some variations, an adhesive may fill a portion of the lock wire lumen (1720) to fix a proximal end of the lock wire (1714) to the button housing (1718).

The snare release button (1702) may be actuated from an initial position (as shown in FIG. 17A) to a depressed position (as shown in FIG. 17B), which may disengage the lock wire (1714) from a shuttle to release a fixed end of a snare as discussed in more detail above. In some instances, such as illustrated in FIGS. 17A and 17B, force may be applied to the snare release button (1702) by inserting the prong (1710) of the suture control (1704) through the opening (1711) in the handle body (1701). It should be appreciated, however, that another structure may be inserted into the opening (1711) to apply force to the snare release button (1702) to depress it. As the snare release button (1702) is moved to the depressed configuration, the snare release button (1702) may pull the lock wire (1714) into the button housing (1718). For example, when the snare release button (1702) is in the initial position shown in FIG. 17A, the lumen (1726) of the snare release button (1702) may be aligned with the lock wire lumen (1720). As the snare release button (1702) is depressed, the lumen (1726) of the snare release button (1702) and a portion of the lock wire (1714) may be pushed out alignment with the lock wire lumen (1720), which may pull a length of the lock wire (1714) into the button housing (1718). This in turn may pull a distal end of the lock wire (1714) to disengage it from a shuttle, as discussed in more detail above. Additionally, because the lock wire (1714) is pushed out of alignment with the lock wire lumen (1720) on both sides of the snare release button (1702) as the snare release button (1702) is depressed, the distal portion of the lock wire (1714) may be pulled proximally a distance that is larger than the distance the snare release button (1702) is displaced. In some instances, the snare release button (1702) may be pulled proximally a distance that is twice the distance the snare release button (1702) is displaced.

FIGS. 18A and 18B illustrate another embodiment of a handle assembly (1800) having a snare release button (1802). As depicted there, the snare release button (1802) may be movably positioned within a button housing (1808), which in turn may be connected to the interior of a handle body (1801). The button housing (1808) may be formed integrally with the handle body (1801), or it may be formed separately from the handle body (1801) and attached thereto (e.g., via one or more adhesive, bonding, mechanical connection or the like). Such as discussed above with respect to FIGS. 17A and 17B, the button housing (1808) may slidably house the snare release button (1802), such that insertion of a portion of a suture control (e.g., a prong (1810)) of a suture control (1804) as shown in FIG. 18B) into an opening (1811) of the handle body (1801) may cause the snare release button (1802) to move relative to the button housing (1808). For example, the button housing (1808) may comprise a button track (1816) which may constrain movement of the snare release button (1802) such as discussed above. In some variations, the button track (1816) may constrain movement of the snare release button (1802) along a direction perpendicular to the longitudinal axis of the handle body (1801). The button housing (1808) may further comprise a lock wire track (1818) through which a lock wire (1814) may enter the button housing (1808). The housing may also comprise a cover (not shown) or may otherwise be configured to enclose some or all of the lock wire track (1818) and the button track (1816), but need not. In some variations, such as that shown in FIGS. 18A and 18B, the snare release button (1802) may comprise a stem portion (1820) and a head (1822). In some variations, the stem portion (1820) may be sized to fit at least partially through the opening (1811) in the handle body (1801) (as shown in FIG. 18A), while the head (1808) may be sized such that it may be prevented from passing through the opening (1811) in the handle body (1801). This may prevent the snare release button (1802) from exiting the handle body (1801).

In the variation shown in FIGS. 18A and 18B, a proximal end of the lock wire (1814) may be connected to the snare release button (1802). Specifically, the lock wire (1814) may enter the button housing (1808) through the lock wire track (1818) and connect to the snare release button (1802). The lock wire (1814) may be connected to the snare release button (1802) in any suitable manner (e.g., via adhesives, welding, soldering, mechanical connection, or the like). For example, in the variation shown in FIGS. 18A and 18B, the lock wire (1814) may comprise a post (1806) (such as a screw, or the like), and the lock wire (1814) may be wound around the post to secure the lock wire (1814) thereto. In some variations, a portion of the lock wire (1814) may be held between a portion of the post (1806) and the snare release button (1802). Additionally or alternatively, adhesive may also be applied to the lock wire (1814) to help secure the lock wire (1814) to the post (1806).

The snare release button (1802) may be actuated to disengage a distal portion of the lock wire (1814) from a shuttle to release a fixed end of a snare as discussed in more detail above. Specifically, a force may be applied to the snare release button (1802) to move the snare release button (1802) from an initial position (as shown in FIG. 18A) to a depressed position (as shown in FIG. 18B). In some instances, such as shown in FIGS. 18A and 18B, force may be applied to the snare release button (1802) by inserting a portion of a suture control (1804) (e.g., a prong (1810) of the suture control (1804)) through the opening (1811) in the handle body (1801). It should be appreciated, however, that another structure may be inserted into the opening (1811) to apply force to the snare release button (1802) to depress it. As the snare release button (1802) is moved along the button track (1816), the snare release button (1802) may pull a portion of the lock wire (1814) into the button track (1816), which in turn may pull a portion of the lock wire (1814) into the button housing (1808). As the proximal portion of the lock wire (1814) is pulled by the snare release button (1802), a distal portion of the lock wire (1814) may also be pulled proximally along the elongate body of the closure device, which may in turn disengage the lock wire (1814) from a shuttle. In these variations, the connection of the proximal end of the lock wire (1814) to the snare release button (1802) may reduce the force required to move the snare release button (1802) (e.g., by removing a resistive force that may occur when a proximal end of the lock wire (1814) is attached to a fixed portion of the handle body (1801)).

In some variations, it may be desirable to configure and position the lock wire of a closure device to have a certain amount of slack within the handle assembly and/or the elongate body. For example, when the closure devices described here are heated (e.g., during sterilization), the elongate body may increase in length relative to the lock wire. For example, in the variation of the handle assembly (1300) shown in FIGS. 13A-13C, the lock wire (1314) may be configured to have some slack (1318) in the handle body (1301). Expansion of the elongate body (1316) may cause the slack (1318) of the lock wire (1314) to be pulled taut instead of the lock wire (1314) being pulled from the shuttle. Without the slack of the lock wire (1314), expansion of the elongate body may withdraw the lock wire from a shuttle and prematurely release the snare. The lock wire (1314) may be configured to have any suitable amount of slack (1318) (e.g., at least about 2 mm, at least about 5 mm, or the like). When a snare release (such as the snare release button (1308) shown in FIGS. 13A-13C) is used to withdraw a lock wire relative to the elongate body, the snare release may also pull the lock wire to remove the slack.

Figure 9:
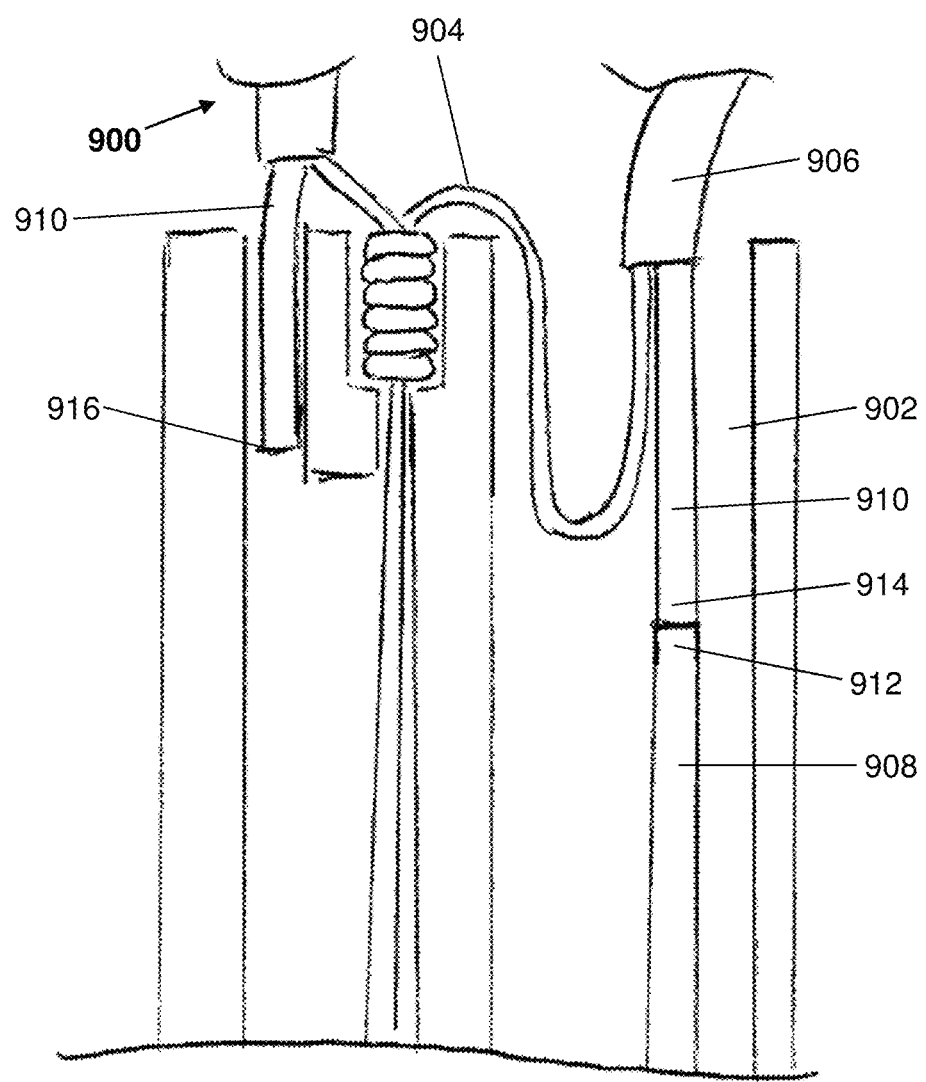
FIG. 9 shows a cross-sectional side view of a portion of a closure device having a releasable snare.

While the releasable snares described above are configured to release a fixed end of the snare, other variations of the releasable snares described here may be configured to release the snare along the length of the snare. For example, FIG. 9 shows a variation of a snare loop assembly (900) having a releasable snare (902). Also shown in FIG. 9 are a suture loop (904) and a retention member (906) coupling the suture loop (904) to the snare (902), as described herein throughout. The releasable snare (902) may have a proximal portion (908) and a distal portion (910) which may be temporarily connected to each other. Specifically, the proximal portion (908) of the snare may have a first end (not shown) and a second end (912), and the distal portion (910) of the snare (902) may have a first end (914) and a second end (916). The second end (916) of the distal portion (910) may be fixed relative to an elongate body (not shown) of the closure device while the first end (914) of the distal portion (910) may be releasably connected to the second end (912) of the proximal portion. The first end of the proximal portion (908) may be operatively connected to a snare control, which may be manipulated to advance or retract the snare (902) relative to the elongate body to open and close the snare loop assembly (900) as described above. To release the snare (900), the second end (912) of the proximal portion (908) of the snare (902) may be disengaged from the first end (914) of the distal portion (910) to release the distal portion (910).

Figure 10A:
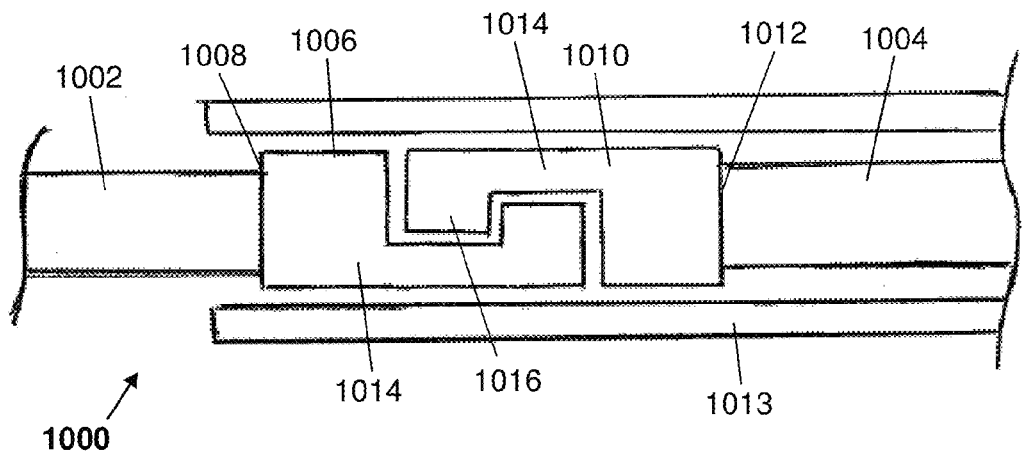
FIGS. 10A and 10B show side views of a portion of one variation of a releasable snare.
Figure 10B:
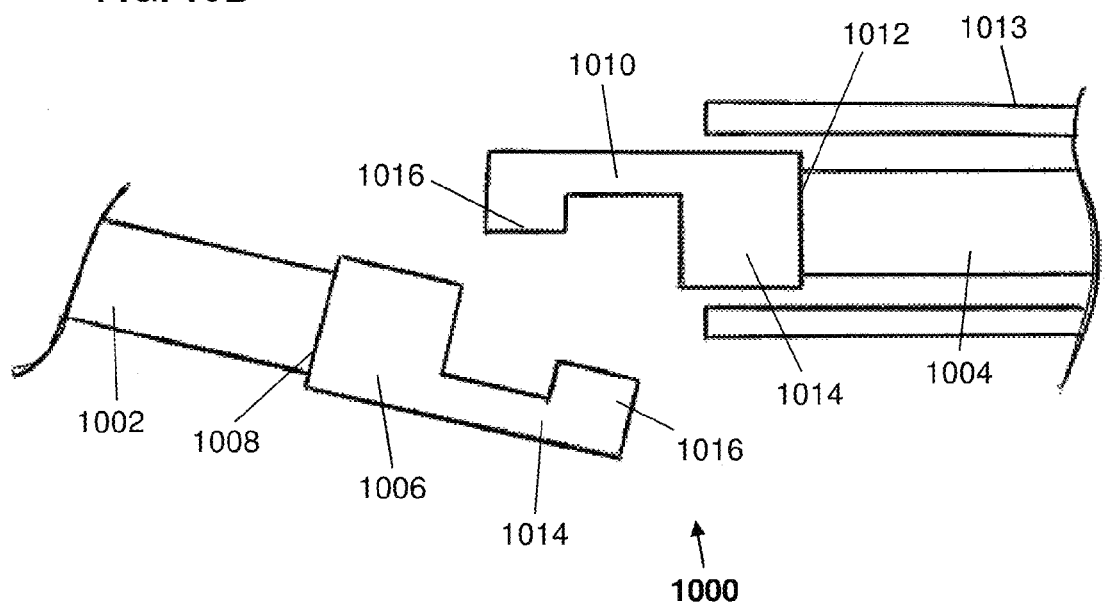

The proximal (908) and distal (910) portions of the snare (902) may be releasably connected in any suitable manner. FIGS. 10A and 10B depict a first such variation of a releasable snare (1000). As shown in FIG. 10A, the snare (1000) may comprise a distal portion (1002) releasably connected to a proximal portion (1004). The distal portion (1002) may have a first engagement portion (1006) connected to a first end (1008) of the distal portion (1002) of the snare (1000) and the proximal portion (1004) may comprise a second engagement portion (1010) connected to a second end (1012) of the proximal portion (1004) of the snare (1000). Generally, the first (1006) and second (1010) engagement portions are configured to temporarily engage each other such that the first (1006) and second (1010) engagement portions are axially fixed along the longitudinal axis of the snare (1000), but may be configured such that radial movement between the first (1006) and second (1010) engagement portions may cause disengagement of the first (1006) and second (1010) engagement portions. To hold the first (1006) and second (1010) engagement portions in the axially-fixed configuration, the snare (1000) may further comprise a restraining sheath (1013). When the first (1006) and second (1010) engagement portions are engaged to axially fix the engagement portions, the restraining sheath (1013) may be positioned around the first (1006) and second (1010) engagement portions such as shown in FIG. 10A. The restraining sheath (1013) may radially constrain the first (1006) and second (1010) engagement portions, and may thereby prevent the first (1006) and second (1010) engagement portions from radially disengaging. To release the distal portion (1002) of the snare, the restraining sheath (1013) may be withdrawn to expose the first (1006) and second (1010) engagement portions as shown in FIG. 10B. The exposed engagement portions may then disengage to release the distal portion (1002) of the snare (1000) relative to the proximal portion (1004) of the snare (1000).

The first (1006) and second (1010) engagement portions may be any suitable structures that can engage and disengage each other in a radial direction, and that may be axially fixed when engaged. For example, in the variation of snare (1000) shown in FIGS. 10A and 10B, the first (1006) and second (1010) engagement portions may comprise hook members (1014) having corresponding shapes, each comprise a lip (1016). The hook members (1014) of the first (1006) and second (1010) engagement portions may be positioned such that the lips (1016) of the hook members (1014) catch on each other (such as shown in FIG. 10B) to prevent the first (1006) and second (1010) engagement portions from being axially pulled apart.

Figure 11A:
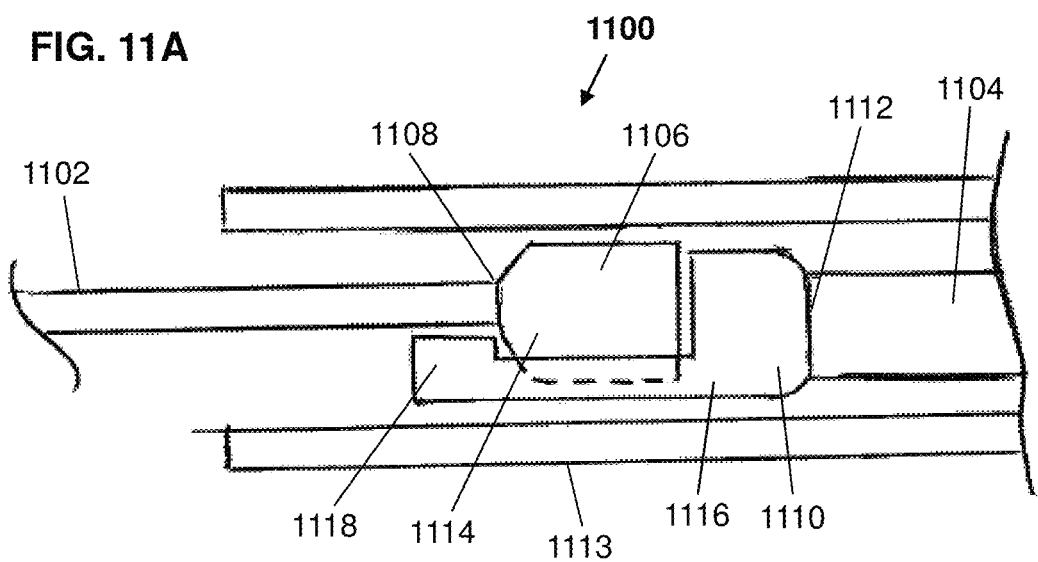
FIGS. 11A and 11B show side views of a portion of one variation of a releasable snare.
Figure 11B:
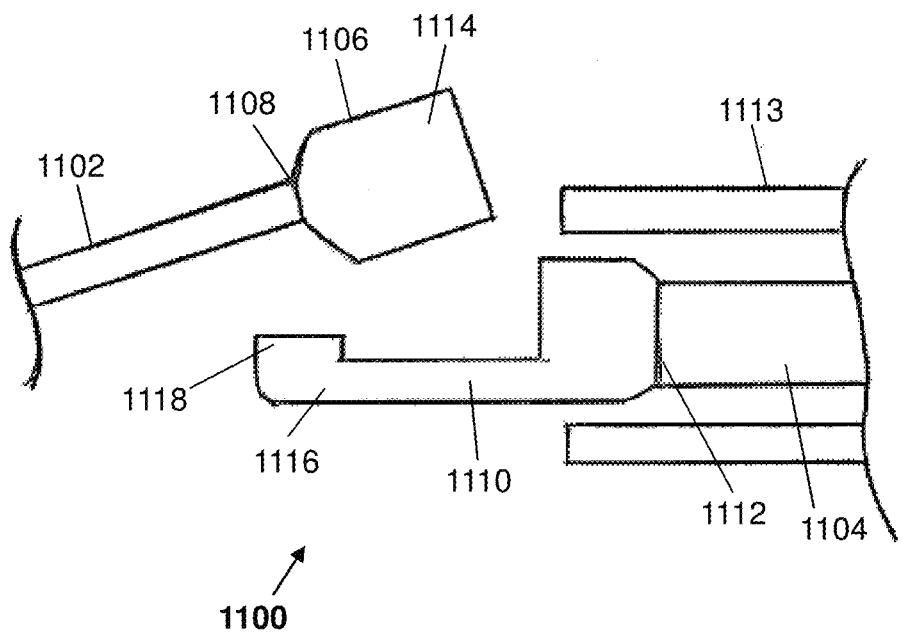

FIGS. 11A and 11B show a second variation of a releasable snare (1100). As shown there, the snare (1100) may comprise a distal portion (1102) and a proximal portion (1104), with the distal portion (1102) comprising a first engagement portion (1106) attached to a first end (1108) of the distal portion (1102) and the proximal portion (1104) comprising a second engagement portion (1110) attached to a second end (1112) of the proximal portion (1104). The snare (1100) may further comprise a restraining sheath (1113), such as described above. In these variations, the first engagement portion (1106) may comprise a slug (1114) and the second engagement portion (1110) may comprise a partially hollow cup (1116) configured to at least partially house the slug (1114). To axially fix the first (1106) and second (1108) engagement portions, the slug (1114) may be positioned at least partially within the cup (1116), and the restraining sheath (1113) may be placed around the slug (1114) and cup (1116) as shown in FIG. 11A to prevent the slug (1114) and cup (1116) from disengaging. Additionally, the cup (1116) may comprise a distal lip (1118) which may prevent the slug (1114) from being pulled axially away from the cup (1116) (e.g., along the longitudinal axis of the snare (1100)). As described above, the restraining sheath (1113) may be withdrawn to expose the first (1106) and second (1108) engagement portions, as shown in FIG. 11B, such that the slug (1114) may disengage the cup (1116) to release the distal portion (1102) of the snare (1100) from the proximal portion (1104) of the snare (1102). While the first engagement portion (1106) is shown in FIGS. 11A and 11B as having a slug (1114) and the second engagement portion (1108) is shown as having a cup (1116), it should be appreciated that in other variations the first engagement portion (1106) may comprise a cup (1116) while the second engagement portion (1108) may comprise a slug (1114).

Figure 12A:
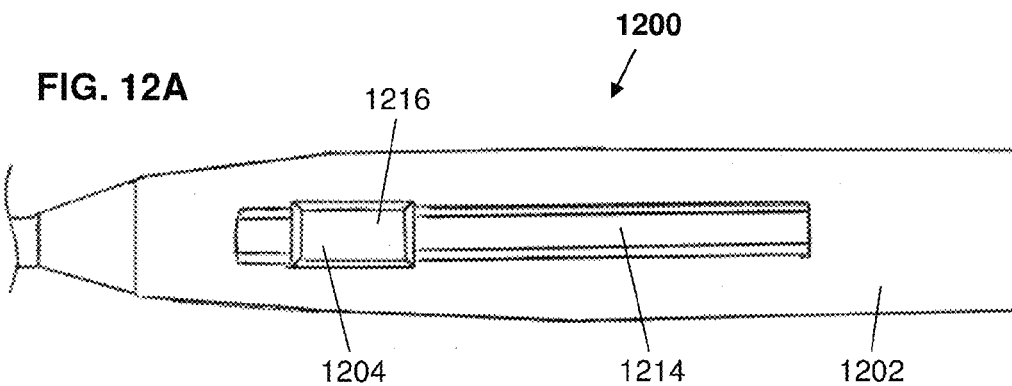
FIGS. 12A-12C depict top views of a handle assembly for use with the closure devices described here.

When the snare loop assembly comprises a releasable snare having a distal portion releasably connected to a proximal portion of the snare and a restraining sheath maintaining the connection between the distal and proximal portions, the snare may be moved and released in any suitable manner. For example, when the proximal and distal portions of the snare are coupled, advancement and retraction of the proximal portion of the snare may in turn advance and retract the distal portion of the snare to open and close the snare loop assembly. When the proximal and distal portions of the snare are advanced and retracted, it may be necessary to also move the restraining sheath with the snare to maintain the engagement between the proximal and distal portions of the snare. For example, FIGS. 12A-12D depict one such variation of a handle assembly (1200) for actuating a snare and releasing a distal portion of the snare from a proximal portion of a snare. Specifically, FIG. 12A shows a top view of the handle assembly (1200) comprising a handle body (1202) and a snare control (1204). The snare control (1204) may be advanced or withdrawn to advance and withdraw, respectively, the snare.

Figure 12B:
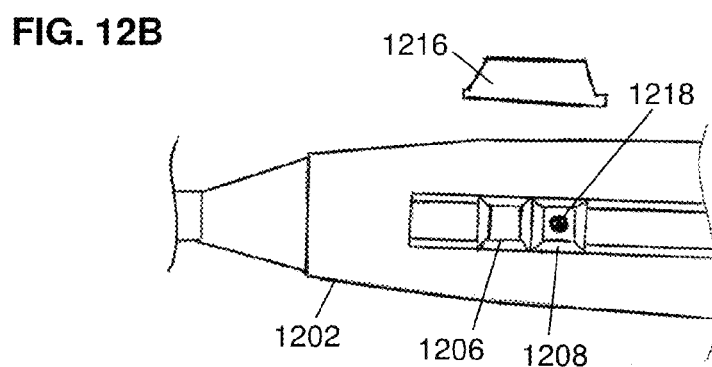
Figure 12C:
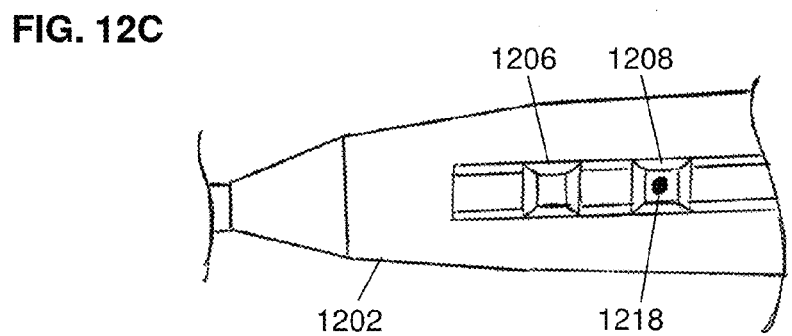
Figure 12D:
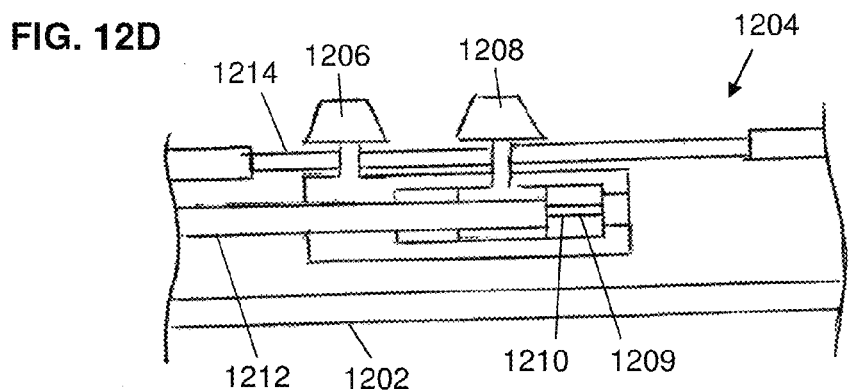
FIG. 12D depicts a cross-sectional side view of a portion of the handle assembly shown in FIGS. 12A-12C.

FIG. 12D shows a cross-sectional side view of a portion of the handle body (1202). As shown there, the snare control (1202) may comprise a first control (1206) and a second control (1208). The first control (1206) may be connected to a proximal portion (1209) of a snare (1210), while the second control (1208) may be connected to the restraining sheath (1212). The first (1206) and second (1208) controls may be independently or jointly moveable along a track (1214) to move the proximal portion (1209) of the snare (1210) and the restraining sheath (1212), respectively. When the first (1206) and second (1208) controls are moved together along the track (1214), the position of the proximal portion (1209) of the snare (1210) relative to the restraining sheath (1212) may be maintained (e.g., to allow the restraining sheath (1212) to continue to hold the proximal (1209) and distal (not shown) portions of the snare (1210) in a connected manner). Conversely, relative movement between the first (1206) and second (1208) controls may move the restraining sheath (1212) relative to the proximal portion (1209) of the snare (1210), which may be used to release a distal portion (not shown) of the snare (1210).

For example, the closure device may be initially configured such that the proximal (1209) and distal portions of the snare (1210) are coupled and held in engagement by the restraining sheath (1212). To manipulate the snare loop assembly of the closure device, the first (1206) and second (1208) controls may be moved together to advance and retract the snare (1210), and thereby open and close the snare loop assembly. In some variations, the snare control (1202) comprises a mechanism to move the first (1206) and second (1208) controls together. For example, as shown in FIG. 12B, the snare control (1200) may comprise a cover (1216) which may be configured to temporarily couple the first control (1206) to the second control (1208). Specifically, the cover (1216) may enclose a portion a portion of each of the first (1206) and second (1208) controls such that a user may advance or retract the cover (1216) to advance or retract, respectively, both the first (1206) and second (1208) controls. In some variations, the cover (1216) may comprise a magnet (not shown) that may magnetically attract and engage a magnet (1218) of the first (1206) and/or second (1208) controls to hold the cover (1216) in place relative to the first (1206) and second (1208) controls, as shown in FIG. 12A. While only the second (1208) control is shown in FIG. 12B as having a magnet (1218), it should be appreciated that in some variations only the first control (1206) may comprise a magnet and in other variations both the first (1206) and second (1208) controls may comprise magnets (1218).

To release the distal end of the snare, the cover (1216) may be disengaged from the first (1206) and second (1208) controls to expose the first (1206) and second (1208) controls, as shown in FIG. 12B. The second control (1208) may be withdrawn proximally relative to the first control (1206) as shown in FIG. 12C to withdraw the restraining sheath (1212) relative to the proximal portion (1209) of the snare (1210). Withdrawal of the restraining sheath (1212) may expose the engagement portions of the proximal and distal snare portions, allowing the engagement portions of the proximal and distal portions to disengage.

Tensioning Devices

When the closure devices described above are used to place and tighten a suture loop around a tissue, it may be desirable to manage the tension applied to the suture as the suture loop is tightened. Accordingly, the closure devices described here may comprise one or more tensioning devices or mechanisms for managing the tension applied to a portion of the suture loop (e.g., a tail of the suture loop) of the closure device. In some instances, it may be desirable to limit the maximum tension that is applied to a suture loop at different times during tightening. For example, if a sufficiently large tension is applied to the suture loop, the suture loop may cut through, shear off, or otherwise damage the ensnared tissue, and/or may break or damage one or more components of the closure device. In some variations, the closure devices described may be configured to limit the tension that is applied to a suture loop during tightening of the suture loop. For example, in variations where the suture is attached to a suture control, the suture control may be configured to break away from a suture upon application of a predetermined force to the suture control (for example, between about 8 lbs and about 10 lbs) to limit the tension applied to the suture.

In other instances, it may be desirable to facilitate the application of at least a minimum tension to a suture during tightening of a suture loop. For example, when the closure devices described here are used to close a portion of the left atrial appendage (e.g., the neck of the left atrial appendage) it may be desirable to maximize closure of the left atrial appendage, which may reduce the possibility of blood or other materials passing into or out of the left atrial appendage through the ostium of the left atrial appendage. Accordingly tightening the suture loop by applying at least a minimum predetermined tension to the suture may help improve closure of the left atrial appendage, as will be described in more detail below. In some variations, the closure device may comprise one or more tensioning devices that may facilitate application of at least a predetermined minimum tension to a suture during tightening. Additionally, application of another predetermined tension to a suture may cause a suture loop to release from the snare loop assembly. By allowing a user to apply one or more predetermined tensions, the tensioning devices may help to reduce user variability between different procedures, which may help to improve repeatability of tensioning across multiple procedures.

In yet other instances, the tensioning devices may be configured to facilitate the application of at least a minimum predetermined tension to a suture loop without exceeding a maximum predetermined tension. Additionally or alternatively, a tensioning device may be configured to facilitate the application of multiple predetermined tensions (or ranges of tensions). For example, in some variations (as will be described in more detail below), a tensioning device may have a first configuration in which the tensioning device facilitates the application of a first predetermined tension to a suture and a second configuration in which the tensioning device facilitates the application of a second predetermined tension to the suture. It may be desirable to enable a user to apply a first predetermined tension to the suture at a first point in time, and a second predetermined tension to the suture at a second point in time, as will be described in more detail below. Examples of suitable tensions devices are described in in U.S. patent application Ser. No. 13/490,919, which was previously incorporated by reference.

Markers

Figure 15A:
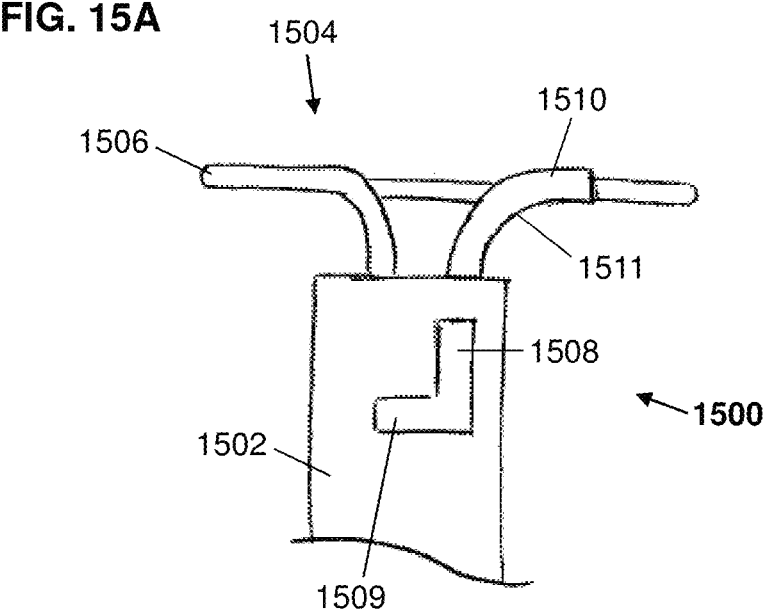
FIGS. 15A and 15B depict top views of a distal portion of one variation of the closure devices described here.
Figure 15B:
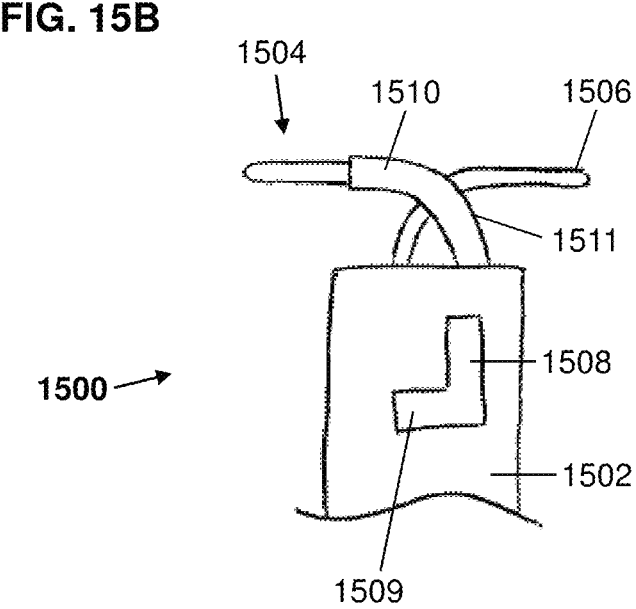

As mentioned above, in some instances it may be desirable to allow a user to determine whether the snare loop assembly has become twisted. For example, in some variations a closure device may comprise one or more markers which may have a first configuration when the snare loop assembly is twisted and a second configuration when the snare loop assembly is untwisted. For example, FIGS. 15A and 15B depict a distal portion of one such variation of a closure device (1500). As shown there, the closure device (1500) may comprise an elongate body having a tip (1502) and a snare loop assembly (1504) extending therefrom. The snare loop assembly (1504) may comprise a snare, a suture loop, and a retention member, such as described above, although only the retention member (1506) is shown in FIGS. 15A and 15B. In this variation, the closure device (1500) may comprise first (1508) and second (1510) markers. The markers may be directly visualized or may be indirectly visualized (e.g., via fluoroscopy, x-ray, or ultrasound visualization).

The markers may be configured to allow a user to determine whether the snare loop assembly (1504) is twisted relative to the tip (1502) of the elongate body. Specifically, the first marker (1508) may be positioned on or in the tip (1502), and may be configured such that the first marker (1508) is not symmetrical with respect to the longitudinal axis of the tip (1502). For example, the first marker (1508) is shown in FIGS. 15A and 15B as being L-shaped, although it should be appreciated that the first marker (1508) may be any suitable non-symmetric shape. The first marker (1508) may allow a user to determine an orientation of the tip (1502). For example, when a leg (1509) of the first marker (1508) may point in a first direction (e.g., to the left, as shown in FIGS. 15A and 15B) when the tip (1502) is in a first rotational orientation, and may point in an opposite direction when the tip (1502) is flipped over. The second marker (1510) may be attached to the snare loop assembly (1504), and may also be configured such that the second marker (1510) is not symmetrical with respect to the longitudinal axis of the tip (1502). In the variation of the closure device (1500) shown in FIGS. 15A and 15B, the second marker (1510) may extend along a subsection of the loop defined by the snare loop assembly (1504) (i.e., the second marker (1510) may not completely circumscribe the loop). For example, the second marker (1510) shown in FIG. 15A may comprise an arc segment (1511). The arc segment (1511) may extend in a first direction relative to the first marker (1508) when the snare loop assembly (1504) is untwisted and extend in an opposite direction relative to the first marker (1508) when the snare loop assembly (1505) is twisted. For example, the arc segment (1511) depicted in FIGS. 15A and 15B may extend in a direction opposite the leg (1509) of the first marker (1508) when the snare loop assembly (1504) is untwisted (as shown in FIG. 15A) and may extend in the same direction as the leg (1509) of the first marker (1508) when the snare loop assembly (1504) is twisted (as shown in FIG. 15B). Accordingly, a user may look at the relative orientation between the first marker (1508) and the second marker (1510) to determine whether the snare loop assembly (1504) is twisted. While the second marker (1510) is shown in FIGS. 15A and 15B as being connected to a retention member (1506) of the snare loop assembly (1504), the second marker (1510) may be attached to any suitable portion or portions of the snare loop assembly (1504) (e.g., a snare, a suture loop, and/or a retention member).

Methods

Methods for closing the left atrial appendage are also described here. It should be appreciated that any of the devices described above may be used in conjunction with one or more of the methods described here or those described in U.S. patent application Ser. No. 13/490,919, which was previously incorporated by reference. Generally, methods described here comprise accessing the left atrial appendage. Once access has been achieved, a closure device (such as those described above) may be advanced to the left atrial appendage. In some variations, the closure devices may be advanced and positioned with the help of one or more guide devices (e.g., a magnetic alignment element) and/or one or more stabilizing/positioning devices (e.g., an expandable member or the like), such as described in U.S. patent application Ser. No. 13/490,919, which was previously incorporated by reference. In some of these variations, a relative orientation between a first marker on a tip of the elongate body and a second marker on a portion of a snare loop assembly may be visualized to determine whether the snare loop assembly is twisted or untwisted, such as described in more detail above. If the snare loop assembly is twisted, the closure device may be retracted or otherwise manipulated to help untwist the snare loop assembly. The closure device may be used to ensnare and close the left atrial appendage. A suture loop or other closure element may be tightened and released from the closure device to hold the left atrial appendage in closed configuration. Once or more tensioning devices may be utilized to tighten and/or release the suture loop. The closure device may be withdrawn, and a portion of the suture may be severed. These steps will be described in more detail below. Additionally, in one or more portions of the closure device may become stuck or otherwise caught on tissue during advancement, manipulation, or other use of the closure device. In these instances, the methods may further comprise releasing one or more portions of a snare of the snare loop assembly. When a portion of the snare is released, they may be released in any suitable manner such as those described above.

As mentioned above, some variations of the methods described here may comprise gaining access to the left atrial appendage. In some variations, the methods for closing the left atrial appendage include accessing the left atrial appendage from both the inside of the heart and the outside of the heart. To access the inside of the heart, the vasculature is typically used. For example, access may be obtained via one or several of the various veins or arteries (jugular, femoral, carotid, etc.). In some variations, the heart is accessed on the inside via the common femoral vein (e.g., the left common femoral vein) using a standard Seldinger technique with a needle. An introducer wire may then be advanced through the needle, followed by an introducer sheath. The introducer wire may then be removed. In some variations, a guiding catheter sheath may be placed as an alternative to an introducer sheath or the initial sheath may be replaced with a guiding catheter sheath.

Using fluoroscopy, an angiogram performed through the sheath, a catheter placed through the sheath, a guiding catheter sheath, or any combination thereof, may be performed to observe anatomical characteristics and considerations of the access route for the purpose of transseptal access into the left atrium (e.g., tortuosity, clots, devices, such as vena cava filters, etc.). Fluoroscopy, ultrasound, intracardiac echocardiography, extracardiac echocardiography, transesophageal echocardiography, or combinations thereof, may be used to help visualize transseptal access to the left atrium, and access to the left atrium may be obtained using standard transseptal access techniques.

For access to the heart from the outside, a subthoracic access point may be used. The access point is typically identified based on patient anatomical characteristics. In some variations, the access point may be any suitable location (e.g., intercostal access via a sternotomy, thoracostomy, or thoracotomy, right of the xiphoid process and pointed towards the patient's left shoulder, or in the costal cartilage or xiphoid process itself). Once the access point has been determined, a needle (e.g., a 17 G Tuohy needle) may be advanced using standard pericardiocentsesis techniques under fluoroscopic guidance. After access to the pericardium has been obtained, a guidewire may be advanced through the needle under fluoroscopic visualization within the pericardial sac. The needle may then be removed. Access to the pericardial space has thus been obtained.

In other variations, the left atrial appendage may be closed off using the systems and devices described here without performing both access procedures as described above. For example, in some variations the methods comprise advancing a first guide having a proximal end and a distal end into the left atrial appendage, through the left atrial appendage, and out of the left atrial appendage, such that one of the proximal or distal ends is within the vasculature, and one of the proximal or distal ends is within the subthoracic space.

By virtue of gaining access to the left atrial appendage, one or more guides having alignment members may be advanced to the left atrial appendage. For example, first and second guides having alignment members may be used to guide the procedure, such as described in U.S. patent application Ser. No. 13/490,919, which was previously incorporated by reference. The alignment member may be any suitable alignment member (e.g., interconnecting elements, one or more vacuum members, radiopaque or echogenic markers, members that are configured to produce an audible response, magnets, etc.). In some variations, the alignment members are magnets located at the distal ends of the guides. The magnets may be made from or comprise any suitable magnetic material, e.g., a rare earth magnet, such as neodymium-iron-boron, cobalt-samarium, or other powerful fixed magnet elements. These guides may be used for guiding additional tools and/or devices to the left atrial appendage.

For example, in some variations, a first guide may be advanced into the left atrial appendage, while the second guide may be advanced into the pericardial space adjacent to the left atrial appendage. Either of these guides may be advanced under any of a variety of visualization techniques, e.g., fluoroscopic visualization, ultrasound visualization, some combination thereof, etc. Once the first and second guide members have been advanced to the left atrial appendage, one or more positioning and/or stabilizing elements (e.g., balloons or other expandable structures) may be advanced over or in conjunction with the first guide (e.g., it may be coupled to or be part of the first guide) and into the left atrial appendage. Similarly, a closure device may be advanced over the second guide to the exterior of the left atrial appendage. It should be appreciated that the closure device may be any of the closure devices described above.

When placed in the left atrial appendage, the positioning element may be used to help position the snare loop assembly of a closure device. In some variations, an expandable structure may be inflated or otherwise expanded in or near the opening of the left atrial appendage and the snare loop assembly of the closure device may be closed around the left atrial appendage distally of the expandable structure. In these variations, the expandable structure may help position the closure device away from the Coumadin ridge. In other variations, the expandable member may be expanded inside of the left atrial appendage. In some of these variations, when the expandable member is expanded, the left atrial appendage may become distended and its shape changed from roughly conical to roughly spherical, thus better defining the junction between the left atrial appendage and left atrium. In addition, the expandable member in its expanded state may be at a pressure much greater than that of the left atrium proper, resulting in a significant differential in tension between the left atrial appendage and the left atrium. In these variations, the expandable member may help position the closure device near the base of the left atrial appendage. In still other variations, one expandable structure may be expanded in or near the opening of the left atrial appendage while a second expandable structure may be expanded inside of the left atrial appendage. In these variations, the snare loop assembly of the closure device may be closed around the left atrial appendage between the two expandable structures, which may help ensure correct device positioning.

It should be appreciated that the expandable structure may be any suitable expandable structure. In some variations, one or more the expandable structures may be a balloon or another inflatable structure. In some of these variations, the balloon or balloons may be attached to a catheter. In some variations, the balloon or inflatable structure may be configured to be detached in an expanded state inside of the left atrial appendage. In other variations, the expandable structure may comprise an expandable mesh or cage structure. This mesh may be self-expanding or mechanically expandable, and may be made from any suitable material (e.g., platinum, nitinol, stainless steel, Dacron wool, PTFE, combinations thereof, or the like). Again, the expandable mesh or cage structure may be configured to be detached in an expanded state in the left atrial appendage, but need not be.

While the expandable member is in an expanded state, the snare loop assembly may be moved to an open configuration and may be placed around a portion of the left atrial appendage. Once placed around the left atrial appendage, the snare loop assembly may be closed around the left atrial appendage. In some variations, the snare loop assembly is placed around the left atrial appendage while the balloon is in its deflated or unexpanded stated, and then the balloon is expanded after the snare loop assembly is closed. In some instances it may be desirable to confirm proper closure of the appendage prior to tightening of the suture. If closure is not adequate or otherwise not desirable, the snare loop assembly may be opened, repositioned, closed, and then confirmed once again.

Once proper closure has been affected, the suture loop may be tightened to release the suture loop from the snare loop assembly. In some variations, the snare loop assembly may then be returned to an open configuration and the suture loop may be tightened again. This may act to help ensure that the suture loop is sufficiently tightened around the left atrial appendage. In some variations, a user may re-tighten the suture loop after waiting for a period of time. This waiting period may allow tissue to readjust and settle within suture loop, which may allow for a tighter closure of tissue. This period of time may be any suitable period of time, such as, for example, greater than about 30 seconds, greater than about a minute, or greater than about 2 minutes. After releasing the suture loop from the snare loop assembly, the closure device may be withdrawn. In some variations, it may be desirable to further tighten the suture loop after the closure device has been withdrawn. This may be accomplished with one or more additional devices (e.g., a knot pusher).

It should be appreciated that one or more of the tensioning devices described above may be utilized to manage the tension applied to the suture loop during tightening of the suture loop, which may increase repeatability of suture loop tightening by reducing user variation, such as described in U.S. patent application Ser. No. 13/490,919, which was previously incorporated by reference.

It should be appreciated that some or all of the guide member or positioning elements may be removed from the left atrial appendage at any suitable point or points during the methods. For example, in some variations, some or all of these devices or device components may be removed from the left atrial appendage after closing the snare loop assembly but prior to releasing the suture loop from the snare loop assembly. In other variations, some or all of these structures may be removed after releasing the suture loop from the snare loop assembly. The suture loop may be further tightened after some or all of these elements are removed. In still other variations, one or more expandable members may be detached and may remain in the left atrial appendage. In these variations, the expanded member may act to displace blood from the left atrial appendage and to help keep additional blood from entering the left atrial appendage. When the expandable member comprises a balloon or inflatable structure, the balloon may be filled with any suitable substance, such as, for example, saline or one or more hydrophilic polymers (e.g., hydroxyethyl methacrylate).

In yet other variations, one of the guide members or other elements placed inside of the left atrial appendage may be configured to release one or more materials to the closed left atrial appendage prior to removal. This material may act to create haemostasis or embolization of the closed left atrial appendage, which may prevent the ingress and egress of blood from the closed left atrial appendage. Examples of suitable materials include, but are not limited to gelatins (e.g., gel foam), liquid embolic agents (e.g. n-butyle-2-cyanoacrylate, ethidol), gelatin microspheres (e.g., polyvinyl alcohol acrylic microspheres), or pieces of thrombotic materials (e.g., platinum, stainless steel, Dacron wool, combinations thereof or the like).

In some variations, it may be desirable to lock the suture knot in place once the suture loop has been tightened around the left atrial appendage. In some variations, the suture knot may be locked using one or more unidirectional locking structures, as described in more detail above. In other variations, the knot may be locked in place with one or more bioglues or other biocompatible adhesives (e.g., cyanoacrylate). In still other variations, energy (e.g., RF energy, thermal energy, light energy, or the like) may be used to fuse the knot in place. In yet other variations, one or more portions of the suture knot may be configured to expand upon application of or exposure to one or more stimuli. For example, in some variations the suture may comprise collagen filaments that may be exposed to moisture when the suture is severed. Once the collagen is exposed to moisture, it may expand to lock the suture knot in place.

Once the suture loop has been properly placed, the suture may be severed in any suitable fashion, and at any suitable location along its length (i.e., from immediately adjacent to the knot at the left atrial appendage to just proximal to, or just distal to, the skin surface). In some instances it may be desirable to sever the suture at the knot itself (e.g., in instances where it is desirable to release tension on the suture entirely). The suture may be severed in any suitable manner, such as for example by mechanically cutting, or by the application of energy. For example, the suture may be severed with the application of light energy, thermal energy, RF energy, electrical energy, magnetic energy, electromagnetic energy, kinetic energy, chemical energy, and combinations of any of the above.

Although the foregoing invention has, for the purposes of clarity and understanding been described in some detail by way of illustration and example, it will be apparent that certain changes and modifications may be practiced, and are intended to fall within the scope of the appended claims. Additionally, it should be appreciated that the closure devices described here may comprise any combination of device components and features described above.

We claim:

1. A device for closing a target tissue comprising:
an elongate body;
a snare loop assembly extending at least partially from the elongate body, wherein the snare loop assembly comprises a snare comprising a snare loop and a suture loop releasably attached to the snare, wherein the snare comprises a first end and a second end, and wherein advancement of the first end of the snare relative to the elongate body increases the diameter of the snare loop and wherein retraction of the first end of the snare relative to the elongate body decreases the diameter of the snare loop;
a shuttle, wherein the second end of the snare is connected to the shuttle; and
a locking element, wherein the locking element is configured to releasably couple the shuttle to the elongate body and is further configured to release the shuttle from the elongate body, and wherein when the shuttle is released, the first and second ends of the snare are spaced apart.

2. The device of claim 1 wherein elongate body comprises a recess in a side wall of the elongate body, and wherein the shuttle is positioned in the recess when the shuttle is releasably coupled to the elongate body.

3. The device of claim 2 wherein the locking element comprises a lock wire.

4. The device of claim 3 wherein the lock wire extends through a lock wire lumen of the elongate body and a lock lumen of the shuttle when the shuttle is releasably coupled to the elongate body.

5. The device of claim 4 wherein the lock wire comprises a bend.

6. The device of claim 5 wherein the bend extends at least partially into a window of the shuttle when the shuttle is releasably coupled to the elongate body.

7. The device of claim 2 wherein the shuttle comprises a projection configured to fit within a channel within the recess of the elongate body and configured to resist rotation between the shuttle and the elongate body.

8. The device of claim 2 wherein the recess of the elongate body comprises a projection configured to fit within a channel of the shuttle and configured to resist rotation between the shuttle and the elongate body.

9. The device of claim 1 further comprising a handle attached to the elongate body.

10. The device of claim 9 wherein the handle comprises a suture control for tightening the suture loop, a snare control to control movement of the first end of the snare, and a snare release configured to release the shuttle from the elongate body.

11. The device of 10 wherein the locking element comprises a lock wire, and wherein the snare release is configured to retract the lock wire.

12. The device of claim 10 wherein the snare release comprises a button configured to release the shuttle upon depression of the button.

13. The device of claim 12 wherein the suture control comprises a grip portion and a prong extending therefrom, wherein the prong is sized and configured to depress the button of the snare release.

14. The device of claim 10 wherein the suture control comprises a grip portion and a chamber in the grip portion, wherein the chamber is configured to at least partially enclose the snare release.

15. A device for closing a target tissue comprising:
an elongate body;
a snare loop assembly extending at least partially from the elongate body, wherein the snare loop assembly comprises a snare comprising a snare loop and a suture loop releasably attached to the snare, wherein the snare comprises a proximal snare portion and a distal snare portion, each comprising an engagement portion, and wherein the engagement portion of the proximal snare portion is configured to releasably engage the engagement portion of the distal snare portion; and
a restraining sheath positioned to maintain engagement of the proximal and distal snare portions, and wherein when the restraining sheath is withdrawn, the proximal and distal snare portions are spaced apart.

16. The device of claim 15 wherein the engagement portion of the distal snare portion comprises a first hook member and the engagement portion of the proximal snare portion comprises a second hook member.

17. The device of claim 15 wherein the engagement portion of the distal snare portion comprises a slug and the engagement portion of the proximal snare portion comprises a cup member.

18. The device of claim 15 wherein the engagement portion of the distal snare portion comprises a cup member and the engagement portion of the proximal snare portion comprises a slug.

19. The device of claim 15 further comprising a handle, wherein the handle comprises a snare control.

20. The device of claim 19 wherein the snare control comprises a first control operatively connected to the proximal snare portion and a second control operatively connected the restraining sheath.

21. The device of claim 20 wherein the first and second controls are configured to be moved together to simultaneously advance or retract the proximal snare portion and the restraining sheath.

22. The device of claim 21 wherein the first and second controls are configured such that proximal movement of the second control relative to the first control withdraws the restraining sheath relative to the proximal snare portion to disengage the proximal snare portion and distal snare portion.

23. The device of claim 22 wherein the snare control further comprises a removable cover configured to couple the first control and the second control.

24. The device of claim 23 wherein the removable cover comprises one or more magnets which engages a magnet of the first and/or second controls.

* * * * *